United States Patent [19]
Ennis et al.

[11] Patent Number: 6,043,266
[45] Date of Patent: Mar. 28, 2000

[54] PHENYLOXAZOLIDINONES HAVING A C—C BOND TO 4-8 MEMBERED HETEROCYCLIC RINGS

[75] Inventors: Michael Dalton Ennis, Portage; David John Anderson, Kalamazoo, both of Mich.

[73] Assignee: Pharmacia & Upjohn Company, Kalamazoo, Mich.

[21] Appl. No.: 09/313,468

[22] Filed: May 17, 1999

Related U.S. Application Data

[62] Division of application No. 08/696,313, Aug. 13, 1996
[60] Provisional application No. 60/003,149, Sep. 1, 1995.

[51] Int. Cl.[7] .......................... A61K 31/42; C07D 413/10
[52] U.S. Cl. .............................................. 514/376; 548/231
[58] Field of Search ............... 548/231; 514/376

[56] References Cited

U.S. PATENT DOCUMENTS

| | | | |
|---|---|---|---|
| 4,476,136 | 10/1984 | Dostert et al. | 548/229 |
| 4,705,799 | 11/1987 | Gregory | 548/229 |
| 4,948,801 | 8/1990 | Carlson et al. | 548/229 |
| 5,130,316 | 7/1992 | Carson et al. | 548/229 |
| 5,254,577 | 10/1993 | Carlson et al. | 548/229 |
| 5,547,950 | 8/1996 | Hutchinson et al. | 544/369 |
| 5,565,571 | 10/1996 | Barbachyn et al. | 546/275 |
| 5,668,286 | 9/1997 | Yamada et al. | 546/209 |
| 5,684,023 | 11/1997 | Reidl et al. | 548/231 |
| 5,698,574 | 12/1997 | Reidl et al. | 548/229 |

FOREIGN PATENT DOCUMENTS

| | | |
|---|---|---|
| 0 352 781 | 1/1990 | European Pat. Off. . |
| 93 09 103 | 5/1993 | WIPO . |
| 97 09 328 | 3/1997 | WIPO . |

*Primary Examiner*—Mukund J. Shah
*Assistant Examiner*—V Balasubramanian
*Attorney, Agent, or Firm*—Lucy X. Yang

[57] ABSTRACT

A compound of Formula (I):

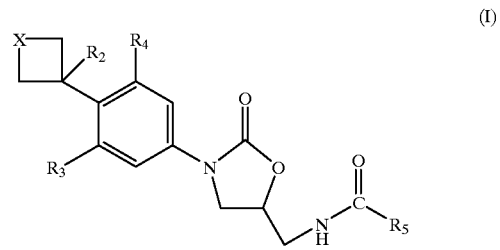

or pharmaceutical acceptable salts thereof wherein X is $S(O)_g$ or O; $R_2$ is H, methyl, or OH; $R_3$ and $R_4$ are independently H or halo; $R_5$ is H, $C_{1-12}$ alkyl, optionally substituted with one or more halo, $C_{3-12}$ cycloalkyl, $C_{1-6}$ alkoxy; and g is 0, 1, or 2. The compounds are useful antimicrobial agents.

8 Claims, No Drawings

PHENYLOXAZOLIDINONES HAVING A C—C BOND TO 4-8 MEMBERED HETEROCYCLIC RINGS

CROSS-REFERENCE TO RELATED APPLICATIONS

This application is a divisional application of U.S. patent application Ser. No. 08/696,313, filed Aug. 13, 1996, which in turn claims the benefit of the following provisional application: U.S. Ser. No.60/003,149, filed Sep. 1, 1995, under 35 USC 119(e)(i).

BACKGROUND OF THE INVENTION

The present invention relates to new and useful N-phenyloxazolidinone compounds and their preparations, and more particularly to N-phenyloxazolidinone compounds in which the phenyloxazolidinone moiety is linked to a variety of saturated, or partially saturated, 4–8 membered heterocycles containing oxygen, nitrogen, and sulfur through a carbon-carbon bond.

The compounds are useful antimicrobial agents, effective against a number of human and veterinary pathogens, including gram-positive aerobic bacteria such as multiply-resistant staphylococci and streptococci, as well as anaerobic organisms such as bacteroides and clostridia species, and acid-fast organisms such as *Mycobacterium tuberculosis* and *Mycobacterium avium*. The compounds are particularly useful because they are effective against the latter organisms which are known to be responsible for infection in persons with AIDS.

INFORMATION DISCLOSURE

A series of Delalande patent applications (Derwent Abstracts 61219Y/35, 67436R-B, 84475A/47) disclose a saturated nitrogen heterocycle linked through the nitrogen atom to a phenyloxazolidinone moiety.

French Patent (FR2500450 A1 820827) discloses cyclohexenone attached at the 3-position to a phenyloxazolidinone.

Other references disclose fully aromatic heterocycles attached to a phenyloxazolidinone, including European Patent Publication 0352 781 A2, U.S. Pat. No. 5,130,316, U.S. Pat. No. 5,254,577, U.S. Pat. No. 4,948,801, and WO 9309103-A1, whereas in our present invention the heterocycle is saturated or partially saturated.

SUMMARY OF THE INVENTION

The present invention provides new compounds of the Formula (I)

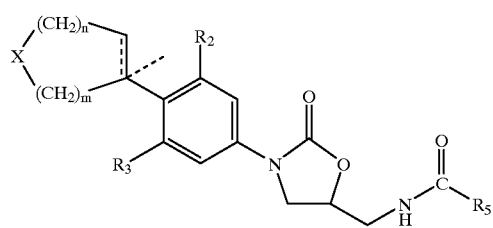

(I)

or pharmaceutical acceptable salts thereof wherein:

X is
a) $NR_1$,
b) $S(O)_g$, or
c) O;

$R_1$ is
a) H,
b) $C_{1-6}$ alkyl, optionally substituted with one or more OH, CN, or halo,
c) —$(CH_2)_h$-aryl,
d) —$COR_{1-1}$,
e) —$COOR_{1-2}$,
f) —CO—$(CH_2)_h$—$COR_{1-1}$,
g) —$SO_2$—$CO_{1-6}$ alkyl,
h) —$SO_2$—$(CH_2)_h$-aryl, or
i) —$(CO)_i$-Het;

$R_{1-1}$ is
a) H,
b) $C_{1-6}$ alkyl, optionally substituted with one or more OH, CN, or halo,
c) —$(CH_2)_h$-aryl, or
d) —$(CH_2)_h$-$OR_{1-3}$;

$R_{1-2}$ is
a) $C_{1-6}$ alkyl, optionally substituted with one or more OH, CN, or halo,
b) —$(CH_2)_h$-aryl, or
c) —$(CH_2)_h$—$OR_{1-3}$;

$R_{1-3}$ is
a) H,
b) $C_{1-6}$ alkyl,
c) —$(CH_2)_h$-aryl, or
d) —$CO(C_{1-6}$ alkyl);

$R_2$ is
a) H,
b) $C_{1-6}$ alkyl,
c) —$(CH_2)_h$-aryl, or
d) halo;

$R_3$ and $R_4$ are independently
a) H, or
b) halo;

$R_5$ is
a) H,
b) $C_{1-12}$ alkyl, optionally substituted with one or more halo,
c) $C_{3-12}$ cycloalkyl,
d) $C_{1-6}$ alkoxy;

g is 0, 1, or 2;
h is 1, 2, 3, or 4;
i is 0 or 1;
m is 0, 1, 2, 3, 4, or 5;
n is 0, 1, 2, 3, 4, or 5;
and with the provisio that m and n taken together are 1, 2, 3, 4, or 5.

More particularly, the present invention provides compounds of formula (I) wherein $R_1$ is H, fluoroethyl, cyanomethyl, methyl sulfonyl, formyl, hydroxyacetyl, acetyl, methoxyacetyl, benzyloxyacetyl, acetoxyacetyl, dichloroacetyl, methoxy carbonyl, tert-butoxy carbonyl, benzyloxy carbonyl, 3-hydroxypropionyl, 3-methoxypropionyl, 4-oxopentanoyl, 2-indole carbonyl, 5-isoxazole carbonyl, 5-nitro-2-thiazoyl, 4-oxo-2-thiazolinyl, or 5-methyl-1,3,4-thiadiazol-2-yl.

$R_2$ is H, F, is H, F, or $CH_3$;
$R_3$ and $R_4$ are the same or different and are H or F; and $R_5$ is methyl or methyl substituted with one or more F or Cl.

The present invention also provides a method for treating microbial infections in patients by administering to a patient in need thereof an effective amount of a compound of Formula (I). The compound can be administered orally, parenterally or topically in a pharmaceutical composition. Preferably, the compound is administered in an amount of from about 0.1 to about 100 mg/kg of body weight/day.

DETAILED DESCRIPTION OF THE INVENTION

For the purpose of the present invention, the term "$C_{1-6}$ alkyl" and the term "$C_{1-12}$ alkyl" refer to any straight or branched alkyl group having one to six or one to twelve carbons respectively such as, for example, methyl, ethyl, n-propyl, isopropyl, n-butyl, isobutyl, sec-butyl, t-butyl, n-pentyl, isopentyl, n-hexyl, isohexyl, n-heptyl, n-octyl and the like.

The term "$C_{1-6}$ alkyl sulfonyl" refers to any straight or branched alkyl group having one to six carbons attached to —$SO_2$ forming such groups as, for example, methyl sulfonyl, ethyl sulfonyl, isopropyl sulfonyl and the like.

The term "$C_{3-12}$ cycloalkyl" refers to three to twelve carbon atoms forming cyclopropyl, cyclobutyl, cyclopentyl, cyclohexyl and the like.

The term "$C_{1-4}$ alkoxy" and the term "$C_{1-6}$ alkoxy" refer to any straight or branched alkyl group having one to four or one to six carbons, respectively, attached to an oxygen forming such groups as, for example, methoxy, ethoxy, n-propoxy, isopropoxy, n-butyloxy, isobutyloxy, sec-butyloxy, t-butyloxy, n-pentyloxy, isopentyloxy, n-hexyloxy, iso-hexyloxy and the like.

The term halo refers to fluoro, chloro, bromo, or iodo.

The term "aryl" refers to a phenyl, pyridyl or napthyl moiety which can be optionally substituted with one or more F, Cl, Br, I, CN, OH, SH, $C_{1-6}$ alkyl, $C_{1-6}$ alkoxy, or $C_{1-6}$ thioalkyl.

The term "Het" refers to 5 to 10 membered heterocyclic rings containing one or more oxygen, nitrogen, and sulfur forming such groups as, for example, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl,1-purinyl, 3-isothiazolyl, 4isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-thiazolone. Each of these moieties may be substituted as appropriate.

The term "pharmaceutically acceptable salts" refers to salts useful for administering the compounds of this invention and include hydrochloride, hydrobromide, hydroiodide, sulfate, phosphate, acetate, propionate, lactate, mesylate, maleate, malate, succinate, tartrate, citrate, 2-hydroxyethyl sulfonate, fumarate and the like. These salts may be in hydrated form.

In the structural representation of Formula (I) the dotted line in the heterocyclic ring means that this bond can be either single or double. In the case here the dotted line is a double bond, the $R_2$ group will not be present.

In a preferred embodiment of the N-phenyloxazolidinone compounds of the resent invention, the X group is preferably $NR_1$, $SO_2$, or oxygen.

The $R_1$ substituent on the nitrogen atom can be introduced by synthetic methods known to those skilled in the art from commercially available reagents.

The preferred $R_1$ substituent is H, fluoroethyl, cyanomethyl, methyl sulfonyl, formyl, hydroxyacetyl, acetyl, methoxyacetyl, benzyloxyacetyl, acetoxyacetyl, dichloroacetyl, methoxy carbonyl, tert-butoxy carbonyl, benzyloxy carbonyl, 3-hydroxypropionyl, 3-methoxypropionyl, 4-oxopentanoyl, 2-indole carbonyl, 5-isoxazole carbonyl, 5-nitro-2-thiazolyl, 4-oxo-2-thiazolinyl, or 5-methyl-1,3,4-thiadiazol-2-yl. The most preferred $R_1$ substituent is formyl, methoxy carbonyl, or hydroxyacetyl.

Where heterocyclic rings are the saturated derivatives, the preferred $R_2$ substituent is hydrogen, fluoro, or methyl.

The preferred $R_3$ and $R_4$ substituents are independently hydrogen or fluoro.

The preferred $R_5$ substituent is methyl.

The most preferred compounds in this series would be prepared as the optically pure enantiomers having the (S)-configuration according to the Cahn-Ingold-Prelog notation at C5 of the oxazolidinone ring. Optically pure material could be prepared by one of a number of asymmetric syntheses. For example, treatment of intermediate compound 12 in CHART B with an appropriate base, followed by addition of (R)-glycidyl butyrate would afford the corresponding oxazolidinone in optically pure form with the requisite (S)-configuration at the 5-position of the oxazolidinone ring. Although the (S)-enantiomer of this series of compounds is preferred since it is pharmacologically active as an antibacterial agent, the racemic modification is also useful in the same manner as the pure (S)-enantiomer; the difference being that twice as much racemic material is required to elicit the same antibacterial effect.

CHART A illustrates methods for preparing compounds of Formula (I) having a heterocycle containing nitrogen. As shown in CHART A, the key intermediate 1 can be used to make derivatives by reactions known to those skilled in the art. For example, acylation affords 2 and 3, the subsequent deprotection of 2 provides 2', alkylation affords 5 (the substituents including hydroxy, nitro, halo, aryl, and sulfonyl; structure 5 also encompasses products having a heteroatomic nucleus), sulfonylation affords 6, and alkoxyacylation affords 4.

A method for preparing compounds of intermediate 1 having a 4-membered heterocycle containing nitrogen in highly enantiomerically enriched form is depicted in CHART B. The first step involves treatment of structure 7 with ethyl cyanoacetate in the presence of an appropriate base, such as sodium hydride or potassium carbonate, at a temperature in the range of −10° C. to 100° C. The subsequent alkylation using allyl halides or tosylates affords nitrile derivative 8. The nitrile derivative 8 is then reduced by catalytic hydrogenation in the presence of an appropriate catalyst, such as palladium on carbon, W-2 Raney nickel or platinum on sulfide carbon, in an appropriate solvent, such as ethyl acetate, THF, methanol or combinations thereof, to give amino-aniline 9, which upon treatment with an appropriate base, preferably methyl or ethyl Grignard, affords the lactam 10. Reduction of 10 by using an appropriate reducing agent, such as LAH or borane, gives the azetidine 11, which reacted with benzyl chloroformate, at a temperature in the range of −10° C. to 10° C., affords the corresponding benzyl carbamate derivatives 12. The treatment of 12 with n-butyllithium in an appropriate solvent such as THF, at a temperature in the range of −78° C. to −40° C., followed by addition of commercially available (R)-glycidyl butyrate dropwise would afford the corresponding oxazolidinone 13 in enantiomerically enriched form at the 5-position of the oxazolidinone ring. As shown in CHART B, compound 13 can be converted to the corresponding alkyl or aryl sulfonate 14 by treatment with alkyl or aryl sulfonyl chloride in the presence of triethylamine or pyridine (wherein R' is $CO_{1-4}$ alkyl or (un)substituted phenyl). The resultant sulfonate 14 is then treated with an alkali metal azide such as sodium or potassium azide, in an aprotic dipolar solvent such as DMF or N-methylpyrrolidinone (NMP), with an optional catalyst such as 18-crown-6, at a temperature in the range of 50° C. to 90° C. to afford azide derivatives. The azide derivatives can be reduced to the corresponding amine 15 by hydrogenation in the presence of a palladium, platinum or nickel catalyst, in an appropriate solvent such as ethyl acetate, THF, or methanol. Alternatively, amine 15 can be prepared by treating 14 with an appropriate solvent such as methanol and/or THF which is saturated with ammonia and heating the mixture to 100° C. in a sealed tube. The reaction occurs over hours, e.g., 40–70 hours. Amine 15 is then acylated with an acid chloride or anhydride in the presence of a base such as pyridine or triethylamine at temperatures ranging from −40° C. to 40° C. to provide the N-acyl oxazolidinone 16. Finally, catalytic hydrogenation of 16 in the presence of a noble metal catalyst, such as palladium on carbon or palladium hydroxide on carbon affords the azetidine 17. The azetidine 17 can be used to prepare derivative compounds demonstrated in CHART A.

The following compounds of Formula (I) having a 4-membered heterocycle containing nitrogen, for example, are prepared directly by the methods described in CHART A and CHART B:

(S)-N-[[3-[3-Fluoro-4-[1-(carbobenzyloxy)-(3-methyl)-3-azetidinyl]-phenyl]-2-oxo-5-oxazolidinyl]methyl]-acetamide;

(S)-N-[[3-[3-Fluoro-4-[3-methyl-3-azetidinyl]-phenyl]-2-oxo-5-oxazolidinyl]methyl]-acetamide;

(S)-N-[[3-[3-Fluoro-4-[1-(methoxycarbonyl)-3-(3-methyl)-azetidinyl]-phenyl]-2-oxo-5-oxazolidinyl]methyl]-acetamide;

(S)-N-[[3-[3-Fluoro-4-[1-(methoxyacetyl)-3-(3-methyl)-azetidinyl]-phenyl]-2-oxo-5-oxazolidinyl]methyl]-acetamide;

(S)-N-[[3-[3-Fluoro-4-[1-(formyl)-3-(3-methyl)-azetidinyl]-phenyl]-2-oxo-5-oxazolidinyl]methyl]-acetamide;

(S)-N-[[3-[3-Fluoro-4-[1-(dichloroacetyl)-3-(3-methyl)-azetidinyl]-phenyl]-2-oxo-5-oxazolidinyl]methyl]-acetamide;

(S)-N-[[3-[3-Fluoro-4-[1-(3-methoxypropionyl)-3-(3-methyl)-azetidinyl]-phenyl]-2-oxo-5-oxazolidinyl]methyl]-acetamide;

(S)-N-[[3-[3-Fluoro-4-[1-(3-hydroxypropionyl)-3-(3-methyl)-azetidinyl]-phenyl]-2-oxo-5-oxazolidinyl]methyl]-acetamide;

(S)-N-[[3-[3-Fluoro-4-[1-(4-oxopentanoyl)-3-(3-methyl)-azetidinyl]-phenyl]-2-oxo-5-oxazolidinyl]methyl]-acetamide;

(S)-N-[[3-[3-Fluoro-4-[1-acetyl-3-(3-methyl)-azetidinyl]-phenyl]-2-oxo-5-oxazolidinyl]methyl]-acetamide;

(S)-N-[[3-[3-Fluoro-4-[1-(2-fluoroethyl)-3-(3-methyl)-azetidinyl]-phenyl]-2-oxo-5-oxazolidinyl]methyl]-acetamide;

(S)-N-[[3-[3-Fluoro-4-[1-(cyanomethyl)-3-(3-methyl)-azetidinyl]-phenyl]-2-oxo-5-oxazolidinyl]methyl]-acetamide;

(S)-N-[[3-[3-Fluoro-4-[1-(5-nitro-2-thiazolyl)-3-(3-methyl)-azetidinyl]-phenyl]-2-oxo-5-oxazolidinyl]methyl]-acetamide;

(S)-N-[[3-[3-Fluoro-4-[1-(methanesulfonyl)-3-(3-methyl)-azetidinyl]-phenyl]-2-oxo-5-oxazolidinyl]methyl]-acetamide;

(S)-N-[[3-[3-Fluoro-4-[1-(benzyloxyacetyl)-3-(3-methyl)-azetidinyl]-phenyl]-2-oxo-5-oxazolidinyl]methyl]-acetamide;

(S)-N-[[3-[3-Fluoro-4-[1-(hydroxyacetyl)-3-(3-methyl)-azetidinyl]-phenyl]-2-oxo-5-oxazolidinyl]methyl]-acetamide.

A second method for preparing compounds of intermediate 1 having a 4 membered heterocycle containing nitrogen, wherein $R_2$ is H, in highly enantiomerically enriched form is depicted in CHART C. The first step involves reaction of structure 18 with a protected aniline 19 in the presence of an appropriate base, such as sec-butyllithium, in an appropriate solvent, such as THF, at a temperature range of −40° C. to −78° C. to afford compounds 20. Reaction of 20 with benzyl chloroformate at 0° C. to 25° C. gives compound 21 which reacts further at 25° C. to 100° C. to give compound 22. Treatment of 22 with excess triethylsilane and trifluoroacetic acid in a suitable solvent such as methylene chloride, at a temperature range of 10° C. to 40° C. gives compound 23. The remaining synthetic steps which lead to structure 17 are similar to the procedures outlined in CHART B.

The following compounds of Formula (I) having a 4-membered heterocycle containing nitrogen, for example, are prepared directly by the methods described in CHART A and CHART C:

(S)-N-[[3-[3-Fluoro-4-[1-(carbobenzyloxy)-3-azetidinyl]phenyl]-2-oxo-5-oxazolidinyl]methyl]-acetamide;

(S)-N-[[3-[3-Fluoro-4-[3-azetidinyl]phenyl]-2-oxo-5-oxazolidinyl]methyl]acetamide;

(S)-N-[[3-[3-Fluoro-4-[1-(methoxycarbonyl)-3-azetidinyl]phenyl]-2-oxo-5-oxazolidinyl]methyl]acetamide;

(S)-N-[[3-[3-Fluoro-4-[1-(formyl)-3-azetidinyl]phenyl]-2-oxo-5-oxazolidinyl]methyl]acetamide.

CHART D depicts a method for preparing compounds of intermediate 1 having a 5-membered heterocycle containing nitrogen. As shown in CHART D, the first step involves the coupling of vinyltributyltin 24 (commercially available) and compound 25. The compound 25 can be prepared according to the procedures described in PCT/US92/08267 and PCT/US93/09589. The coupling occurs in the presence of palladium catalyst to afford compound 26. The reaction is carried out at a high temperature for several hours, e.g., reflux for 5–8 hours. The compound 26 is then treated with a solution of N-benzyl-N-(methoxymethyl)trimethylsilylmethylamine (prepared according to the literature from commercially available material) and trifluoroacetic acid in an appropriate solvent to provide 27. The reaction occurs over several hours, e.g., 8–17 hours. The N-benzyl group of 27 is then removed by catalytic hydrogenation in the presence of a noble metal catalyst, such as palladium on carbon or palladium hydroxide on carbon to afford 28. The compound 28 can be used to prepare the derivative compounds demonstrated in CHART A. Following a similar procedure and making non-critical variations but substituting different vinyl tributylstannyl derivatives for structure 24, a variety of other heterocyclic derivatives of compound 26 can be obtained as illustrated in EXAMPLE 80.

Alternatively, another method for preparing compounds of intermediate 1 having a 5-membered heterocycle containing nitrogen is depicted in CHART E. As shown in CHART E, nucleophilic aromatic substitution of 7 with dimethylmalonate (commercial available) affords the adduct 29. The reaction occurs in an appropriate solvent such as THF, at a temperature in the range of –100° C. to 60° C. The compound 29 is readily alkylated by a reaction known to those skilled in the art to provide nitrile 30. Catalytic reduction of 30 in the presence of a palladium, platinum or nickel catalyst, in an appropriate solvent such as methanol converts both nitro and nitrile to amines with concommittant intramolecular cyclization to afford the lactam 31. The lactam 31 is then decarboxylated to provide 32, which upon reduction with an appropriate reducing agent such as lithium aluminum hydride or borane, in an appropriate solvent such as THF or ether, affords compound 33. The remaining synthetic steps which lead to structure 34 are similar to the procedures outlined in CHART B.

The following compounds of Formula (I) having a 5-membered heterocycle containing nitrogen, for example, are prepared directly by the methods described in CHART A, CHART D and CHART E:
(S)-N-[[3-[3-Fluoro-4-[1-(hydroxyacetyl)-3-pyrrolidinyl] phenyl]-2-oxo-5-oxazolidinyl]methyl]acetamide;
(S)-N-[[3-[3-Fluoro-4-[1-(formyl)-3-pyrrolidinyl]phenyl]-2-oxo-5-oxazolidinyl]methyl]acetamide;
(S)-3-[4-[5-[(Acetylamino)methyl]-2-oxo-3-oxazolidinyl]-2 fluorophenyl]-1-pyrrolidinecarboxylic acid methyl ester.

Following the general procedure depicted in CHART D for the preparation of compound 26 and making non-critical variations but substituting 6-(tributylstannyl)-3,4-dihydro-2H-dihydropyran for structure 24, the following compound is prepared:
(S)-N-[[3-[3-Fluoro-4-(3,4-dihydro-2H-pyran-6-yl)phenyl]-2-oxo-5-oxazolidinyl]methyl]acetamide.

A method for preparing compounds of formula (I) having a 5-membered heterocycle containing a sulfur atom, oxygen atom, sulfone group or sulfoxide group in highly enantiomerically enriched form wherein $R_3$ or $R_4$ is halo is depicted in CHART F. As shown in CHART F, structure 35 (wherein X is O or S) is reacted with a protected aniline 19 in the presence of an appropriate base, such as sec-butyllithium, in an appropriate solvent, such as THF, at a temperature range of –40° C. to –78° C. to afford compounds 36. Reaction of 36 with benzyl chloroformate at 0° C. to 25° C. gives compound 37. The subsequent elimination reaction known to those skilled in the art affords regiosiomers 38 and 39 as a mixture. Following the general procedure outlined in CHART B provides compounds 40 and 41 as a mixture. In the case where X is S, the sulfur group can be oxidized by an appropriate oxidizer such as N-methylmorpholine N-oxide and osmium tetroxide in an appropriate solvent such as mixtures of water and acetone, or by $NaIO_4$ in an appropriate solvent such as mixtures of water and methanol, to provide the corresponding sulfones and sulfoxides, respectively. When it is desirable, the double bond in the heterocycle ring may be reduced by catalytic hydrogenation in the presence of an appropriate catalyst and a suitable solvent. Furthermore, in the case where X is O, SO, or $SO_2$, the regioisomeric mixture of 40 and 41 can be separated by chromatography as illustrated in EXAMPLEs 68 and 69.

The following compounds of Formula (I) having a 5-membered heterocycle containing a sulfur atom, oxygen atom, sulfone group or sulfoxide group, for example, are prepared directly by the method of CHART F:
(S)-(–)-N-[[3-[3-Fluoro-4-(dihydrothien-3-yl)-phenyl]-2-oxo-5-oxazolidinyl]methyl]acetamide;
(5S)-N-[[3-[3-Fluoro-4-(2,5-dihydro-1-oxido-3-thienyl)-phenyl]-2-oxo-5-oxazolidinyl]methyl]acetamide;
(5S)-N-[[3-[3-Fluoro-4-(4,5-dihydro-1-oxido-3-thienyl)-phenyl]-2-oxo-5-oxazolidinyl]methyl]acetamide;
(S)-N-[[3-[3-Fluoro-4-(2,5-dihydro-1,1-dioxido-3-thienyl)-phenyl]-2-oxo-5-oxazolidinyl]methyl]acetamide;
(S)-N-[[3-[3-Fluoro-4-(4,5-dihydro-1,1-dioxido-3-thienyl)-phenyl]-2-oxo-5-oxazolidinyl]methyl]acetamide.

A method for preparing compounds having a 6-membered heterocycle containing a nitrogen atom, sulfur atom, oxygen atom, sulfone group or sulfoxide group wherein $R_1$ and $R_4$ are hydrogen is depicted in CHART G. As shown in CHART G, the first step involves the condensation of structures 42 and 43 (wherein X is O, S, or N) to afford compound 44. In the case where X is a nitrogen atom, the amino group should be protected with an appropriate protecting group such as carbobenzyloxy (CBz). The protecting group is optionally removed after the synthesis to give compounds 46 or 47 (wherein X is NH), which can be used to prepare the derivative compounds demonstrated in CHART A. The reaction of 42 with 43 occurs in an appropriate solvent such as THF, at an appropriate temperature such as –78° C. to –40° C., in the presence of a lithium base such as n-butyllithium. The subsequent elimination reaction known to those skilled in the art provides compound 45. The remaining synthetic steps which lead to the compound 46 are similar to the procedures outlined in CHART B. When it is desirable, the double bond in the heterocyclic ring may be reduced to give 47 by catalytic hydrogenation; and when X is a sulfur atom, the sulfur group can be oxidized to afford the corresponding sulfones and sulfoxides as described above for CHART F.

CHART H depicts a method for preparing compounds having a 6-membered heterocycle wherein substitutes $R_3$ and/or $R_4$ are halo. As shown in CHART H, structure 48 (X is O, S, or NR wherein R is an appropriate protecting group) is reacted with a protected aniline 19 in the presence of an appropriate base, such as sec-butyllithium in an appropriate solvent such as THF at a temperature in the range of –40° C. to –78° C., followed by the addition of zinc chloride and an appropriate catalyst such as tetrakis(triphenylphosphine) palladium with further reaction at reflux to afford compound 49. Optionally, in the case where X is nitrogen, structure 49 can be reduced to the saturated derivatives at this point and carried on, or structure 49 can be acylated by the reaction known to those skilled in the art to provide structure 50. The remaining synthetic steps which lead to compound 51 are similar to the procedures outlined in CHART B. In the case where X is a sulfur atom, the sulfur group of structure 51 can be oxidized to afford the corresponding sulfones and sulfoxides as described above. In addition, where X is O, NR, or SO₂, structure 51 may be reduced to saturated derivatives by catalytic hydrogenation in the presence of an appropriate catalyst and a suitable solvent to provide the saturated derivative 52. As stated above, in the case where X is a nitrogen atom, the amino group is protected during the preparation with an appropriate protecting group. In this case, the preferred protecting group is 1,1-dimethylethyl carbamate (BOC). The protecting group is removed after the synthesis, and the resultant compound can used to prepare the derivative compounds demonstrated in CHART A.

The following compounds of Formula (I) having a 6-membered heterocycle containing a nitrogen atom, sulfur atom, oxygen atom, sulfone group or sulfoxide group, for example, are prepared directly by the methods of CHART A, CHART G, and CHART H:

(S)-(−)-4-[4-[5-[(Acetylamino)methyl]-2-oxo-3-oxazolidinyl]phenyl]-3,6-dihydro-1(2H)-pyridinecarboxylic acid phenylmethyl ester;

(S)-(−)-N-[[2-Oxo-3-[4-(4-piperidinyl)phenyl]-5-oxazolidinyl]methyl]acetamide;

(S)-(−)-N-[[3-[4-[1-[(Benzyloxy)acetyl]-4-piperidinyl]phenyl]-2-oxo-5-oxazolidinyl]methyl]acetamide;

(S)-(−)-N-[[3-[4-[1-(Hydroxyacetyl)-4-piperidinyl]phenyl]-2-oxo-5-oxazolidinyl]methyl]acetamide;

(S)-(−)-N-[[3-[4-[1-[(Benzyloxy)acetyl]-4-piperidinyl]-3-fluorophenyl]-2-oxo-5-oxazolidinyl]methyl]acetamide;

(S)-(−)-N-[[3-[4-[1-(Hydroxyacetyl)-4-piperidinyl]-3-fluorophenyl]-2-oxo-5-oxazolidinyl]methyl]acetamide;

(S)-(−)-N-[[3-[4-[1-[(Benzyloxy)acetyl]-4-piperidinyl]-3,5-difluorophenyl]-2-oxo-5-oxazolidinyl]methyl]acetamide;

(S)-(−)-N-[[3-[4-[1-(Hydroxyacetyl)-4-piperidinyl]-3,5-difluorophenyl]-2-oxo-5-oxazolidinyl]methyl]acetamide;

(S)-(−)-N-[[3-[4-[1-(Indole-2-carbonyl)-4-piperidinyl]-3-fluorophenyl]-2-oxo-5-oxazolidinyl]methyl]acetamide;

(S)-(−)-N-[[3-[4-[1-(Isoxazole-5-carbonyl)-4-piperidinyl]-3-fluorophenyl]-2-oxo-5-oxazolidinyl]methyl]acetamide;

(S)-(−)-N-[[3-[4-[1-(Methylsulfonyl)-4-piperidinyl]-3-fluorophenyl]-2-oxo-5-oxazolidinyl]methyl]acetamide;

(S)-(−)-4-[4-[5-[(Acetylamino)methyl]-2-oxo-3-oxazolidinyl]-2-fluorophenyl]-1-piperidinecarboxylic acid methyl ester;

(S)-(−)-N-[[3-[4-[1-(Cyanomethyl)-4-piperidinyl]-3-fluorophenyl]-2-oxo-5-oxazolidinyl]methyl]acetamide;

(S)-(−)-N-[[3-[4-[1-(2-Fluoroethyl)-4-piperidinyl]-3-fluorophenyl]-2-oxo-5-oxazolidinyl]methyl]acetamide;

(S)-(−)-N-[[3-[4-[1-(Formyl)-4-piperidinyl]-3-fluorophenyl]-2-oxo-5-oxazolidinyl]methyl]acetamide;

(S)-(−)-4-[4-[5-[[(2,2-Dichloroacetyl)amino]methyl]-2-oxo-3-oxazolidinyl]-2-fluorophenyl]-1-piperidinecarboxylic acid 1,1-dimethylethyl ester;

(S)-(−)-2,2-Dichloro-N-[[2-oxo-3-[3-fluoro-4-(4-piperidinyl)phenyl]-5-oxazolidinyl]methyl]acetamide;

(S)-(−)-2,2-Dichloro-N-[[2-oxo-3-[3-fluoro-4-[1-[(acetoxy)acetyl]-4-piperidinyl]phenyl]-5-oxazolidinyl]methyl]acetamide;

(S)-(−)-2,2-Dichloro-N-[[2-oxo-3-[3-fluoro-4-[1-(hydroxyacetyl)-4-piperidinyl]phenyl]-5-oxazolidinyl]methyl]acetamide;

(S)-(−)-N-[[2-Oxo-3-[3-fluoro-4-[1-[(acetoxy)acetyl]-4-piperidinyl]phenyl]-5-oxazolidinyl]methyl]acetamide;

(S)-(−)-N-[[3-[4-(3,6-Dihydro-2H-pyran-yl)-3-fluorophenyl]-2-oxo-5-oxazolidinyl]methyl]acetamide;

(S)-(−)-N-[[3-[4-[Tetrahydro-2H-pyran-4-yl]-3-fluorophenyl]-2-oxo-5-oxazolidinyl]methyl]acetamide;

(S)-(−)-N-[[3-[4-(3,6-Dihydro-2H-thiopyran-4-yl)-3-fluorophenyl]-2-oxo-5-oxazolidinyl]methyl]acetamide;

(S)-(−)-N-[[3-[4-(3,6-Dihydro-2H-thiopyran-4-yl)-3-fluorophenyl]-2-oxo-5-oxazolidinyl]methyl]acetamide S,S-dioxide;

(S)-(−)-N-[[3-[3-Fluoro-4-(tetrahydro-2H-thiopyran-4-yl)phenyl]-2-oxo-5-oxazolidinyl]methyl]acetamide S,S-dioxide;

(S)-(−)-N-[[3-[4-(3,6-Dihydro-2H-pyran-4-yl)phenyl]-2-oxo-5-oxazolidinyl]methyl]acetamide;

(S)-(−)-N-[[3-[4-[Tetrahydro-2H-pyran-4-yl]phenyl]-2-oxo-5-oxazolidinyl]methyl]acetamide;

(S)-(−)-N-[[3-[4-(3,6-Dihydro-2H-thiopyran-4-yl)phenyl]-2-oxo-5-oxazolidinyl]methyl]acetamide;

(S)-(−)-N-[[3-[4-(3,6-Dihydro-2H-thiopyran-4-yl)phenyl]-2-oxo-5-oxazolidinyl]methyl]acetamide S,S-dioxide;

(S)-(−)-N-[[3-[4-(3,6-Dihydro-2H-thiopyran-4-yl)-3-fluorophenyl]-2-oxo-5-oxazolidinyl]methyl]acetamide S-oxide;

(S)-(−)-N-[[3-[4-(3,6-Dihydro-2H-thiopyran-4-yl)phenyl]-2-oxo-5-oxazolidinyl]methyl]acetamide S-oxide;

(S)-(−)-N-[[3-[4-(Tetrahydro-2H-thiopyran-4-yl)phenyl]-2-oxo-5-oxazolidinyl]methyl]acetamide S,S-dioxide;

(S)-(−)-N-[[3-[4-[1-(4-Oxo-2-thiazolinyl)-4-piperidinyl]-3-fluorophenyl]-2-oxo-5-oxazolidinyl]methyl]acetamide;

(S)-(−)-N-[[3-[4-[1-(5-Methyl-1,3,4-thiadiazol-2-yl)-piperidinyl]-3-fluorophenyl]-2-oxo-5-oxazolidinyl]methyl]acetamide.

CHART I depicts a method for preparing compounds of intermediate 1 which have a partially saturated 6-membered heterocycle containing nitrogen in highly enantiomerically enriched form. As shown in CHART I, the first step involves the coupling of structure 53 and structure 54 to provide compounds 55 and 56. The triflate group of structure 53 may be at either side of the double bond, wherein both are readily prepared from the corresponding commercially available ketones. The structure 54 may be prepared according to the procedures described in PCT/US92/08267 and PCT/US93/09589. The reaction occurs over a few days, e.g. 1–5 days in the presence of an appropriate catalyst such as tris (dibenzylideneacetone)dipalladium(O). The amino protecting group of 55 is removed by treatment with iodotimethylsilane and that of 56 is removed by treatment with either trifluoroacetic acid or iodotrimethylsilane to give the corresponding compounds 57 and 58. Compounds 57 and 58 can be used to prepare the derivative compounds demonstrated in CHART A.

Following the general procedure as described above, and making non-critical variations but substituting 7- or 8-membered rings for the 6-membered ring of structure 53, compounds that have a 7- or 8-membered heterocycle containing nitrogen in highly enantiomerically enriched form can be prepared. Their preparations are illustrated in further detail in EXAMPLEs 75 to 79.

The following compounds of Formula (I) for example, are prepared directly by the methods of CHART A and CHART I:

(S)-(−)-N-[[3-[4-[1-(4-Oxo-2-thiazolinyl)-3,6-dihydro-2H-pyridin-5-yl]-3-fluorophenyl]-2-oxo-5-oxazolidinyl]methyl]acetamide;

(S)-(−)-N-[[3-[4-[1-(5-Methyl-1,3,4-thiadiazol-2-yl)-3,6-dihydro-2H-pyridin-4-yl]-3-fluorophenyl]-2-oxo-5-oxazolidinyl]methyl]acetamide;

(S)-(−)-N-[[2-Oxo-3-[4-(3,6-dihydro-2H-pyridin-4-yl)-3-fluorophenyl]-5-oxazolidinyl]methyl]acetamide;

(S)-(−)-N-[[2-Oxo-3-[3-fluoro-4-[1-[(acetoxy)acetyl]-3,6-dihydro-2H-pyridin-4-yl]phenyl]-5-oxazolidinyl]methyl]acetamide;

(S)-(−)-N-[[3-[4-[1-(Hydroxyacetyl)-3,6-dihydro-2H-pyridin-4-yl]-3-fluorophenyl]-2-oxo-5-oxazolidinyl]methyl]acetamide;

(S)-(−)-N-[[3-[4-[1-(Formyl)-3,6-dihydro-2H-pyridin-4-yl]-3-fluorophenyl]-2-oxo-5-oxazolidinyl]methyl]acetamide;

(S)-(−)-4-[4-[5-[(Acetylamino)methyl]-2-oxo-3-oxazolidinyl]-2-fluorophenyl]-3,6-dihydro-1(2H)-pyridinecarboxylic acid methyl ester;

(S)-(−)-N-[[2-Oxo-3-[4-(3,6-dihydro-2H-pyridin-4-yl)phenyl]-5-oxazolidinyl]methyl]acetamide;

(S)-(−)-N-[[2-Oxo-3-[4-[1-[(acetoxy)acetyl]-3,6-dihydro-2H-pyridin-4-yl]phenyl]-5-oxazolidinyl]methyl]acetamide;

(S)-(−)-N-[[3-[4-[1-(Hydroxyacetyl)-3,6-dihydro-2H-pyridin-4-yl]phenyl]-2-oxo-5-oxazolidinyl]methyl]acetamide;

(S)-(−)-N-[[3-[4-[1-(Formyl)-3,6-dihydro-2H-pyridin-4-yl]phenyl]-2-oxo-5-oxazolidinyl]methyl]acetamide;

(S)-(−)-4-[4-[5-[(Acetylamino)methyl]-2-oxo-3-oxazolidinyl]phenyl]-3,6-dihydro-1(2H)-pyridinecarboxylic acid methyl ester;

(S)-N-[[2-Oxo-3-[3-fluoro-4-[1-[(acetoxy)acetyl]-5,6-dihydro-2H-pyridin-3-yl]phenyl]-5-oxazolidinyl]methyl]acetamide;

(S)-N-[[3-[4-[1-(Hydroxyacetyl)-5,6-dihydro-2H-pyridin-3-yl]-3-fluorophenyl]-2-oxo-5-oxazolidinyl]methyl]acetamide;

(S)-N-[[2-Oxo-3-[3-fluoro-4-[1-[(acetoxy)acetyl]-2,3,4,7-tetrahydro-1H-azepin-5-yl]phenyl]-5-oxazolidinyl]methyl]acetamide;

(S)-(−)-N-[[3-[4-[1-(Hydroxyacetyl)-2,3,4,7-tetrahydro-1H-azepin-5-yl]-3-fluorophenyl]-2-oxo-5-oxazolidinyl]methyl]acetamide;

(S)-(−)-N-[[2-Oxo-3-[3-fluoro-4-[1-[(acetoxy)acetyl]-2,3,6,7-tetrahydro-1H-azepin-4-yl]phenyl]-5-oxazolidinyl]methyl]acetamide;

(S)-(−)-N-[[3-[4-[1-(Hydroxyacetyl)-2,3,6,7-tetrahydro-1H-azepin-4-yl]-3-fluorophenyl]-2-oxo-5-oxazolidinyl]methyl]acetamide;

(5S)-(−)-N-[[3-[4-[1-(Hydroxyacetyl)hexahydro-1H-azepin-4-yl]-3-fluorophenyl]-2-oxo-5-oxazolidinyl]methyl]acetamide.

A second method for preparing compounds of intermediate 1 which have a partially saturated 6-membered heterocycle containing nitrogen in highly enantiomerically enriched form is depicted in CHART J. As shown in CHART J, structure 59 is reacted with a protected aniline 19 to afford structure 60. The subsequent acylation reaction provides structure 61 which is treated with an appropriate acid to give a mixture of 62 and 63. The regioisomers can be separated by chromatography as described in EXAMPLEs 72 and 73 and carried on. The protecting groups then are removed by treatement with iodotrimethylsilane to give the desired compounds 64 and 57, which can be used to prepare the derivative compounds demonstrated in CHART A. Use of the 4-keto isomer of structure 59 provides an alternate route to the 4-isomer, structure 58. Alternatively, the hydroxy group of structure 61 or its 4-isomer may be replaced by a fluoro atom using an appropriate agent such as diethylaminosulfur trifluoride in an appropriate solvent such as methylene chloride. The elimination step shown for structure 61 is not conducted in this situation. This replacement reaction is further detailed in EXAMPLE 74.

The following compounds of Formula (I) for example, are prepared directly by the methods of CHART A and CHART J.

(S)-N-[[2-Oxo-3-[3-fluoro-4-[1-[(acetoxy)acetyl]-3,4-dihydro-2H-pyridin-5-yl]phenyl]-5-oxazolidinyl]methyl]acetamide (S)-(−)-N-[[3-[4-[1-(Hydroxyacetyl)-3,4dihydro-2H-pyridin-5-yl]-3-fluorophenyl]-2-oxo-5-oxazolidinyl]methyl]acetamide (S)-(−)-N-[[3-[4-[1-Formyl-4fluoro-4-piperidinyl]-3-fluorophenyl]-2-oxo-5-oxazolidinyl]methyl acetamide.

These compounds are useful for treatment of microbial infections in humans and other warm blooded animals, under both parenteral and oral administration.

The pharmaceutical compositions of this invention may be prepared by combining the compounds of Formula (I) of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound of Formula (I) according to this invention.

The quantity of active component, that is the compound of Formula (I) according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., 2–4 four times per day.

The compounds of Formula (I) according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula (I) or a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucanine, L(+)-lysine and L(+)-arginine to name but a few representative buffering agents. The compound according to Formula (I) generally will be dissolved in the carrier in an amount sufficient to provide a pharmaceutically acceptable injectable concentration in the range of about 1 mg/mL to about 400 mg/mL of solution. The resulting liquid pharmaceutical composition will be administered so as to obtain the above-mentioned antibacterially effective amount of dosage. The compounds of Formula (I) according to this invention are advantageously administered orally in solid and liquid dosage forms.

Antimicrobial activity was tested in vivo using the Murine Assay procedure. Groups of female (six mice of 18–20 grams each) were injected intraperitoneally with bacteria which were thawed just prior to use and suspended in brain heart infusion with 4% brewers yeast (*Staphylococcus aureus*) or brain heart infusion (Streptococcus species). Antibiotic treatment at six dose levels per drug was administered one hour and five hours after infection by either oral intubation or subcutaneous routes. Survival was observed daily for six days. ED50 values based on mortality ratios were calculated using probit analysis. The subject compounds are compared against well-known antimicrobials vancomycin and U-100592 as controls. See "Upjohn Oxazolidinone Antibacterial Agent", posters presented at the 35th Interscience Conference on Antimicrobial Agents and Chemotherapy. The data are shown in Table 1 and Table 2.

TABLE 1

| EXAMPLE No. | $ED_{50}$(mg/kg) | Vancomycin $ED_{50}$(mg/kg) |
|---|---|---|
| 3 | 5.00 | 3.00 |
| 4 | >20.00 | 3.10 |
| 5 | 3.60 | 1.30 |
| 6 | >20.00 | 5.00 |
| 10 | 20.00 | 2.00 |
| 11 | >20.00 | 2.90 |
| 12 | 20.00 | 2.00 |
| 13 | >10.00 | 1.50 |
| 16 | 17.00 | 3.60 |
| 19 | 6.80 | 1.80 |
| 21 | >20.00 | 1.80 |
| 22 | 2.30 | 2.40 |
| 23 | >20.00 | 1.60 |
| 24 | >20.00 | 1.90 |
| 28 | 15.30 | 1.90 |
| 29 | 5.00 | 1.90 |
| 33 | 10.60 | 1.60 |
| 34 | 6.30 | 1.60 |
| 37 | 8.70 | 1.80 |
| 39 | 3.00 | 1.80 |
| 40 | 1.00 | 1.80 |
| 44 | 5.00 | 0.90 |
| 47 | 7.10 | 1.90 |

TABLE 2

| EXAMPLE No. | $ED_{50}$(mg/kg) | U-100592 $ED_{50}$(mg/kg) |
|---|---|---|
| 45 | 2.80 | 2.10 |
| 46 | 7.90 | 2.30 |
| 48 | 17.50 | 2.10 |

TABLE 2-continued

| EXAMPLE No. | $ED_{50}$(mg/kg) | U-100592 $ED_{50}$(mg/kg) |
|---|---|---|
| 49 | 2.40 | 2.10 |
| 50 | 2.20 | 2.90 |
| 51 | 2.80 | 5.20 |
| 52 | 4.00 | 2.30 |
| 53 | >20.00 | 2.30 |
| 54 | 6.60 | 2.90 |
| 55 | 2.30 | 2.50 |
| 56 | 4.40 | 2.70 |
| 57 | 6.20 | 2.70 |
| 59 | 4.2 | 4.40 |
| 60 | 3.1 | 4.40 |
| 61 | 6.10 | 2.70 |
| 62 | 12.0 | 2.40 |
| 63 | 4.90 | 4.60 |
| 64 | 4.60 | 2.90 |
| 67 | 13.3 | 6.0 |
| 68(a) | 3.50 | 3.50 |
| 69(a) | 10.0 | 7.80 |
| 71 | 13.4 | 4.40 |
| 74 | 10.3 | 4.40 |
| 76 | >20 | 3.50 |
| 78 | 6.0 | 3.20 |
| 83 | 7.50 | 4.10 |
| 84 | 6.50 | 4.10 |

In order to more fully illustrate the nature of the invention and the manner of practicing the same, the following experimental examples are presented.

EXAMPLE 1

(S)-N-[[3-[3-Fluoro-4-[1-(carbobenzyloxy)-(3-methyl)-3-azetidinyl]-phenyl]-2-oxo-5-oxazolidinyl] methyl]-acetamide Step 1: Ethyl 1-cyano-1-(4-nitro-2-fluorophenyl)propionate A flame-dried 3-neck 1-L round bottom flask equipped with a magnetic spinbar and addition funnel was charged with 6.40 g sodium hydride (0.160 mol, 60% oil dispersion) followed by washing with pentane (3×40 mL) and drying under house vacuum. The hydride was suspended in 100 mL tetrahydrofuran, cooled to 0° C., and treated with a solution of ethyl cyanoacetate (8.6 mL, 0.080 mol) in 150 mL THF over 15 minutes with gas evolution. The resulting milky solution of enolate was stirred five minutes then treated with a solution of 3,4-difluoronitrobenzene (I) (8.8 mL, 0.080 mol) in 150 mL THF with immediate orange coloration. The cooling bath was removed and the reaction mixture was warmed to 50° C. for 18 hours. The now red suspension was cooled to room temperature and successively treated with 100 g iodomethane (0.72 mol), 33 g potassium carbonate (0.24 mol), and 100 mL acetone. The visually unchanged solution was warmed to 60° C. for an additional 16 hours. The now tan suspension was cooled to room temperature, filtered through a pad of CELITE, and the filtrate was concentrated in vacuo. The resulting residue was diluted with 500 mL water and extracted twice with ethyl acetate (500 mL). The combined organics were washed once with brine (300 mL), dried over $MgSO_4$, filtered, and concentrated to give 21.39 g of a brown oil. This crude material was purified by LC on 850 g (230–400) silica gel eluting with 20% ethyl acetate/hexanes to afford 18.14 g (100%) of the title compound as a yellow oil that spontaneously crystallized. mp 56.0–57.0° C.; $R_f$ 0.34 (20% ethyl acetate/ hexanes); IR (neat) 1752, 1534, 1423, 1355, 1248, 1239, 1213, 1099, 811, 741 $cm^{-1}$; $^1H$ NMR (300 MHz, $CDCl_3$) δ8.16 (m, 1H, aromatic), 8.03 (dd, 1H, J=2.3 Hz, J=10.4 Hz, aromatic), 7.80 (dd, 1H, J=7.6 Hz, J=8.6 Hz, aromatic), 4.33 (m, 2H, O—$CH_2$), 2.04 (s, 3H, $CH_3$), 1.28 (t, 3H, J=7.2 Hz, O—CH$_2$—CH$_3$). HRMS Calcd for C$_{12}$H$_{11}$N$_2$O$_4$F$_1$+H$_1$: 267.0781. Found: 267.0799.

Step 2: Ethyl 1-aminomethyl-1-(4-amino-2-fluorophenyl) propionate

A solution of ethyl 1-cyano-1-(4-nitro-2-fluorophenyl) propionate (17.9 g, 67.3 mmol) in absolute ethanol (500 mL) was treated with Raney-Nickel (30.9 g of a 50% slurry in water) and subjected to hydrogenation in a Parr apparatus for 17 hours (25–30 psi H$_2$, room temperature). The reaction mixture was then filtered through Celite (repeated EtOH washings) and concentrated in vacuo (heat gun, Hi-vac) to give the title compound as a golden syrup (15.6 g, 97%). This material could be purified by chromatography on silica gel using 15% methanol/ethyl acetate but was typically carried on to the next step without further purification: R$_f$ 0.32 (15% MeOH/EtOAc); $^1$H NMR (CDCl$_3$) δ7.00 (t, J=8.5, 1H, aromatic), 6.45 (dd, J=8.2, 2.3, 1H, aromatic), 6.36 (dd, J=13.1, 2.4, aromatic), 4.18 (q, J=7.0, 3H, —CH$_2$CH$_3$), 3.76 (br s, 2H, NH$_2$), 3.06 (dd, J=18.2, 13.8, 2H, CH$_2$N), 1.52 (s, 3H, CCH$_3$), 1.21 (t, J=7.1, 2H, —CH$_2$CH$_3$); IR (liquid) 1722, 1634, 1513, 1445, 1305, 1283, 1243, 1172, 1132, 845 cm$^{-1}$; HRMS: Calcd (C$_{12}$H$_{17}$F$_1$N$_2$O$_2$) 240.1274; Found 240.1293.

Step 3: 3-Methyl-3-(4-amino-2-fluorophenyl)-azetidinone

A solution of ethyl 1-aminomethyl-1-(4-amino-2-fluorophenyl)propionate (2.1 g, 8.7 mmol) in THF (50 mL) was added slowly via syringe to a cold (0° C.) solution of methyl magnesium bromide (15 mL of a 3 M solution in ether, 45 mmol, diluted with 100 mL THF). When addition was complete, the syringe was rinsed with additional THF (2×12 mL). The cooling bath was removed and the beige solution was allowed to stir at room temperature for three hours, at which point it was poured into saturated ammonium chloride (aq, ca. 500 mL) and volatiles were removed in vacuo. The resulting aqueous phase was extracted three times with t-butyl methyl ether and the combined organics were washed once with water, once with brine, dried over MgSO$_4$, filtered, and concentrated to give 1.4 g of a yellow syrup. Extraction of the aqueous phase with ethyl acetate provided an additional 190 mg crude product. The crude products thus obtained were combined and chromatographed on silica gel using 50% ethyl acetate/hexane to give the title compound (1.0 g, 60%) as a pale yellow solid, mp 125–127° C.: R$_f$ 0.21 (50% EtOAc/hexane); $^1$H NMR (CDCl$_3$) δ7.46 (t, J=8.3, 1H, aromatic), 6.43–6.35 (m, 2H, aromatics), 5.77 (br s, 1H, NH), 3.75 (br s, 2H, NH$_2$), 3.54 (dd, J=5.5, 2.4, 1H, CH$_2$), 3.45 (d, J=5.5, 1H, CH$_2$), 1.64 (s, 3H, CH$_3$); IR (mull) 3439, 3342, 3236, 1738, 1635, 1516, 1441, 1210, 1146, 631 cm$^{-1}$; Anal. calcd for C$_{10}$H$_{11}$F$_1$N$_2$O$_2$; C, 61.84, H, 5.71, N, 14.43. Found: C, 62.13, H, 5.81, N, 14.36.

Step 4: 3-(4-Amino-2-fluorophenyl)-3-methylazetidine

A flame-dried 3-neck 2-L round bottom flask equipped with mechanical stirrer, reflux condenser, and addition funnel was charged with 300 mL tetrahydrofuran and 350 mL 1 M lithium aluminumhydride (0.35 mol) followed by cooling to 0° C. This solution was treated with a solution of 9.85 g 3-Methyl-3-(4-amino-2-fluorophenyl)-2-azetidinone (0.051 mol) in 210 mL THF with gas evolution and a yellow coloration. The cooling bath was removed and the reaction was heated to reflux with the rapid formation of a white precipitate. After 20 hours, the visually unchanged reaction mixture was cooled to room temperature and quenched by the successive addition of 13 mL water, 12 mL 5 M sodium hydroxide, and 47 mL water. The resulting thick gelatinous suspension was diluted with one L ethyl acetate, filtered through a pad of CELITE, concentrated, and high vacuum dried to afford 9.82 g of the title compound as a light orange syrup. $^1$H NMR (300 MHz, CDCl$_3$) δ6.78 (t, 1H, J=8.5 Hz, aromatic), 6.37 (m, 2H, aromatic), 4.06 (d, 2H, J=8.2 Hz, N—CH$_{2a}$s), 3.81 (bs, 3H, NHs), 3.58 (d, 2H, J=8.2 Hz, N—CH$_{2b}$s), 1.65 (s, 3H, CH$_3$).

Step 5: N-Carbobenzyloxy-3-(N-carbobenzyloxy-3-fluoroanilin-4-yl)-3-methylazetidine A 500 mL round bottom flask equipped with a magnetic spinbar and addition funnel was charged with 85 mL water, 38.4 g sodium bicarbonate (0.46 mol) and a solution of 9.82 g 3-(4-amino-2-fluorophenyl)-3-methylazetidine (0.051 mol theory) in 165 mL acetone. The resulting orange suspension was cooled to 0° C. and treated with 43 mL benzylchloroformate (0.30 mol) with gas evolution and the reaction turning a light yellow color. The cooling bath was removed and the reaction mixture was stirred at room temperature for 65 hours. TLC indicates incomplete consumption of the starting aminoaniline and an additional 12.8 g sodium bicarbonate (0.15 mol) and 14 mL benzylchloroformate (0.10 mol) was added with additional gas evolution. After two hours, the reaction mixture was diluted with 350 mL saturated sodium bicarbonate and extracted three times with ethyl acetate (300 mL). The combined organics were washed once with water (200 mL), once with brine (200 mL), dried over MgSO$_4$, filtered, and concentrated to give 29.86 g of a light yellow oil. This crude material was purified by LC on 850 g (230–400) silica gel eluting with 25% ethyl acetate/hexanes to afford 11.67 g (51%) of the title compound as a light yellow solid. R$_f$ 0.18 (25% ethyl acetate/hexanes); IR (neat) 1735, 1707, 1693, 1600, 1534, 1455, 1424, 1414, 1221, 1081 cm$^{-1}$; $^1$H NMR (300 MHz, CDCl$_3$) δ7.35 (m, 11H, aromatic), 6.96 (m, 3H, aromatic & NH), 5.19 (s, 2H, Ph-CH$_2$), 5.09 (s, 2H, Ph-CH$_2$), 4.30 (d, 2H, J=8.2 Hz, N—CH$_{2a}$s), 4.00 (d, 2H, J=8.4 Hz, N—CH$_{2b}$s), 1.59 (s, 3H, CH$_3$); $^{13}$C NMR (75 MHz, CDCl$_3$) 160.4 (d, J$_{CF}$=245 Hz), 156.6, 153.0, 138.1 (d, J$_{CF}$=11 Hz), 136.5, 135.7, 128.6, 128.4, 128.2, 127.9, 127.8, 127.5, 127.0, 126.9, 113.9, 106.6 (d, J$_{CF}$=27 Hz), 67.1, 66.6, 60.8, 60.2, 36.1, 28.2; Anal. Calcd for C$_{26}$H$_{25}$N$_2$O$_4$F$_1$: C, 69.63; H, 5.62; N, 6.25. Found: C, 69.37; H, 5.69; N, 5.87.

Step 6: (R)-(−)-N-Carbobenzyloxy-3-methyl-3-[2-fluoro-4-[5-hydroxymethyl-2-oxo-3-oxazolidinyl]phenyl]azetidine A 500 mL round bottom flask containing 11.48 g N-carbobenzyloxy-3-(N-carbobenzyloxy-3-fluoroanilin-4-yl-3-methylazetidine (25.6 mmol) was equipped with a magnetic spinbar, charged with 100 mL tetrahydrofuran (freshly distilled), and cooled to −78° C. This light yellow homogenous solution was treated with 16.6 mL n-butyllithium (26.6 mmol) with a slight darkening in color. The carbamate ion was stirred 30 minutes at this reduced temperature followed by treatment with 3.8 mL R-glycidylbutyrate (26.6 mmol) with no observable change. The cooling bath was removed and the reaction was warmed to room temperature for 16 hours. The now orange opaque solution was diluted with 200 mL saturated ammonium chloride and extracted twice with ethyl acetate (250 mL). The combined organics were washed once with saturated sodium bicarbonate (200 mL), once with brine (300 mL), dried over MgSO$_4$, filtered, and concentrated to give 15.72 g of the title compound as an orange oil. This crude material was purified by LC on 530 g (230–400) silica gel eluting with 80% ethyl acetate/hexanes to afford 6.79 g (64%) of a light yellow amorphous solid. R$_f$ 0.28 (80% ethyl acetate/hexanes); [α]$_D$ −35°(c 0.8967, methanol); IR (neat) 1754, 1708, 1516, 1454, 1429, 1415, 1358, 1228, 1194, 1076 cm$^{-1}$; $^1$H NMR (300 MHz, CDCl$_3$) δ7.44 (dd, 1H, J=2.2 Hz, J=13.0 Hz, aromatic), 7.33 (m, 5H, aromatic), 7.19 (dd, 1H, J=2.2 Hz, J=8.5 Hz, aromatic), 7.03 (t, 1H, J=8.7 Hz, aromatic), 5.09 (S, 2H, Ph-CH$_2$), 4.73 (m, 1H, methine), 4.30 (d, 2H, J=8.2 Hz, Ph-C—CH$_{2a}$S), 3.97 (m, 5H, Ph-C—CH$_{2b}$S, Ph-N—CH$_2$s, HO—CH$_{2a}$), 3.73 (m, 1H, HO—CH$_{2b}$), 2.80 (t, 1H, J=6.3 Hz, HO), 1.60 (s, 3H, CH$_3$); $^{13}$C NMR (75 MHz, CDCl$_3$) 160.2 (d, J$_{CF}$=246 Hz), 156.5, 154.2, 138.0 (d, J$_{CF}$=11 Hz), 136.3, 128.2, 128.1, 127.8, 127.7, 126.9 (d, J$_{CF}$=7 Hz), 113.1 (d, J$_{CF}$=3 Hz), 106.2 (J$_{CF}$=27 Hz), 72.6, 66.5, 62.4, 60.1, 46.0, 35.9, 28.0; Melt solvate=3.8% ethyl acetate; Anal. Calcd for C$_{22}$H$_{23}$N$_2$O$_5$F$_1$ plus 3.8% ethyl acetate: C, 63.41; H, 5.73; N, 6.50. Found: C, 63.15; H, 5.52; N, 6.58. HRMS Calcd for C$_{22}$H$_{23}$N$_2$O$_5$F$_1$: 415.1169. Found: 415.1674.

Step 7: (R)-(-)-N-Carbobenzyloxy-3-methyl-3-[2-fluoro-4-[5-hydroxymethyl-2-oxo-3-oxazolidinyl]phenyl]azetidine methone sulfuride ester A 500 mL round bottom flask containing 6.55 g (R)-(-)-N-carbobenzyloxy-3-methyl-3-[2-fluoro-4-[5-hydroxymethyl-2-oxo-3-oxazolidinyl]phenyl]azetidine (15.3 mmol) was equipped with a magnetic spinbar, charged with 150 mL dichloromethane, and cooled to 0° C. This light yellow homogenous solution was treated successively with 3.2 mL triethylamine (23.0 mmol) and 1.4 mL methanesulfonyl chloride (18.4 mmol) with no observable change. The cooling bath was removed and the reaction mixture was warmed to room temperature for one hour. The visually unchanged solution was diluted with 100 mL 0.5 N hydrochloric acid, shaken, layers separated and the acidic layer extracted once with dichloromethane (100 mL). The combined organics were washed once with brine (75 mL), dried over MgSO$_4$, filtered, and concentrated to give 7.68 g (100%) of the title compound as a light yellow amorphous solid. R$_f$ 0.40 (80% ethyl acetate/hexanes); IR (mull) 1758, 1703, 1516, 1418, 1358, 1337, 1230, 1176, 1075, 965 cm$^{-1}$; $^1$H NMR (300 MHz, CDCl$_3$) δ7.44 (dd, 1H, J=2.2 Hz, J=12.8 Hz, aromatic), 7.33 (m, 5H, aromatic), 7.17 (dd, 1H, J=2.2 Hz, J=8.5 Hz, aromatic), 7.06 (t, 1H, J=8.5 Hz, aromatic), 5.10 (s, 2H, Ph-CH$_2$), 4.92 (m, 1H, methine), 4.50 (dd, 1H, J=3.6 Hz, J=11.7 Hz, MsO—CH$_{23}$), 4.42 (dd, 1H, J=4.1 Hz, J=11.7 Hz, MsO—CH$_{2b}$), 4.31 (d, 2H, J=8.1 Hz, Ph-C—C$_{2a}$s), 4.13 (t, 1H, J=9.2 Hz, Ph-N—CH$_{2a}$), 4.00 (d, 1H, J=8.5 Hz, Ph-C—CH$_{2b}$S), 3.94 (dd, 1H, J=6.2 Hz, J=9.2 Hz, Ph-N—CH$_{2b}$), 3.10 (S, 3H, S—CH$_3$), 1.62 (S, 3H, C—CH$_3$); 13C NMR (75 MHz, CDCl$_3$) 160.3 (d, J$_{CF}$=247 Hz), 156.5, 153.3, 137.6 (d, J$_{CF}$=11 Hz), 136.4, 129.0, 128.8, 128.3, 127.9, 127.8, 127.3, 127.2 (d, J$_{CF}$=6 Hz), 113.3 (d, J$_{CF}$=3 Hz), 106.5 (d, J$_{CF}$=28 Hz), 69.4, 67.8, 66.6, 60.4, 46.2, 37.7, 36.1, 28.1; Anal. Calcd for C$_{23}$H$_5$N$_2$O$_7$F$_1$S$_1$: C, 56.09; H, 5.12; N, 5.69. Found: C, 55.76; H, 5.17; N, 5.61.

Step 8: (R)-(-)-N-Carbobenzyloxy-3-methyl-3-[2-fluoro-4-[5-aminomethyl-2-oxo-3-oxazolidinyl]phenyl]azetidine Two oven-dried 100 mL sealable tubes equipped with magnetic spinbars were equally charged with a solution of 7.50 g (R)-(-)-N-carbobenzyloxy-3-methyl-3-[2-fluoro-4-[5-hydroxymethyl-2-oxo-3-oxazolidinyl]phenyl]azetidine methone sulfuride ester (15.2 mmol) in 75 mL methanol and 75 mL tetrahydrofuran (freshly distilled). These light yellow homogenous solutions were saturated with gaseous ammonia over ten minutes becoming almost colorless, sealed with teflon screwcaps, and heated to 100° C. for 64 hours. The reaction mixtures were combined and concentrated to afford the title compound as a crude yellow foam.

Step 9: (S)-N-[[3-[3-Fluoro-4-[1-(carbobenzyloxy)-(3-methyl)-3-azetidinyl]phenyl]-2-oxo-5-oxazolidinyl]methyl]-acetamide The title compound was prepared as follows: (R)-(-)-N-carbobenzyloxy-3-methyl-3-[2-fluoro-4-[5-aminomethyl-2-oxo-3-oxazolidinyl]phenyl]azetidine was diluted with 220 mL dichloromethane, cooled to 0° C., and successively treated with 3.7 mL pyridine (46 mmol) and 1.8 mL acetic anhydride (19 mmol) with no observable change. The cooling bath was removed and the reaction mixture was warmed to room temperature for 16 hours. The visually unchanged solution was concentrated to a yellow foam, rediluted with 50 mL dichloromethane, and filtered to remove the remaining insoluble precipitate. The filtrate was purified by LC on 340 g (230–400) silica gel eluting with 2.5% methanol/ethyl acetate to afford 5.85 g (84%) of (S)-N-[[3-[3-fluoro-4-[1-(carbobenzyloxy)-(3-methyl)-3-azetidinyl]-phenyl]-2-oxo-5-oxazolidinyl]methyl]-acetamide as a colorless glass. R$_f$ 0.24 (2.5% methanol/ethyl acetate); [α]$_D$ _19°(c 0.9971, methanol); IR (mull) 1754, 1706, 1676, 1516, 1430, 1415, 1357, 1227, 1194, 1075 cm$^{-1}$; $^1$H NMR (300 MHz, CDCl$_3$) δ7.42 (dd, 1H, J=2.1 Hz, J=12.9 Hz, aromatic), 7.33 (m, 5H, aromatic), 7.13 (dd, 1H, J=2.2 Hz, J=8.5 Hz, aromatic), 7.04 (t, 1H, J=8.5 Hz, aromatic), 6.56 (bt, 1H, J=6.2 Hz, NH), 5.10 (s, 2H, Ph-CH$_2$), 4.79 (m, 1H, methine), 4.30 (d, 2H, J=8.2 Hz, Ph-C—CH$_2$ as), 4.01 (m, 3H, Ph-C—CH$_{2b}$s, Ph-N—CH$_{2a}$), 3.78 (dd, 1H, J=6.7 Hz, J=9.1 Hz, Ph-N—CH$_{2b}$), 3.64 (m, 2H, NH—CH$_2$s), 2.02 (s, 3H, O═C—CH$_3$), 1.60, (s, 3H, Ph-C—CH$_3$); $^{13}$C NMR (75 MHz, CDCl$_3$) 171.2, 160.3 (d, J$_{CF}$=246 Hz), 156.6, 154.2, 137.9 (d, J$_{CF}$=11 Hz), 136.5, 128.9 (d, J$_{CF}$=14 Hz), 128.4, 127.9, 127.2 (d, J$_{CF}$=7 Hz), 113.2 (d, J$_{CF}$=2 Hz), 106.4 (d, J$_{CF}$=28 Hz), 72.0, 66.6, 60.7, 60.3, 47.3, 41.7, 36.1, 28.1, 22.9; Anal. Calcd for C$_{24}$H$_{26}$N$_3$O$_5$F$_1$: C, 63.29; H, 5.75; N, 9.23. Found: C, 62.98; H, 5.96; N, 8.98.

EXAMPLE 2

(S)-N-[[3-[3-Fluoro-4-[3-methyl-3-azetidinyl]-phenyl]-2-oxo-5-oxazolidinyl]methyl]-acetamide A 500 mL Parr flask was charged with a solution of 5.83 g (S)-N-[[3-[3-fluoro-4-[1-(carbobenzyloxy)-(3-methyl)-3-azetidinyl]-phenyl]-2-oxo-5-oxazolidinyl]methyl]acetamide (12.8 mmol) in 100 mL methanol and 1.17 g 10% palladium on carbon. The black suspension was placed under 40 psi hydrogen with shaking for four hours with the pressure remaining constant at 28 psi. The Parr was removed from the hydrogenator, the reaction mixture was filtered through a pad of CELITE, and concentrated to afford 4.05 g (99%) of an off-white amorphous solid. A 1.00 g portion of this material was purified by LC on 100 g (230–400) silica gel eluting with 2:17:83 NH$_4$OH/methanol/dichloromethane to afford 776 mg of the title compound as a colorless glass. R$_f$ 0.26 (2:17:83 NH$_4$OH/methanol/dichloromethane); [α]$_D$ -23°(c 0.9015, methanol); IR (mull) 1752, 1662, 1630, 1554, 1515, 1483, 1435, 1412, 1227, 1194 cm$^{-1}$; $^1$H NMR (300 MHz, CDCl$_3$) δ7.37 (dd, 1H, J=2.2 Hz, J=12.8 Hz, aromatic), 7.12 (dd, 1H, J=2.2 Hz, J=8.5 Hz, aromatic), 6.99 (t, 1H, J=8.6 Hz, aromatic), 6.33 (bt, 1H, J=6 Hz, O═C—NH), 4.78 (m, 1H, methine), 4.04 (m, 3H, Ph-C—CH$_2$ as, Ph-N—CH$_{2a}$), 3.78 (dd, 1H, J=6.8 Hz, J=9.1 Hz, Ph-N—CH$_{2b}$), 3.66 (m, 2H, NH—CH$_2$s), 3.56 (d, 2H, J=7.8 Hz, Ph-C—CH$_{2b}$s), 2.40 (bs, 1H, NH), 2.02 (s, 3H, O═C—CH$_3$), 1.67 (s, 3H, Ph-C—CH$_3$); $^{13}$C NMR (75 MHz, CDCl$_3$) 171.2, 160.0 (d, J$_{CF}$=246 Hz), 154.2, 137.3 (d, J$_{CF}$=11 Hz), 130.8 (d, J$_{CF}$=15 Hz), 126.9 (d, J$_{CF}$=7 Hz), 113.2, 106.3 (d, J$_{CF}$=27 Hz), 71.9, 58.0, 47.3, 41.7, 40.5, 27.3, 22.9; K.F. Water=0.89%; Anal. Calcd for C$_{16}$H$_{20}$N$_3$O$_3$F$_1$ with 0.89% water: C, 59.27; H, 6.32; N, 12.96. Found: C, 59.07; H, 6.45; N, 12.89. HRMS Calcd for C$_{16}$H$_{20}$N$_3$O$_3$+H$_1$: 322.1567. Found: 322.1569.

EXAMPLE 3

(S)-N-[[3-[3-Fluoro-4-[1-(methoxycarbonyl)-3-(3-methylazetidinyl]-phenyl]-2-oxo-5-oxazolidinyl]methyl]-acetamide An oven-dried 25 mL round bottom flask equipped with magnetic spinbar was charged with 241 mg (S)-N-[[3-[3- fluoro-4-[3-methyl-3-azetidinyl]-phenyl]-2-oxo-5-oxazolidinyl]methyl]-acetamide (0.75 mmol), 8 mL dichloromethane, and cooled to 0° C. The colorless but slightly opaque solution was treated with 0.16 mL triethylamine (1.1 mmol) and 70 μL methylchloroformate (0.90 mmol) with the reaction mixture becoming clear. The cooling bath was removed and the reaction mixture was warmed to room temperature over two hours. The visually unchanged solution was diluted with 30 mL dichloromethane, washed once with water (20 mL), once with brine (15 mL), dried over $MgSO_4$, filtered, and concentrated to give 267 mg of a white foam. This crude material was purified by LC on 18 g (230–400) silica gel eluting with 5% methanol/dichloromethane to afford 219 mg (77%) of the title compound as a white foam. $R_f$ 0.30 (5% methanol/dichloromethane); $[\alpha]_D$ -21°(c 1.0194, methanol); IR (mull) 1755, 1706, 1676, 1631, 1517, 1394, 1227, 1208, 1195, 1076 $cm^{-1}$; $^1H$ NMR (300 MHz, $CDCl_3$) δ7.43 (dd, 1H, J=2.2 Hz, J=12.9 Hz, aromatic), 7.14 (dd, 1H, J=2.2 Hz, J=8.5 Hz, aromatic), 7.05 (t, 1H, J=8.6 Hz, aromatic), 6.35 (bt, 1H, J=6 Hz, NH), 4.80 (m, 1H, methine), 4.28 (d, 2H, J=8.2 Hz, $CO_2$-N—$CH_{2a}$s), 4.04 (t, 1H, J=9.0 Hz, Ph-N—$CH_{2a}$), 3.97 (d, 2H, J=8.4 Hz, $CO_2$—N—$CH_{2b}$S), 3.77 (dd, 1H, J=6.7 Hz, J=9.1 Hz, Ph-N—$CH_{2b}$), 3.68 (m, 5H, NH—$CH_2$s, $OCH_3$), 2.03 (s, 3H, O=C—$CH_3$), 1.61 (s, 3H, Ph-C—$CH_3$); $^{13}C$ NMR (75 MHz, $CDCl_3$) 170.9, 160.2 (d, $J_{CF}$=246 Hz), 157.1, 154.0, 137.8 (d, $J_{CF}$=11 Hz), 128.5 (d, $J_{CF}$=15 Hz), 127.0 (d, $J_{CF}$=7 Hz), 113.1 (d, $J_{CF}$=3 Hz), 106.3 (d, $J_{CF}$=27 Hz), 71.8, 60.4, 52.1, 47.2, 41.7, 35.9, 28.0, 22.9; K.F. Water=1.19%; Anal. Calcd for $C_{18}H_{22}N_3O_5F_1$ plus 1.19% water: C, 56.31; H, 5.91; N, 10.94. Found: C, 56.27; H, 5.93; N, 10.93.

EXAMPLE 4

(S)-N-[[3-[3-Fluoro-4-[1-(methoxyacetyl)-3-(3-methyl)-azetidinyl]phenyl]-2-oxo-5-oxazolidinyl]methyl]-acetamide An oven-dried 25 mL round bottom flask equipped with magnetic spinbar was charged with 241 mg (S)-N-[[3-[3-fluoro-4-[3-methyl-3-azetidinyl]-phenyl]-2-oxo-5-oxazolidinyl]methyl]-acetamide (0.75 mmol), 8 mL dichloromethane, and cooled to 0° C. The colorless but slightly opaque solution was treated with 0.16 mL triethylamine (1.1 mmol) and 85 μL methoxyacetylchloride (0.90 mmol) with a smokey/haze developing. The cooling bath was removed and the reaction mixture was warmed to room temperatue over two hours. The now clear colorless solution was diluted with 25 mL dichloromethane, washed once with water (15 mL), once with brine (15 mL), dried over $MgSO_4$, filtered, and concentrated to give 294 mg of a white foam. This crude material was purified by LC on 27 g (230–400) silica gel eluting with 7% methanol/dichloromethane to afford 240 mg (81%) the title compound as a white amorphous solid. $R_f$ 0.23 (7% methanol/dichloromethane); $[\alpha]_D$ -20°(c 0.9736, methanol); IR (mull) 1754, 1662, 1654, 1632, 1517, 1437, 1412, 1226, 1194, 1122 $cm^{-1}$; $^1H$ NMR (300 MHz, $CDCl_3$) δ7.45 (dd, 1H, J=2.1 Hz, J=13.0 Hz, aromatic), 7.15 (dd, 1H, J=2.1 Hz, J=8.5 Hz, aromatic), 7.07 (t, 1H, J=8.5 Hz, aromatic), 6.47 (bt, 1H, J=6 Hz, NH), 4.80 (m, 1H, methine), 4.51 (d, 1H, J=9.0 Hz, Ph-C—$CH_{2a}$), 4.35 (d, 1H, J=9.7 Hz, Ph-C—$CH_{2b}$), 4.25 (d, 1H, J=9.2 Hz, Ph-C—$CH_{2a}$), 4.05 (m, 4H, O—C—$CH_2$S, Ph-C—$CH_{2b}$, Ph-N—$CH_{2a}$), 3.66 (m, 1H, Ph-N—$CH_{2b}$), 3.66 (m, 2H, NH—$CH_2$s), 2.03 (s, 3H, O=C—$CH_3$), 1.63 (s, 3H, Ph-C—$CH_3$); $^{13}C$ NMR (75 MHz, $CDCl_3$) 171.2, 169.7, 160.4 (d, $J_{CF}$=246 Hz), 154.2, 138.2 (d, $J_{CF}$=11 Hz), 128.4 (d, $J_{CF}$=14 Hz), 127.3 (d, $J_{CF}$=6 Hz), 113.4, 106.6 (d, $J_{CF}$=28 Hz), 72.1, 71.5, 62.4, 59.5, 59.2, 47.5, 41.9, 36.9, 28.3, 23.1; K.F. Water=2.03%; Anal. Calcd for $C_{19}H_2N_3O_5F_1$ plus 2.03% water: C, 56.83; H, 6.25; N, 10.47. Found: C, 56.99; H, 6.34; N, 10.49. HRMS Calcd for $C_{19}H_{24}N_3O_5F_1$: 394.1778. Found: 394.1784.

EXAMPLE 5

(S)-N-[[3-[3-Fluoro-4-[1-(formyl)-3-(3-methyl)-azetidinyl]-phenyl]-2-oxo-5-oxazolidinyl]methyl]-acetamide An oven-dried 25 mL round bottom flask equipped with magnetic spinbar was charged with 241 mg (S)-N-[[3-[3-Fluoro-4-[3-methyl-3-azetidinyl]-phenyl]-2-oxo-5-oxazolidinyl]methyl]-acetamide (0.75 mmol), 8 mL dichloromethane, and cooled to 0° C. The colorless but slightly opaque solution was treated with 0.16 mL triethylamine (1.1 mmol) and 73 μL ethyl formate (0.90 mmol) with no observable change. The cooling bath was removed and the reaction mixture was warmed to room temperature for 16 hours. TLC analysis of the now clear solution indicated incomplete consumption of (S)-N-[[3-[3-Fluoro-4-[3-methyl-3-azetidinyl]-phenyl]-2-oxo-5-oxazolidinyl]methyl]-acetamide. The reaction mixture was treated with an additional 0.14 mL ethyl formate (1.8 mmol) and 8.0 mL 1 N sodium hydroxide with vigorous stirring for five minutes. The reaction was diluted with 10 mL water and extracted twice with dichloromethane (25 mL). The combined organics were washed once with water (20 mL), once with brine (20 mL), dried over $MgSO_4$, filtered, and concentrated to give 253 mg of a white foam. This crude material was purified by LC on 18 g (230–400) silica gel eluting with 6% methanol/dichloromethane to afford 145 mg (55%) the title compound as a white amorphous solid. $R_f$ 0.25 (7% methanol/dichloromethane); $[\alpha]_D$ -20°(c 0.9949, methanol); IR (mull) 1754, 1666, 1631, 1548, 1516, 1478, 1433, 1414, 1227, 1195 $cm^{-1}$; $^1H$ NMR (300 MHz, $CDCl_3$) δ8.06 (s, 1H, CHO), 7.47 (dd, 1H, J=2.0 Hz, J=13.0 Hz, aromatic), 7.16 (dd, 1H, J=2.2 Hz, J=8.5 Hz, aromatic), 7.07 (t, 1H, J=8.6 Hz, aromatic), 6.33 (bt, 1H, J=6 Hz, NH), 4.80 (m, 1H, methine), 4.42 (d, 1H, J=8.2 Hz, Ph-C—$C_{2a}$), 4.30 (d, 1H, J=9.9 Hz, Ph-C—$CH_{2b}$), 4.15 (d, 1H, J=8.3 Hz, Ph-C—$CH_{2a}$), 4.05 (m, 2H, Ph-C—$CH_{2b}$, Ph-N—CF), 3.79 (dd, 1H, J=6.8 Hz, J=9.1 Hz, Ph-N—$CH_{2b}$), 3.67 (m, 2H, NH—$CH_2$s), 2.03 (s, 3H, O=C—$CH_3$), 1.64 (s, 3H, Ph-C—$CH_3$); $^{13}C$ NMR (75 MHz, $CDCl_3$) 171.1, 162.3, 160.3 (d, $J_{CF}$=246 Hz), 154.1, 138.2 (d, $J_{CF}$=11 Hz), 127.9 (d, $J_{CF}$=14 Hz), 127.1 (d, $J_{CF}$=6 Hz), 113.3, 106.4 (d, $J_{CF}$=27 Hz), 71.9, 59.6, 58.2, 47.3, 41.7, 37.6, 28.0, 23.0; HRMS Calcd for $C_{17}H_{20}N_3O_4F_1$: 349.1438. Found: 349.1444.

EXAMPLE 6

(S)-N-[[3-[3-Fluoro-4-[1-(dichloroacetyl)-3-(3-methyl)-azetidinyl]phenyl]-2-oxo-5-oxazolidinyl]methyl]-acetamide An oven-dried 25 mL round bottom flask equipped with magnetic spinbar was charged with 241 mg (S)-N-[[3-[3-Fluoro-4-[3-methyl-3-azetidinyl]-phenyl]-2-oxo-5-oxazolidinyl]methyl]-acetamide (0.75 mmol), 8 mL dichloromethane, and cooled to 0° C. The colorless but slightly opaque solution was treated with 0.16 mL triethylamine (1.1 mmol) and 87 μL dichloroacetyl chloride (0.90 mmol) with a smokey/haze developing. The cooling bath was removed and the reaction mixture was warmed to room temperature over three hours. The now clear colorless solution was diluted with 15 mL water and extracted twice with dichloromethane (25 mL). The combined organics were washed once with brine (15 mL), dried over $MgSO_4$, filtered, and concentrated to give 353 mg of a tan foam. This crude material was purified by LC on 25 g (230–400) silica gel eluting with 5% methanol/dichloromethane to afford 243 mg (75%) the title compound as an off-white amorphous solid. $R_f$ 0.26 (5% methanol/dichloromethane); $[\alpha]_D$ –18°(c 0.9862, methanol); IR (mull) 1752, 1666, 1631, 1545, 1517, 1440, 1412, 1288, 1227, 1193 cm$^{-1}$; $^1$H NMR (300 MHz, CDCl$_3$) δ7.48 (dd, 1H, J=2.1 Hz, J=13.0 Hz, aromatic), 7.18 (dd, 1H, J=2.2 Hz, J=8.5 Hz, aromatic), 7.08 (t, 1H, J=8.6 Hz, aromatic), 6.52 (bt, 1H, J=6.1 Hz, NH), 4.81 (m, 1H, methine), 4.70 (d, 1H, J=8.9 Hz, Ph-C—CH$_2$,), 4.48 (d, 1H, J=9.1 Hz, Ph-C—CH$_{2,\ 4.41}$ (d, 1H, J=10.1 Hz, Ph-C—CH$_2$ a), 4.13 (d, 1H, J=10.0 Hz, Ph-C—CH$_{2b}$), 4.06 (t, 1H, J=9.0 Hz, Ph-N—CH$_{2a}$), 3.79 (dd, 1H, J 6.7 Hz, J=9.1 Hz, Ph-N—CH$_{2b}$), 3.67 (m, 2H, NH—CH$_2$S), 2.03 (s, 3H, O═C—CH$_3$), 1.67 (s, 3H, Ph-C—CH$_3$); $^{13}$C NMR (75 MHz, CDCl$_3$) 171.3, 163.1, 160.3 (d, J$_{CF}$=246 Hz), 154.2, 138.4 (d, J$_{CF}$=11 Hz), 127.6 (d, J$_{CF}$=15 Hz), 127.1 (d, J$_{CF}$=6 Hz), 113.4, 106.6 (d, J$_{CF}$=27 Hz), 72.1, 64.6, 63.1, 60.3, 47.4, 41.8, 36.9, 28.2, 23.0; K.F. Water=1.3%. Anal. Calcd for $C_{18}H_{20}N_3O_4F_1Cl_2$ plus 1.3% water: C, 49.36; H, 4.75; N, 9.60. Found: C, 48.97; H, 4.80; N, 9.53. HRMS Calcd for $C_{18}H_{20}N_3O_4F_1Cl_2$: 432.0893. Found: 432.0900.

EXAMPLE 7

(S)-N-[[3-[3-Fluoro-4-[1-(3-methoxypropionyl)-3-(3-methyl)-azetidinyl]-phenyl]-2-oxo-5-oxazolidinyl]methyl]-acetamide An oven-dried 10 mL round bottom flask equipped with magnetic spinbar was charged with 241 mg (S)-N-[[3-[3-fluoro-4-[3-methyl-3-azetidinyl]-phenyl]-2-oxo-5-oxazolidinyl]methyl]-acetamide (0.75 mmol), 4 mL dichloromethane, 81 μL 3-methoxypropionic acid (0.83 mmol), 0.13 mL of distilled diethylcyanophosphonate (0.83 mmol) and cooled to 0° C. The colorless solution was treated with 0.11 mL triethylamine (0.78 mmol) becoming a pinkish color. The cooling bath was removed and the reaction mixture was warmed to room temperature over 66 hours. The now reddish brown solution was diluted with 20 mL dichloromethane and washed once with water (15 mL), once with brine (15 mL), dried over MgSO$_4$, filtered, and concentrated to give 297 mg of a red foam. This crude material was purified by LC on 18 g (230–400) silica gel eluting with 7% methanol/dichloromethane to afford 216 mg of an off-white amorphous solid. $^1$H NMR indicates this material to be contaminated with 10% (S)-N-[[3-[3-fluoro-4-[1-(formyl)-3-(3-methyl)-azetidinyl]-phenyl]-2-oxo-5-oxazolidinyl]methyl]-acetamide which was removed by catalytic hydrogenolysis with 22 mg 10% palladium on carbon in 30 mL tetrahydrofuran containing 10 drops concentrated hydrochloric acid. The resulting crude material was rechromatographed on 13 g (230–400) silica gel eluting with 7% methanol/dichloromethane to afford 135 mg (44% overall) the title compound as an off-white amorphous solid. $R_f$ 0.23 (7% methanol/dichloromethane); $[\alpha]_D$ –19°(c 0.8324, methanol); IR (mull) 1755, 1644, 1630, 1548, 1516, 1440, 1410, 1226, 1192, 1115 cm$^{-1}$; $^1$H NMR (300 MHz, CDCl$_3$) δ7.45 (dd, 1H, J=2.0 Hz, J=12.9Hz, aromatic), 7.15 (dd, 1H, J=2.2 Hz, J=8.5 Hz, aromatic), 7.07 (t, 1H, J=8.5 Hz, aromatic), 6.29 (bt, 1H, J=6 Hz, NH), 4.80 (m, 1H, methine), 4.42 (d, 1H, J=8.0, Ph-C—C$_{2a}$), 4.30 (d, 1H, J=9.6 Hz, Ph-C—CH$_{2b}$), 4.15 (d, 1H, J=8.2 Hz, Ph-C—CH$_{2a}$), 4.04 (m, 2H, Ph-C—CH$_{2b}$, Ph-N—CH$_{2a}$), 3.79 (dd, 1H, J=6.7 Hz, J=9.1 Hz, Ph-N—CH$_{2b}$), 3.67 (m, 4H, NH—CH$_2$S, O—CH$_2$S), 3.34 (s, 3H, OCH$_3$), 2.36 (qrt, 2H, J=6.2 Hz, O—(CH$_2$)—CH$_2$S), 2.03 (s, 3H, O═C—CH$_3$), 1.61 (s, 3H, Ph-C—CH$_3$); $^{13}$C NMR (75 MHz, CDCl$_3$) 171.5, 171.1, 162.5 (d, J$_{CF}$=246 Hz), 154.2, 138.1 (d, J$_{CF}$=11 Hz), 128.5 (d, J$_{CF}$=15 Hz), 127.3 (d, J$_{CF}$=6 Hz), 113.4, 106.5 (d, J$_{CF}$=28 Hz), 72.0, 68.4, 61.6, 58.9, 47.5, 41.9, 35.6, 32.2, 28.6, 23.1; HRMS Calcd for $C_{20}H_{26}N_3O_5F_1$: 407.1856. Found: 407.1855.

EXAMPLE 8

(S)-N-[[3-[3-Fluoro-4-[1-(3-hydroxypronionyl)-3-(3-methyl)-azetidinyl]-phenyl]-2-oxo-5-oxazolidinyl] methyl]-acetamide A 10 mL recovery flask equipped with magnetic stirrer was charged with 241 mg (S)-N-[[3-[3-fluoro-4-[3-methyl-3-azetidinyl]-phenyl]-2-oxo-5-oxazolidinyl]methyl]-acetamide (0.75 mmol) and 1.5 mL water then cooled to 0° C. The colorless but slightly opaque solution was treated with 52 μL β-propiolactone (0.75 mmol) with no observable change. The cooling bath was removed and the reaction mixture was warmed to room temperature for two hours. The visually unchanged reaction mixture was diluted with 10 mL brine and extracted twice with dichloromethane (20 mL). The combined organics were dried over MgSO$_4$, filtered, and concentrated to give 232 mg of an off-white foam. This crude material was purified by LC on 17 g (230–400) silica gel eluting with 7% methanol/dichloromethane to afford 178 mg (60%) the title compound as a white amorphous solid. $R_f$ 0.30 (10% methanol/dichloromethane); $[\alpha]_D$ –19°(c 0.9248, methanol); IR (mull) 3288, 1754, 1630, 1554, 1517, 1436, 1412, 1289, 1227, 1193 cm$^{-1}$; $^1$H NMR (300 MHz, CDCl$_3$) δ7.46 (dd, 1H, J=2.1 Hz, J=13.0 Hz, aromatic), 7.14 (dd, 1H, J=2.2 Hz, J=8.5 Hz, aromatic), 7.07 (t, 1H, J=8.6 Hz, aromatic), 6.55 (bt, 1H, J=6 Hz, NH), 4.81 (m, 1H, methine), 4.41 (d, 1H, J=8.3, Ph-C—CH$_2$ a), 4.32 (d, 1H, J=9.6 Hz, Ph-C—CH$_{2b}$), 4.12 (d, 1H, J=8.4 Hz, Ph-C—CH$_{2a}$), 4.05 (m, 2H, Ph-C—CH$_{2b}$, Ph-N—CH$_{2a}$), 3.88 (bs, 2H, HO—CH$_2$s), 3.80 (dd, 1H, J=6.8 Hz, J=9.1 Hz, Ph-N—CH$_{2b}$), 3.67 (m, 2H, NH-CH$_2$S), 3.46 (bs, 1H, HO), 2.37 (qrt, 2H, J=5.6 Hz, HO—(CH$_2$)—CH$_2$S), 2.03 (s, 3H, O═C—CH$_3$), 1.63 (s, 3H, Ph-C—CH$_3$); $^{13}$C NMR (75 MHz, CDCl$_3$) 172.8, 171.2, 160.3 (d, J$_{CF}$=246 Hz), 154.1, 138.1 (d, J$_{CF}$=11 Hz), 128.0 (d, J$_{CF}$=14 Hz), 127.1 (d, J$_{CF}$=6 Hz), 113.3, 106.5 (d, J$_{CF}$=27 Hz), 72.0, 61.4, 58.8, 58.3, 47.3, 41.8, 35.7, 32.9, 28.2, 23.0; HRMS Calcd for $C_{19}H_{24}N_3O_5F_1$: 394.1778. Found: 394.1788.

EXAMPLE 9

(S)-N-[[3-[3-Fluoro-4-[1-(4-oxopentanoyl)-3-(3-methyl)-azetidinyl]-phenyl]-2-oxo-5-oxazolidinyl] methyl]-acetamide An oven-dried 10 mL round bottom flask equipped with magnetic spinbar was charged with 241 mg (S)-N-[[3-[3-fluoro-4-[3-methyl-3-azetidinyl]-phenyl]-2-oxo-5-oxazolidinyl]methyl]-acetamide (0.75 mmol), 4 mL dichloromethane, 100 μL levulinic acid (0.98 mmol), 216 mg EDC•HCL (1.13 mmol), 18 mg dimethylamino pyridine (0.15 mmol) and cooled to 0° C. The colorless solution was treated with 0.31 mL triethylamine (2.25 mmol) becoming a pale yellow color. The cooling bath was removed and the reaction mixture was warmed to room temperature over 16 hours. The visually unchanged solution was diluted with 20 mL water and extracted twice with dichloromethane (25 mL). The combined organics were washed once with saturated sodium bicarbonate (20 mL), brine (15 mL), dried over MgSO$_4$, filtered, and concentrated to give 332 mg of a light yellow syrup. This crude material was purified by LC on 20 g (230–400) silica gel eluting with 5% methanol/ dichloromethane to afford 256 mg of an off-white amorphous solid. $^1$H NMR indicates this material to be contaminated with 8% (S)-N-[[3-[3-fluoro-4-[1-(formyl)-3-(3-methyl)-azetidinyl]phenyl]-2-oxo-5-oxazolidinyl]methyl]-acetamide which was removed by catalytic hydrogenolysis with 26 mg 10% palladium on carbon in 30 mL tetrahydrofuran containing ten drops concentrated hydrochloric acid. The resulting crude material was rechromatographed on 15 g (230–400) silica gel eluting with 5% methanol/ dichloromethane to afford 116 mg (37% overall) the title compound as a white amorphous solid. R$_f$ 0.16 (5% methanol/dichloromethane); [α]$_D$ −19°(c 0.9205, methanol); IR (mull) 1754, 1716, 1631, 1548, 1517, 1440, 1411, 1227, 1193, 1166 cm$^{-1}$; $^1$H NMR (300 MHz, CDCl$_3$) δ7.46 (dd, 1H, J=2.1 Hz, J=13.0 Hz, aromatic), 7.15 (dd, 1H, J=2.2 Hz, J=8.5 Hz, aromatic), 7.07 (t, 1H, J=8.5 Hz, aromatic), 6.32 (bt, 1H, J=6 Hz, NH), 4.80 (m, 1H, methine), 4.46 (d, 1H, J=8.1, Ph-C—CH$_{2a}$), 4.27 (d, 1H, J=9.4 Hz, Ph-C—CH$_{2b}$), 4.19 (d, 1H, J=8.3 Hz, Ph-C—CH$_2$ a), 4.01 (m, 2H, Ph-C—CH$_{2b}$, Ph-N—CH$_{2a}$), 3.79 (dd, 1H, J=6.8 Hz, J=9.1 Hz, Ph-N—CH$_{2b}$), 3.68 (m, 2H, NH—CH$_2$s), 2.80 (t, 2H, J=6.5 Hz, CH$_3$CO—CH$_2$s), 2.35 (m, 2H, N—CO—CH$_2$), 2.19 (s, 3H, (CH$_2$)—CO—CH.), 2.03 (s, 3H, NCO—CH$_3$), 1.63 (s, 3H, Ph-C—CH$_3$); $^{13}$C NMR (75 MHz, CDCl$_3$) 207.3, 172.0, 170.9, 160.5 (d, J$_{CF}$=246 Hz), 153.9, 137.8 (d, J$_{CF}$=11 Hz), 128.2 (d, J$_{CF}$=14 Hz), 127.0 (d, J$_{CF}$=6 Hz), 113.1, 106.2 (d, J$_{CF}$=28 Hz), 71.7, 61.3, 58.6, 47.1, 41.6, 37.6, 35.5, 29.7, 28.0, 24.6, 22.8; K.F. Water= 1.67%. Anal. Calcd for C$_{21}$H$_{26}$N$_3$O$_5$F$_1$ plus 1.67% water: C, 59.13; H, 6.33; N, 9.85. Found: C, 59.04; H, 6.38; N, 9.80. HRMS Calcd for C$_{21}$H$_{26}$N$_3$O$_5$F$_1$: 419.1856. Found: 419.1854.

EXAMPLE 10

(S)-N-[[3-[3-Fluoro-4-[1-acetyl-3-(3-methyl)-azetidinyl]-phenyl]-2-oxo-5-oxazolidinyl]methyl]-acetamide An oven-dried 25 mL round bottom flask equipped with magnetic spinbar was charged with 75 mg (S)-N-[[3-[3-fluoro-4-[3-methyl-3-azetidinyl]-phenyl]-2-oxo-5-oxazolidinyl]methyl]-acetamide (0.23 mmol), 5 mL dichloromethane, and cooled to 0° C. The colorless but slightly opaque solution was treated with 49 μL triethylamine (0.35 mmol) and 20 μL acetyl chloride (0.28 mmol) becoming a light yellow color. The cooling bath was removed and the reaction mixture was warmed to room temperature over three hours. The now clear yellow solution was diluted with 10 mL water and extracted twice with dichloromethane (20 mL). The combined organics were washed once with brine (15 mL), dried over MgSO$_4$, filtered, and concentrated to give 96 mg of an off-white foam. This crude material was combined with 28900-RLH-017 and purified by LC on 10 g (230–400) silica gel eluting with 7% methanol/dichloromethane to afford 143 mg the title compound as a white amorphous solid. R$_f$ 0.24 (7% methanol/dichloromethane); [α]$_D$ −21°(c 0.9238, methanol); IR (mull) 1754, 1646, 1631, 1552, 1517, 1435, 1413, 1288, 1227, 1193 cm$^{-1}$; $^1$H NMR (300 MHz, CDCl$_3$) δ7.46 (dd, 1H, J=2.1 Hz, J=13.1 Hz, aromatic), 7.14 (dd, 1H, J=2.2 Hz, J=8.6 Hz, aromatic), 7.07 (t, 1H, J=8.5 Hz, aromatic), 6.40 (bt, 1H, J=6 Hz, NH), 4.80 (m, 1H, methine), 4.39 (d, 1H, J=7.9 Hz, Ph-C—CH$_{2a}$), 4.30 (d, 1H, J=9.5 Hz, Ph-C—CH$_{2b}$), 4.11 (d, 1H, J=8.2 Hz, Ph-C—CH$_{2a}$), 4.02 (m, 2H, Ph-C—CH$_{2b}$, Ph-N—CH$_{2a}$), 3.79 (dd, 1H, J=6.8 Hz, J=9.1 Hz, Ph-N—CH$_{2b}$), 3.66 (m, 2H, NH—CH$_2$s), 2.03 (s, 3H, HNCO—CH$_3$), 1.90 (s, 3H, NCO—CH$_3$), 1.62 (s, 3H, Ph-C—CH$_3$); $^{13}$C NMR (75 MHz, CDCl$_3$) 171.0, 170.8, 160.3 (d, J$_{CF}$=246 Hz), 154.0, 138.0 (d, J$_{CF}$=11 Hz), 128.2 (d, J$_{CF}$=14 Hz), 127.1 (d, J$_{CF}$=6 Hz), 113.2, 106.3 (d, J$_{CF}$=27 Hz), 71.8, 61.7, 58.7, 47.3, 41.7, 35.2, 28.1, 22.9, 18.6; K.F. Water =1.83%. Anal. Calcd for C$_{18}$H$_{22}$N$_3$O$_4$F$_1$ plus 1.83% water: C, 58.41; H, 6.20; N, 11.35. Found: C, 58.43; H, 6.45; N, 11.27. HRMS Calcd for C$_{18}$H$_{22}$N$_3$O$_4$F$_1$: 363.1594. Found: 363.1585.

EXAMPLE 11

(S)-N-[[3-[3-Fluoro-4-[1-(2-fluoroethyl)-3-(3-methyl)-azetidinyl]-phenyl]-2-oxo-5-oxazolidinyl] methyl]-acetamide An oven-dried 10 mL recovery flask equipped with magnetic spinbar and reflux condenser was charged with 262 mg 2-fluoro-1-tosyl ethanol (1.2 mmol), 321 mg (S)-N-[[3-[3-fluoro-4-[3-methyl-3-azetidinyl]-phenyl]-2-oxo-5-oxazolidinyl]methyl]-acetamide (1.0 mmol), 7.0 mL acetonitrile, and 415 mg powdered potassium carbonate (3.0 mmol). The resulting white suspension was heated to reflux for 16 hours. The visually unchanged reaction mixture was cooled to room temperature, volatiles removed in vacuo, resulting residue diluted with 20 mL water, and extracted twice with dichloromethane (20 mL). The combined organics were washed once with brine (20 mL), dried over MgSO$_4$, filtered, and concentrated to give 394 mg of a light brown syrup. This crude material was purified by LC on 19 g (230–400) silica gel eluting with 7% methanol/ dichloromethane to afford 260 mg (71%) the title compound as a light peach amorphous solid. R$_f$ 0.30 (7% methanol/ dichloromethane); [α]$_D$ −21°(c 0.95445, methanol); IR (mull) 1753, 1660, 1630, 1550, 1515, 1481, 1435, 1411, 1225, 1195 cm$^{-1}$; $^1$H NMR (300 MHz, CDCl$_3$) δ7.36 (dd, 1H, J=2.2 Hz, J=12.7 Hz, aromatic), 7.11 (dd, 1H, J=2.3 Hz, J=8.5 Hz, aromatic), 6.98 (t, 1H, J=8.6 Hz, aromatic), 6.23 (bt, 1H, J=6 Hz, NH), 4.79 (m, 1H, methine), 4.47 (dt, 2H, J=4.8 Hz, J$_{HF}$=47.4 Hz, F—CH$_2$), 4.04 (t, 1H, J=9.0 Hz, Ph-N—CH$_2$ a), 3.77 (dd, 1H, J=6.8 Hz, J=9.2 Hz, Ph-N—CH$_{2b}$), 3.66 (m, 4H, HN—CH$_2$s, N—CH$_{2a}$s), 3.34 (d, 2H, J=7.2 Hz, N—CH$_{2b}$s), 2.75 (dt, 2H, J=4.9 Hz, J$_{HF}$=28.2 Hz, F—CH$_2$—CH$_2$), 2.03 (s, 3H, O=C—CH$_3$), 1.64 (s, 3H, Ph-C—CH$_3$); $^{13}$C NMR (75 MHz, CDCl$_3$) 170.8, 159.9 (d, J$_{CF}$=245 Hz), 153.9, 137.0 (d, J$_{CF}$=11 Hz), 131.1 (d, J$_{CF}$=16 Hz), 127.0 (d, J$_{CF}$=7 Hz), 113.2 (d, J$_{CF}$=3 Hz), 106.2 (d, J$_{CF}$=28 Hz), 82.6 (d, J$_{CF}$=166 Hz), 71.7, 66.0, 58.5 (d, J$_{CF}$=19 Hz), 47.2, 41.6, 36.8, 27.1, 22.8; K.F. Water=1.05%; Anal. Calcd for C$_{28}$H$_3$N$_3$O$_3$F$_2$ plus 1.66% water: C, 57.87; H, 6.39; N, 11.25. Found: C, 57.67; H, 6.43; N, 11.18. HRMS Calcd for C$_{18}$H$_3$N$_3$O$_3$F$_2$: 368.1786. Found: 368.1789.

EXAMPLE 12

(S)-N-[[3-[3-Fluoro-4-[1-(cyanomethyl)-3-(3-methyl)-azetidinyl]-phenyl]-2-oxo-5-oxazolidinyl] methyl]-acetamide An oven-dried 10 mL recovery flask equipped with magnetic spinbar and reflux condenser was charged with 321 mg (S)-N-[[3-[3-fluoro-4-[3-methyl-3-azetidinyl]-phenyl]-2-oxo-5-oxazolidinyl]methyl]-acetamide (1.0 mmol), 7.0 mL acetonitrile, 76 μL chloroacetonitrile (1.2 mmol), and 415 mg powdered potassium carbonate (3.0 mmol). The resulting white suspension was heated to reflux and quickly darkened to a tan color. TLC after 20 minutes indicates almost complete consumption of (S)-N-[[3-[3-fluoro-4-[3-methyl-3-azetidinyl]-phenyl]-2-oxo-5-oxazolidinyl] methyl]-acetamide, and the reaction was stirred at room temperature for 16 hours. The visually unchanged reaction mixture was cooled to room temperature, volatiles removed in vacuo, resulting residue diluted with 20 mL water, and extracted twice with dichloromethane (20 mL). The combined organics were washed once with brine (20 mL), dried over $MgSO_4$, filtered, and concentrated to give 340 mg of a yellow foam. This crude material was purified by LC on 24 g (230–400) silica gel eluting with 5% methanol/dichloromethane to afford 271 mg (75%) the title compound as a white amorphous solid. $R_f$ 0.30 (5% methanol/dichloromethane); $[\alpha]_D$ -22°(c 0.9252, methanol); IR (mull) 1752, 1661, 1631, 1546, 1516, 1480, 1434, 1412, 1227, 1195 $cm^{-1}$; $^1H$ NMR (300 MHz, $CDCl_3$) δ7.39 (dd, 1H, J=2.3 Hz, J=12.8 Hz, aromatic), 7.13 (dd, 1H, J=2.2 Hz, J=8.5 Hz, aromatic), 6.99 (t, 1H, J=8.6 Hz, aromatic), 6.30 (bt, 1H, J=6 Hz, NH), 4.79 (m, 1H, methine), 4.03 (t, 1H, J=9.0 Hz, Ph-N—$CH_{2a}$), 3.77 (dd, 1H, J=6.8 Hz, J=9.1 Hz, Ph-N—$CH_{2b}$), 3.66 (m, 2H, HN—$CH_2$S), 3.55 (s, 4H, N—$OH_2$s), 3.49 (s, 2H, NC—$CH_2$), 2.02 (s, 3H, O=C—$CH_3$), 1.64 (s, 3H, Ph-C—$CH_3$); 13C NMR (75 MHz, $CDCl_3$); 171.1, 159.9 (d, $J_{CF}$=246 Hz), 154.1, 137.4 (d, $J_{CF}$=11 Hz), 129.7 (d, $J_{CF}$=15 Hz), 126.9 (d, $J_{CF}$=7 Hz), 114.8, 113.3, 106.2 (d, $J_{CF}$=28 Hz), 71.8, 63.3, 47.2, 43.9, 41.6, 36.5, 26.9, 22.8; K.F. Water =1.42%; Anal. Calcd for $C_{18}H_{21}N_4O_3F_1$ plus 1.42% water: C, 59.14; H, 5.95; N, 15.33. Found: C, 58.96; H, 5.88; N, 15.33. HRMS Calcd for $CO_8H_{21}N_4O_3F_1$: 360.1598. Found: 360.1610.

EXAMPLE 13

(S)-N-[[3-[3-Fluoro-4-[1-(5-nitro-2-thiazolyl)-3-(3-methyl)-azetidinyl]-phenyl]-2-oxo-5-oxazolidinyl] methyl]-acetamide An oven-dried 10 mL round bottom flask equipped with magnetic spinbar was charged with 241 mg (S)-N-[[3-[3-fluoro-4-[3-methyl-3-azetidinyl]-phenyl]-2-oxo-5-oxazolidinyl]methyl]-acetamide (0.75 mmol), 4 mL dimethylsulfoxide, and 188 mg 2-bromo-5-nitrothiazole. This golden homogenous solution was treated with 207 mg powdered potassium carbonate (1.5 mmol) and stirred at room temperature for 16 hours. The now dark brown suspension was diluted with 40 mL dichloromethane and washed with water (3×15 mL), once with brine (15 mL), dried over $MgSO_4$, filtered, and concentrated to give 280 mg of an orange foam. This crude material was purified by LC on 18 g (230–400) silica gel eluting with 5% methanol/dichloromethane to afford 191 mg (56%) the title compound as a yellow solid. This material was recrystallized from ethyl acetate/hexane to afford 88 mg of a yellow solid. mp 182–185° C. (dec.); $R_f$ 0.29 (5% methanol/dichloromethane); $[\alpha]_D$ -20°(c 0.4062, DMSO); IR (mull) 1747, 1771, 1572, 1517, 1498, 1475, 1439, 1282, 1228, 1199, $cm^{-1}$; $^1H$ NMR (300 MHz, $CDCl_3$) δ7.50 (dd, 1H, J=2.1 Hz, J=13.1 Hz, aromatic), 7.20 (dd, 1H, J=2.2 Hz, J=8.5 Hz, aromatic), 7.12 (t, 1H, J=8.5 Hz, aromatic), 4.79 (m, 1H, methine), 4.51 (d, 2H, J=8.9, Ph-C—$CH_2$s), 4.24 (d, 2H, J=9.4 Hz, Ph-C—$CH_2$s), 4.07 (t, 1H, J=9.0 Hz, Ph-N—$CH_{2a}$), 3.79 (dd, 1H, J=7.0 Hz, J=9.5 Hz, Ph-N—$CH_{2b}$), 3.62 (m, 2H, NH—$CH_2$s), 2.01 (s, 3H, O=C—$CH_3$), 1.75 (s, 3H, Ph-C—$CH_3$); $^{13}C$ NMR (75 MHz, $CDCl_3$) 201.0, 171.9, 171.8, 160.1 (d, $J_{CF}$=247 Hz), 154.6, 145.5, 138.4 (d, $J_{CF}$=11 Hz), 127.1, 126.9 (d, $J_{CF}$=6 Hz), 113.5, 106.5 (d, $J_{CF}$=27 Hz), 72.2, 64.0, 47.4, 41.7, 38.1, 28.0, 22.4; K.F. Water=0.59%. Anal. Calcd for $C_{19}H_{20}N_5O_5F_1S_1$ plus 0.59% water: C, 50.48; H, 4.53; N, 15.49. Found: C, 50.26; H, 4.69; N, 15.29.

EXAMPLE 14

(S)-N-[[3-[3-Fluoro-4-[1-(methanesulfonyl)-3-(3-methyl)-azetidinyl]-phenyl]-2-oxo-5-oxazolidinyl] methyl]-acetamide An oven-dried 15 mL round bottom flask equipped with magnetic spinbar was charged with 241 mg (S)-N-[[3-[3-fluoro-4-[3-methyl-3-azetidinyl]-phenyl]-2-oxo-5-oxazolidinyl]methyl]-acetamide (0.75 mmol), 8 mL dichloromethane, and cooled to 0° C. The colorless but slightly opaque solution was treated with 0.16 mL triethylamine (1.1 mmol) and 70 μL methanesulfonyl chloride (0.90 mmol) with no visible change. The cooling bath was removed and the reaction mixture was warmed to room temperature over three hours. The now clear solution was concentrated to a colorless syrup. This crude material was purified by LC on 18 g (230–400) silica gel eluting with 5% methanol/ethyl acetate to afford 234 mg (78%) the title compound as a white foam. $R_f$ 0.30 (5% methanol/ethyl acetate); $[\alpha]_D$ -9°(c 0.9701, methanol; IR (mull) 1753, 1664, 1631, 1517, 1436, 1412, 1333, 1228, 1194, 1151 $cm^{-1}$; $^1H$ NMR (300 MHz, $CDCl_3$) δ7.44 (dd, 1H, J=2.2 Hz, J=13.0 Hz, aromatic), 7.16 (m, 1H, aromatic), 7.00 (t, 1H, J=8.6 Hz, aromatic), 6.30 (bt, 1H, J=6 Hz, NH), 4.80 (m, 1H, methine), 4.24 (d, 2H, J=7.4 Hz, Ms-N—$CH_{2a}$s), 4.05 (t, 1H, J=9.0 Hz, Ph-N—$CH_{2a}$), 3.88 (d, 2H, J=7.6 Hz, Ms-N—$CH_{2b}$s), 3.79 (m, 1H, Ph-N—$CH_{2b}$), 3.66 (m, 2H, NH—$CH_2$s), 2.87 (s, 3H, S—$CH_3$), 2.03 (s, 3H, O=C—$CH_3$), 1.68 (s, 3H, Ph-C—$CH_3$); 13C NMR (75 MHz, $CDCl_3$) 171.2, 160.2 (d, $J_{CF}$=246 Hz), 154.2, 138.3 (d, $J_{CF}$=11 Hz), 128.2 (d, $J_{CF}$=15 Hz), 126.9 (d, $J_{CF}$=6 Hz), 113.5 (d, $J_{CF}$=3 Hz), 106.5 (d, $J_{CF}$=28 Hz), 72.0, 60.8, 47.4, 41.8, 36.2, 35.0, 27.4, 23.1; Melt solvate=0.3% ethyl acetate; K.F. Water=1.05%; Anal. Calcd for $C_{17}H_{22}N_3O_5F_1S_1$ plus 0.3% ethyl acetate and 1.05% water: C, 50.59; H, 5.62; N, 10.38. Found: C, 50.50; H, 5.81; N, 10.29. HRMS Calcd for $C_{17}H_{22}N_3O_5F_1S_1$: 400.1342. Found: 400.1352.

EXAMPLE 15

(S)-N-[[3-[3-Fluoro-4-[1-(benzyloxyacetyl)-3-(3-methyl)-azetidinyl]-phenyl]-2-oxo-5-oxazolidinyl] methyl]-acetamide An oven-dried 25 mL round bottom flask equipped with magnetic spinbar was charged with 313 mg (S)-N-[[3-[3-fluoro-4-[3-methyl-3-azetidinyl]-phenyl]-2-oxo-5-oxazolidinyl]methyl]-acetamide (0.97 mmol), 10 mL dichloromethane, and cooled to 0° C. The colorless but slightly opaque solution was treated with 0.27 mL triethylamine (2.0 mmol) and 0.23 mL benzyloxyacetyl chloride (1.5 mmol) with the reaction mixture becoming clear and a pale yellow color. The cooling bath was removed and the reaction mixture was warmed to room temperature over 16 hours. The visually unchanged solution was diluted with 15 mL saturated sodium bicarbonate and extracted twice with dichloromethane (20 mL). The combined organics were washed once with 15 mL brine, dried over $MgSO_4$, filtered, and concentrated to give 521 mg of a light yellow foam. This crude material was purified by LC on 27 g (230–400) silica gel eluting with 10% methanol/ethyl acetate to afford 370 mg (81%) the title compound as a white foam. $R_f$ 0.29 (10% methanol/ethyl acetate); $[\alpha]_D$ −17°(c 0.9516, methanol); IR (mull) 1754, 1654, 1631, 1548, 1516, 1438, 1411, 1226, 1193, 1122 cm$^{-1}$; $^1$H NMR (300 MHz, CDCl$_3$) δ7.45 (dd, 1H, J=2.2 Hz, J=13.0 Hz, aromatic), 7.33 (m, 5H, aromatic), 7.15 (dd, 1H, J=2.2 Hz, J=8.5 Hz, aromatic), 7.04 (t, 1H, J=8.6 Hz, aromatic), 6.42 (bt, 1H, J=6 Hz, NH), 4.79 (m, 1H, methine), 4.57 (s, 2H, Ph-CH$_2$), 4.50 (d, 1H, J=9.0 Hz, Ph-C—CH$_{2a}$), 4.33 (d, 1H, J=9.7 Hz, Ph-C—CH$_{2b}$), 4.23 (d, 1H, J=9.2 Hz, Ph-C—CH$_{2b}$), 4.04 (m, 4H, Ph-C—CH$_{2a}$, O—CH$_2$, Ph-N—CH$_{2a}$), 3.79 (dd, 1H, J=6.8 Hz, J=9.0 Hz, Ph-N—CH$_{2b}$), 3.66 (m, 2H, NH—CH$_2$), 2.02 (s, 3H, O=C—CH$_3$), 1.61 (s, 3H, Ph-C—CH$_3$); $^{13}$C NMR (75 MHz, CDCl$_3$) 171.1, 169.6, 160.3 (d, $J_{CF}$=246 Hz), 154.1, 138.1 (d, $J_{CF}$=11 Hz), 137.0, 128.4, 128.2, 128.0, 127.9, 127.2 (d, $J_{CF}$=6 Hz), 113.3, 106.5 (d, $J_{CF}$=26 Hz), 73.3, 71.9, 69.0, 62.4, 59.4, 47.4, 41.8, 36.7, 28.2, 23.0; HRMS Calcd for C$_{25}$H$_{28}$N$_3$O$_5$F$_1$: 470.2091. Found: 470.2101.

EXAMPLE 16

(S)-N-[[3-[3-Fluoro-4-[1-(hydroxyacetyl)-3-(3-methyl)-azetidinyl]-phenyl]-2-oxo-5-oxazolidinyl]methyl]-acetamide A 250 mL Parr flask was charged with a solution of 310 mg (S)-N-[[3-[3-fluoro-4-[1-(benzyloxyacetyl)-3-(3-methyl)-azetidinyl]-phenyl]-2-oxo-5-oxazolidinyl]methyl] acetamide (0.66 mmol) in 30 mL methanol and 31 mg 10% palladium on carbon. The black suspension was placed under 40 psi hydrogen with shaking for 16 hours with the pressure remaining constant. The reaction was monitored by TLC analysis with several additional equivalents of 10% palladium on carbon (300 mg total amount) and prolonged time (five days) to fully consume (S)-N-[[3-[3-fluoro-4-[1-(benzyloxyacetyl)-3-(3-methyl)-azetidinyl]-phenyl]-2-oxo-5-oxazolidinyl]-methyl]-acetamide. The reaction mixture was filtered through a pad of Celite and concentrated to afford 221 mg (88%) the title compound as an off-white amorphous solid. $R_f$ 0.21 (15% methanol/ethyl acetate); $[\alpha]_D$ −20°(c 0.9432, methanol); IR (mull) 1754, 1655, 1632, 1552, 1517, 1481, 1435, 1412, 1227, 1192 cm$^{-1}$; $^1$H NMR (300 MHz, CDCl$_3$) δ7.47 (d, 1H, J=2.1 Hz, J=13.0 Hz, aromatic), 7.15 (dd, 1H, J=2.2 Hz, J=8.5 Hz, aromatic), 7.07 (t, 1H, J=8.6 Hz, aromatic), 6.37 (bt, 1H, J=6 Hz, NH), 4.80 (m, 1H, methine), 4.38 (m, 2H, Ph-C—CH$_{2a\&b}$), 4.01 (m, 5H, Ph-C—CH$_{2a\&b}$, HO—CH$_2$, Ph-N—CH$_{2a}$), 3.79 (dd, 1H, J=6.8 Hz, J=9.1 Hz, Ph-N—CH$_{2b}$), 3.68 (m, 2H, HN—CH$_2$s), 2.03 (s, 3H, O=C—CH$_3$), 1.65 (s, 3H, Ph-C—CH) 171.3, 170.9, 160.1 (d, $J_{CF}$=246 Hz), 153.9, 138.1 (d, $J_{CF}$=11 Hz), 127.6 (d, $J_{CF}$=14 Hz), 126.9 (d, $J_{CF}$=6 Hz), 113.1, 106.3 (d, $J_{CF}$=28 Hz), 71.8, 60.1, 59.3, 58.5, 47.1, 41.6, 37.0, 28.0, 22.8; HRMS Calcd for C$_{18}$H$_{22}$N$_3$O$_5$F$_1$: 379.1543. Found: 379.1542.

EXAMPLE 17

(S)-(−)-N-[[2-Oxo-3-[4-(4-piperidinyl)phenyl]-5-oxazolidinyl]methyl]acetamide

Step 1: 4-Hydroxy-4-[4-[[(phenylmethoxy)carbonyl]amino]phenyl]-1-piperidinecarboxylic acid phenylmethyl ester To a solution of N-(carbobenzyloxy)-4-bromoaniline (5.00 g) in dry tetrahydrofuran (80 mL) at −78° C. under N$_2$ is added n-butyllithium (21.4 mL, 1.6 M in hexanes) dropwise over five minutes. The resulting yellow solution is stirred at −78° C. for 30 minutes and is then treated with a solution of N-(carbobenzyloxy)-4-piperidone (3.99 g) in dry tetrahydrofuran (17 mL). The reaction mixture is stirred for three hours, during which the reaction temperature is allowed to rise to 0° C., and is quenched with saturated aqueous ammonium chloride (30 mL). The mixture is then diluted with water (100 mL), the layers are separated, the aqueous phase is extracted with diethyl ether, and the combined organic phase is washed with saline (50 mL), dried over anhydrous sodium sulfate, and concentrated under reduced pressure. The residue is chromato-graphed on silica gel (230–400 mesh, 350 g), eluting with ethyl acetate/hexane (25/75), and those fractions with an $R_f$=0.38 by TLC (ethyl acetate/hexane, 50/50) are pooled and con-centrated under reduced pressure to give the title compound, mp 156° C.–158° C.

Step 2: 3,6-Dihydro-4-[4-[[(phenylmethoxy)carbonyl]amino]phenyl]-1(2H)-pyridinecarboxylic acid phenylmethyl ester A solution of 4-hydroxy-4-[4-[[(phenylmethoxy)carbonyl]amino]phenyl]-1-piperidinecarboxylic acid phenylmethyl ester (EXAMPLE 17, Step 1, 2.50 g) in dry methylene chloride under N$_2$ is treated with trifluoroacetic acid (0.84 mL), stirred at ambient temperature for three hours, diluted with saturated aqueous potassium carbonate (25 mL) to neutralize excess trifluoroacetic acid, and the layers are separated. The organic phase is washed with water (20 mL) and saline (20 mL), dried over anhydrous sodium sulfate and concentrated under reduced pressure, and the residue is chromatographed on silica gel (230–400 mesh, 300 g), eluting with a gradient of ethyl acetate/hexane (20/80–50/50). Pooling of fractions with an $R_f$=0.69 by TLC (ethyl acetate/hexane, 50/50) and removal of solvent under reduced pressure gives the title compound, mp 146–148° C.

Step 3: (R-(−)-3,6-Dihydro-4-[4-[5-(hydroxymethyl)-2-oxo-3-oxazolidinyl]phenyl]-1(2H)-pyridinecarboxylic acid phenylmethyl ester A solution of 3,6-dihydro-4-[4-[[(phenylmethoxy)carbonyl]amino]phenyl]-1(2H)-pyridinecarboxylic acid phenylmethyl ester (EXAMPLE 17, Step 2, 0.500 g) in dry tetrahydrofuran (5.7 mL) at −78° C. under N$_2$ is treated with n-butyllithium (0.73 mL, 1.6 M in hexanes) dropwise over five minutes. The resulting mixture is stirred at −78° C. for 45 minutes and is then treated with (R)-(−)-glycidyl butyrate dropwise. The resulting solution is allowed to warm to ambient temperature over approximately 45 minutes and is stirred for an additional 20 hours, after which the reaction is quenched with saturated aqueous ammonium chloride (10 mL), diluted with water (20 mL) and extracted with ethyl acetate (2×15 mL). The combined organic phase is washed with saline (10 mL), dried over anhydrous magnesium sulfate and concentrated under reduced pressure to give the crude product which is chromatographed on silica gel (230–400 mesh, 40 g), eluting with methanol/methylene chloride (1/99). Pooling and concentration of those fractions with an $R_f$=0.37 by TLC (methanol/chloroform, 5/95) gives the title compound, mp 131.5–133.5° C.

Step 4: (R)-(−)-3,6-Dihydro-4-[4-[5-[[(methylsulfonyl)oxy]methyl]-2-oxo-3-oxazolidinyl]phenyl]-1(2H)-pyridinecarboxylic acid phenylmethyl ester A solution of (R)-(−)-3,6-dihydro-4-[4-[5-(hydroxymethyl)-2-oxo-3-oxazolidinyl]phenyl]-1(2H)-pyridinecarboxylic acid phenylmethyl ester (EXAMPLE 17, Step 3, 970 mg) and triethylamine (0.50 mL) in dry methylene chloride (9.5 mL) at 0° C. under N$_2$ is treated with methanesulfonyl chloride (0.20 mL) dropwise. The resulting mixture is stirred at 0° C. for one hour, diluted with methylene chloride (40 mL), washed with water (10 mL), saturated aqueous sodium bicarbonate (10 mL) and saline (10 mL), dried over anhydrous sodium sulfate and concen-trated under reduced pressure to give the title compound, mp 166–168° C.

Step 5: (S)-(-)-4-[4-[5-[(Acetylamino)methyl]-2-oxo-3-oxazolidinyl]phenyl]-3,6-dihydro-1(2H)-pyridinecarboxylic acid phenylmethyl ester A mixture of (R)-(-)-3,6-dihydro-4-[4-[5-[[(methylsulfonyl)oxy]methyl-2-oxo-3-oxazolidinyl]phenyl]-1(2H)-pyridinecarboxylic acid phenylmethyl ester (EXAMPLE 17, Step 4, 935 mg) and concentrated aqueous ammonium hydroxide (4 mL) in isopropanol (4 mL) and tetrahydrofuran (4 mL) is placed in a sealed tube and immersed in an oil bath maintained at 95° C. for 18 hours. The mixture is then diluted with methylene chloride (40 mL), washed with saline (20 mL), dried over anhydrous sodium sulfate and concentrated under reduced pressure to give the 5-aminomethyl-2-oxazolidinone intermediate ($R_f$=0.34 by TLC, methanol/chloroform, 10/90). A solution of this intermediate (783 mg) and pyridine (1.55 mL) in dry methylene chloride (19 mL) at 0° C. under $N_2$ is treated with acetic anhydride (0.90 mL), and the resulting solution is allowed to warm to ambient temperature with stirring over 1.5 hours. The mixture is then diluted with methylene chloride (20 mL), washed with water (10 mL), saturated aqueous sodium bicarbonate (2×10 mL) and saline (10 mL), dried over anhydrous sodium sulfate and concentrated under reduced pressure to give the crude product which is chromatographed on silica gel (230–400 mesh, 75 g), eluting with a gradient of methanol/methylene chloride (1/99–2/98). Pooling and concentration of those fractions with an $R_f$=0.26 by TLC (methanol/chloroform, 5/95) gives the title compound, mp 166–169° C.

Step 6: (S)-(-)-N-[[2-Oxo-3-4-(4-piperidinyl)phenyl]-5-oxazolidinyl]methyl]acetamide A mixture of (S)-(-)-[4-[4-[5-[(acetylamino)methyl]-2-oxo-3-oxazolidinyl]phenyl]-3,6-dihydro-1(2H)-pyridinecarboxylic acid phenylmethyl ester (EXAMPLE 17, Step 5, 625 mg) and 10% palladium-on-carbon (300 mg) in methanol (100 mL) is shaken on a Parr apparatus under a hydrogen atmosphere at 40 psi for one hour and at 20 psi for 16 hours, the catalyst is removed by filtration through Celite and the filtrate is concentrated under reduced pressure to give the title compound, mp 169–171° C.

EXAMPLE 18

(S)-(-)-N-[[3-[4-[1-[(Benzyloxy)acetyl]-4-piperidinyl]phenyl]-2-oxo-5-oxazolidinyl]methyl]acetamide A mixture of (S)-(-)-N-[[2-oxo-3-[4-(4-piperidinyl)phenyl]-5-oxazolidinyl]methyl]acetamide (EXAMPLE 17, 300 mg) and triethylamine (0.20 mL) in dry methylene chloride (19 mL) at 0° C. under $N_2$ is treated with benzyloxyacetyl chloride (0.18 mL), and the resulting solution is stirred at 0° C. for one hour and at ambient temperature for one hour. The reaction mixture is then washed with water (2×10 mL), saturated aqueous sodium bicarbonate (10 mL) and saline (10 mL), dried over anhydrous sodium sulfate and concentrated under reduced pressure to give the crude product which is chromatographed on silica gel (230–400 mesh, 45 g), eluting with a gradient of methanol/methylene chloride (1/99–2/98). Pooling and concentration of those fractions with an $R_f$=0.28 by TLC (methanol/chloroform, 5/95) gives the title compound, NMR ($CDCl_3$, 400 MHz) 7.45, 7.35, 7.18, 6.26, 4.75, 4.63, 4.22, 4.04, 3.78, 3.70, 3.60, 3.09, 2.70, 2.02, 1.85, 1.60 δ.

EXAMPLE 19

(S)-(-)-N-[3-[4-[1-(Hydroxyacetyl)-4-piperidinyl]phenyl]-2-oxo-5-oxazolidinyl]methyl]acetamide A mixture of (S)-(-)-N-[[3-[4-[1-[(benzyloxy)acetyl]-4-piperidinyl]phenyl]-2-oxo-5-oxazolidinyl]methyl]acetamide (EXAMPLE 18, 207 mg) and 10% palladium-on-carbon (100 mg) in methanol (9 mL) is shaken on a Parr apparatus under a hydrogen atmosphere at 40 psi for 20 hours, the catalyst is removed by filtration through Celite and the filtrate is concentrated under reduced pressure to give the crude product which is chromatographed on silica gel (230–400 mesh, 20 g), eluting with a gradient of methanol/methylene chloride (5/95–10/90). Pooling and concentration of those fractions with an $R_f$=0.26 by TLC (methanol/chloroform, 10/90) and recrystallization from methylene chloride/diethyl ether gives the title compound, mp 155–157° C.

EXAMPLE 20

(S)-(-)-N-[[2-Oxo-3-[4-(4-piperidinyl)-3-fluorophenyl]-5-oxazolidinyl]methyl]acetamide Step 1: 1-(3-Fluorophenyl)-2,2,5,5-tetramethyl-1-aza-2,5-disilacyclopentane A solution of freshly distilled diisopropylamine (22.9 mL) in dry tetrahydrofuran (175 mL) at -78° C. under $N_2$ is treated with n-butyllithium (1.6 M in hexanes, 109 mL) dropwise over 15 minutes, and the resulting mixture is stirred at -78° C. for 45 minutes and is then added over ten minutes via cannula to a solution of 3-fluoroaniline (8.00 mL) in dry tetrahydrofuran (166 mL) at -78° C. under $N_2$. The resulting reaction mixture is stirred at -78° C. for 50 minutes and is then treated with a solution of 1,1,4,4-tetramethyl-1,4-dichlorodisilethylene (18.3 g) in dry tetrahydrofuran (85 mL). The mixture is allowed to slowly warm to ambient temperature over four hours with stirring and is then washed with water (2×200 mL) and saline (100 mL), dried over anhydrous sodium sulfate and concentrated under reduced pressure to give the title compound, NMR ($CDCl_3$, 400 MHz) 7.12, 6.65, 6.58, 0.86, 0.24 δ.

Step 2: 3,6-Dihydro-4-[[(trifluoromethyl)sulfonyl]oxy]-1(2H)-pyridinecarboxylic acid 1,1-dimethylethyl ester A solution of freshly distilled diisopropylamine (8.70 mL) in dry tetrahydrofuran (133 mL) at -78° C. under $N_2$ is treated with n-butyllithium (1.6 M in hexanes, 41.5 mL) dropwise over ten minutes, and the resulting mixture is stirred at -78° C. for one hour and is then treated with a solution of 1-(1,1-dimethylethoxycarbonyl)-4-piperidone (12.0 g) in dry tetrahydrofuran (120 mL) dropwise over 10 minutes. The resulting mixture is stirred at -78° C. for 40 minutes and is then treated with a solution of N-phenyltrifluoromethanesulfonimide (22.0 g) in dry tetrahydrofuran (62 mL) over five minutes. The reaction mixture is stirred at -78° C. for 10 minutes and at 0° C. for four hours and is then quenched with water (200 mL). The layers are separated, the aqueous phase is extracted with diethyl ether (100 mL) and the combined organic phase is washed with saline (50 mL), dried over anhydrous magnesium sulfate and concentrated under reduced pressure to give the title compound, NMR ($CDCl_3$, 400 MHz) 5.77, 4.05, 3.64, 2.45, 1.48 δ.

Step 3: 3,6-Dihydro-4-[4-amino-2-fluorophenyl]-1(2H)-pyridinecarboxylic acid 1,1-dimethylethyl ester A solution of 1-(3-fluorophenyl)-2,2,5,5-tetramethyl-1-aza-2,5-disilacyclopentane (EXAMPLE 20, Step 1, 19.1 g) in dry tetrahydrofuran (150 mL) at -78° C. under $N_2$ is treated with sec-butyllithium (1.3 M in cyclohexane, 60.3 mL) dropwise over ten minutes, and the resulting mixture is stirred at -78° C. for 2.25 hours. A solution of zinc chloride (0.5 M in tetrahydrofuran, 150 mL) is then added over 15 minutes, and the mixture is allowed to warm to ambient temperature over one hour with stirring. A solution of 3,6-dihydro-4-[[(trifluoromethyl)-sulfonyl]oxy]-1(2H)- pyridinecarboxylic acid 1,1-dimethylethyl ester (EXAMPLE 20, Step 2, 20.8 g) in dry tetrahydrofuran (63 mL) and tetrakis(triphenylphosphine)palladium(0) (1.45 g) is added, and the mixture is degassed, heated up to reflux, refluxed for five minutes, cooled to ambient temperature and stirred for 12 hours. The mixture is then diluted with water (150 mL), the layers are separated, the aqueous phase is extracted with diethyl ether (2×100 mL) and the combined organic phase is washed with water (100 mL) and saline (100 mL), dried over anhydrous magnesium sulfate and concentrated under reduced pressure. The residue is then dissolved in methanol (630 mL) and treated with anhydrous potassium carbonate (17.3 g), and the mixture is stirred at ambient temperature for 40 minutes, concentrated under reduced pressure, diluted with water (100 mL) and extracted with diethyl ether (2×150 mL). The combined organic phase is washed with water (50 mL) and saline (50 mL), dried over anhydrous magnesium sulfate and concentrated under reduced pressure to give the crude product which is chromatographed on silica gel (230–400 mesh, 1 kg), eluting with a gradient of ethyl acetate/hexane (15/85–50/50). Pooling and concentration of those fractions with an $R_f$=0.17 by TLC (ethyl acetate/hexane, 25/75) gives the title compound, mp 123–125° C.

Step 4: 4-[4-[[(Phenylmethoxy)carbonyl]amino-2-fluorophenyl]-1-piperidinecarboxylic acid 1,1-dimethylethyl ester A mixture of 3,6-dihydro-4-[4-amino-2-fluorophenyl]-1 (2H)-pyridinecarboxylic acid 1,1-dimethylethyl ester (EXAMPLE 20, Step 3, 11.44 g) and 10% palladium-on-carbon (4 g) in methanol (400 mL) in four Parr bottles is shaken on the Parr apparatus under a hydrogen atmosphere at 40 psi for two hours, the catalyst is removed by filtration through Celite, and the filtrate is concentrated under reduced pressure to give the 4-[4-amino-2-fluorophenyl]-1-piperidinecarboxylic acid 1,1-dimethylethyl ester intermediate. A mixture of this intermediate (11.17 g) and sodium bicarbonate (6.57 g) in dry tetrahydrofuran (390 mL) is treated with benzyl chloroformate (5.86 mL), and the resulting mixture is stirred at ambient temperature for 15 hours and washed with water (200 mL). The aqueous phase is extracted with methylene chloride (150 mL), and the combined organic phase is washed with saline (50 mL), dried over anhydrous sodium sulfate and concentrated under reduced pressure to give the crude product which is chromatographed on silica gel (70–230 mesh, 800 g), eluting with a gradient of ethyl acetate/hexane (15/85–25/75). Pooling and concentration of those fractions with an $R_f$=0.38 by TLC (ethyl acetate/hexane, 25/75) gives the title compound, mp 96–98° C.

Step 5: (R)-(−)-4-[4-[5-(Hydroxymethyl)-2-oxo-3-oxazolidinyl]-2-fluorophenyl]-1-piperidinecarboxylic acid 1,1-dimethylethyl ester A solution of 4-[4-[[(phenylmethoxy)carbonyl]amino-2-fluorophenyl]-1-piperidinecarboxylic acid 1,1-dimethylethyl ester (EXAMPLE 20, Step 4, 0.500 g) in dry tetrahydrofuran (5.7 mL) at −78° C. under $N_2$ is treated with n-butyllithium (0.73 mL, 1.6 M in hexanes) dropwise over five minutes. The resulting mixture is stirred at −78° C. for 45 minutes and is then treated with (R)-(−)-glycidyl butyrate dropwise. The resulting solution is allowed to warm to ambient temperature over approximately 45 minutes and is stirred for an additional 20 hours, after which the reaction is quenched with saturated aqueous ammonium chloride (10 mL), diluted with water (20 mL) and extracted with ethyl acetate (2×15 mL). The combined organic phase is washed with saline (10 mL), dried over anhydrous magnesium sulfate and concentrated under reduced pressure to give the crude product which is chromatographed on silica gel (230–400 mesh, 40 g), eluting with methanol/methylene chloride (1/99). Pooling and concentration of those fractions with an $R_f$=0.37 by TLC (methanol/chloroform, 5/95) gives the title compound, mp 120–122° C.

Step 6: (R)-(−)-4-[4-[5-[[(Methylsulfonyl)oxy]methyl]-2-oxo-3-oxazolidinyl]-2-fluorophenyl]-1-piperidinecarboxylic acid 1,1-dimethylethyl ester A solution of (R)-(−)-4-(4-[5-(hydroxymethyl)-2-oxo-3-oxazolidinyl]-2-fluorophenyl]-1-piperidinecarboxylic acid 1,1-dimethylethyl ester (EXAMPLE 20, Step 5, 970 mg) and triethylamine (0.50 mL) in dry methylene chloride (9.5 mL) at 0° C. under $N_2$ is treated with methanesulfonyl chloride (0.20 mL) dropwise. The resulting mixture is stirred at 0° C. for one hour, diluted with methylene chloride (40 mL), washed with water (10 mL), saturated aqueous sodium bicarbonate (10 mL) and saline (10 mL), dried over anhydrous sodium sulfate and concentrated under reduced pressure to give the title compound, mp 163–165° C.

Step 7: (R)-(−)-4-[4-[5-(Azidomethyl)-2-oxo-3-oxazolidinyl]-2-fluorophenyl]-1-piperidinecarboxylic acid 1,1-dimethylethyl ester A mixture of (R)-(−)-4-[4-[5-[[(methylsulfonyl)oxy]methyl]-2-oxo-3-oxazolidinyl]-2-fluorophenyl]-1-piperidinecarboxylic acid 1,1-dimethylethyl ester (EXAMPLE 20, Step 6, 13.83 g) and sodium azide (7.62 g) in dry dimethylformamide (117 mL) under $N_2$ is stirred at 60° C. for five hours and at ambient temperature for 16 hours. The mixture is then diluted with ethyl acetate (200 mL), washed with water (8×100 mL) and saline (100 mL), dried over anhydrous magnesium sulfate and concentrated under reduced pressure to give the title compound, mp 109–110° C.

Step 8: (S)-(−)-4-[4-[5-(Aminomethyl)-2-oxo-3-oxazolidinyl]-2-fluorophenyl]-1-piperidinecarboxylic acid 1,1-dimethylethyl ester A solution of (R)-(−)-4-[4-[5-(azidomethyl)-2-oxo-3-oxazolidinyl]-2-fluorophenyl]-1-piperidinecarboxylic acid 1,1-dimethylethyl ester (EXAMPLE 20, Step 7, 12.05 g) in dry tetrahydrofuran (96 mL) under $N_2$ is treated with triphenylphosphine (8.29 g) over five minutes, and the resulting mixture is stirred at ambient temperature for two hours. The mixture is then treated with water (3.1 mL), heated up to 40° C., stirred at 40° C. for five hours and at ambient temperature for 12 hours, and then concentrated under reduced pressure to give a viscous oil which is chromatographed on silica gel (70–230 mesh, 500 g), eluting with a gradient of methanol/methylene chloride (2.5/97.5–15/85). Pooling and concentration of those fractions with an $R_f$=0.26 by TLC (methanol/chloroform, 10/90) gives the title compound, mp 136–137° C.

Step 9: (S)-(−)-4-[4-[5-[(Acetylamino)methyl]-2-oxo-3-oxazolidinyl]-2-fluorophenyl]-1-piperidinecarboxylic acid 1,1-dimethylether ester A solution of (S)-(−)-4-[[5-(aminomethyl)-2-oxo-3-oxazolidinyl]-2-fluorophenyl]-1-piperidinecarboxylic acid 1,1-dimethylethyl ester (EXAMPLE 20, Step 8, 9.45 g) in dry methylene chloride (96 m L) under $N_2$ is treated with pyridine (5.82 mL) and acetic anhydride (3.40 mL), and the resulting mixture is stirred at ambient temperature for four hours, diluted with methylene chloride (25 mL), washed with water (25 mL), saturated aqueous sodium bicarbonate (25 mL) and saline (25 mL), dried over anhydrous sodium sulfate and concentrated under reduced pressure to give the crude product which is then chromatographed on silica gel (230–400 mesh, 350 g), eluting with a gradient of methanol/ chloroform (2.5/97.5–7.5/92.5). Pooling and concentration of those fractions with an $R_f$=0.51 by TLC (methanol/chloroform, 10/90) gives the title compound, mp 144–146° C.

Step 10: (S)-(−)-N-[[2-Oxo-3-[4-(4-piperidinyl)-3-fluorophenyl]-5-oxazolidinyl]methyl]acetamide A solution of (S)-(−)-4-[4-[5-[(acetylamino)methyl]-2-oxo-3-oxazolidinyl]-2-fluorophenyl]-1-piperidinecarboxylic acid phenylmethyl ester (EXAMPLE 20, Step 9, 10.44 g) in dry methylene chloride (100 mL) at 0° C. under $N_2$ is treated with trifluoroacetic acid (24.0 mL) over one minute, and the resulting mixture is stirred at 0° C. for 1.75 hours, concentrated under reduced pressure, diluted with water (100 mL), cooled in an ice bath, adjusted to pH 11 with saturated aqueous potassium carbonate, and extracted with methanol/methylene chloride (5/95, 6×100 mL). The combined organic phase is dried over anhydrous sodium sulfate and concentrated under reduced pressure to give the title compound, mp 163–164° C.

EXAMPLE 21

(S)-(−)-N-[[3-[4-[1-[(Benzyloxy)acetyl]-4-piperidinyl]-3-fluorophenyl]-2-oxo-5-oxazolidinyl]methyl]acetamide Following the general procedure of EXAMPLE 18, and making non-critical variations but substituting (S)-(−)-N-[[2-oxo-3-[4-(4-piperidinyl)-3-fluorophenyl]-5-oxazolidinyl]methyl]-acetamide (EXAMPLE 20,) for (S)-(−)-N-[[2-oxo-3-[4-(4-piperidinyl)phenyl]-5-oxazolidinyl]-methyl]acetamide and purifying the crude product by trituration with chloroform/diethyl ether and filtration, the title compound is obtained, mp 147–149° C.

EXAMPLE 22

(S)-(−)-N-[[3-[4-[1-(Hydroxyacetyl)-4-piperidinyl]-3-fluorophenyl]-2-oxo-5-oxazolidinyl]methyl]acetamide A mixture of (S)-(−)-N-[[3-[4-[1-[(benzyloxy)acetyl]4-piperidinyl]-3-fluorophenyl]-2-oxo-5-oxazolidinyl]methyl]acetamide (EXAMPLE 21, 5.00 g) and 20% palladium hydroxide on carbon (2.80 g) in methanol (500 mL) is stirred under a hydrogen atmosphere (balloon) for four hours, the catalyst is removed by filtration through Celite and the filtrate is concentrated under reduced pressure, triturated with methylene chloride/diethyl ether and filtered to give the title compound, mp 182–183° C.

EXAMPLE 23

(S)-(−)-N-[[3-[4-[1-(Indole-2-carbonyl)-4-piperidinyl]-3-fluorophenyl]-2-oxo-5-oxazolidinyl]methyl]acetamide A solution of indole-2-carboxylic acid (79 mg) and 1,1'-carbonyldiimidazole (80 mg) in dry tetrahydrofuran (2.0 mL) is stirred at ambient temperature for one hour, and a solution of (S)-(−)-N-[[2-oxo-3-[4-(4-piperidinyl)-3-fluorophenyl]-5-oxazolidinyl]methyl]acetamide (EXAMPLE 20, 150 mg) in dry tetrahydrofuran (6.0 mL) is added. The mixture is then stirred at ambient temperature for 19 hours, concentrated under reduced pressure, diluted with methylene chloride (20 mL), washed with saturated aqueous sodium bicarbonate (10 mL), water (10 mL) and saline (10 mL), dried over anhydrous sodium sulfate and concentrated under reduced pressure to give the crude product which is chromagraphed on silica gel (70–230 mesh, 10 g), eluting with methanol/methylene chloride (7.5/92.5). Pooling and concentration of those fractions with an $R_f$=0.67 by TLC (methanol/chloroform, 10/90) and recrystallization from chloroform/diethyl ether gives the title compound, mp 223–225° C.

EXAMPLE 24

(S)-(−)-N-[[3-[4-[1-(Isoxazole-5-carbonyl)-4-piperidinyl]-3-fluorophenyl]-2-oxo-5-oxazolidinyl]methyl]acetamide A solution of isoxazole-5-carboxylic acid (79 mg) and 1,1'-carbonyldiimidazole (80 mg) in dry tetrahydrofuran (2.0 mL) is stirred at ambient temperature for one hour, and a solution of (S)-(−)-N-[[2-oxo-3-[4-(4-piperidinyl)-3-fluorophenyl]-5-oxazolidinyl]methyl]acetamide (EXAMPLE 20, 150 mg) in dry tetrahydrofuran (6.0 mL) is added. The mixture is then stirred at ambient temperature for 19 hours, concentrated under reduced pressure, diluted with methylene chloride (20 mL), washed with saturated aqueous sodium bicarbonate (10 mL), water (10 mL) and saline (10 mL), dried over anhydrous sodium sulfate and concentrated under reduced pressure to give the crude product which is chromagraphed on silica gel (70–230 mesh, 10 g), eluting with methanol/methylene chloride (7.5/92.5). Pooling and concentration of those fractions with an $R_f$=0.67 by TLC (methanol/chloroform, 10/90) and recrystallization from chloroform/diethyl ether gives the title compound, mp 290–292° C.

EXAMPLE 25

(S)-(−)-N-[[3-[4-[1-(Methylsulfonyl)-4-piperidinyl]-3-fluorophenyl]-2-oxo-5-oxazolidinyl]methyl]acetamide A solution of (S)-(−)-N-[[2-oxo-3-[4-(4-piperidinyl)-3-fluorophenyl]-5-oxazolidinyl]methyl]acetamide (EXAMPLE 20, 125 mg) and pyridine (60 µL) in dry methylene chloride (1.9 mL) at 0° C. is treated with methanesulfonyl chloride (32 µL), and the resulting mixture was stirred at 0° C. for one hour and at ambient temperature for 16 hours. The reaction mixture is then diluted with methylene chloride (30 mL), washed with water (10 mL) and saline (10 mL), dried over anhydrous sodium sulfate and concentrated under reduced pressure, and the residue is recrystallized from methylene chloride/diethyl ether to give the title compound, mp 240–242° C.

EXAMPLE 26

(S)-(−)-4-[4-[5-[(Acetylamino)methyl]-2-oxo-3-oxazolidinyl]-2-fluorophenyl]-1-piperidinecarboxylic acid methyl ester A mixture of (S)-(−)-N-[[2-oxo-3-[4-(4-piperidinyl)-3-fluorophenyl]-5-oxazolidinyl]methyl]acetamide (EXAMPLE 20, 150 mg) and sodium bicarbonate (75 mg) in dry tetrahydrofuran (6 mL) at 0° C. under $N_2$ is treated with methyl chloroformate (38 µL), and the resulting mixture is stirred at 0° C. for one hour. The reaction is then diluted with ethyl acetate (20 mL), washed with water (10 mL) and saline (10 mL), dried over anhydrous magnesium sulfate and concentrated under reduced pressure, and the residue is recrystallized from methylene chloride/diethyl ether to give the title compound, mp 165–166° C.

EXAMPLE 27

(S)-(−)-N-[[3-[4-[1-(Cyanomethyl)-4-piperidinyl]-3-fluorophenyl]-2-oxo-5-oxazolidinyl]methyl]acetamide A mixture of (S)-(−)-N-[[2-oxo-3-[4-(4-piperidinyl)-3-fluorophenyl]-5-oxazolidinyl]methyl]acetamide (EXAMPLE 20, 150 mg), chloroacetonitrile (31 μL) and anhydrous potassium carbonate (124 mg) in dry acetonitrile (4 mL) under $N_2$ was stirred at ambient temperature for 20 hours, diluted with methylene chloride (20 mL), washed with water (10 mL) and saline (10 mL), dried over anhydrous sodium sulfate and concentrated under reduced pressure, and the residue is recrystallized from methylene chloride/diethyl ether to give the title compound, mp 165–167° C.

EXAMPLE 28

(S)-(–)-N-[[3-[4-[1-(2-Fluoroethyl)-4-piperidinyl]-3-fluorophenyl]-2-oxo-5-oxazolidinyl]methyl] acetamide Following the general procedure of EXAMPLE 27, and making non-critical variations but substituting 2-flouroethyl 4-toluenesulfonic acid ester for chloroacetonitrile and purifying the crude product by chromatography on silica gel (70–230 mesh, 30 g), eluting with methanol/methylene chloride, the title compound is obtained, mp 155–157° C.

EXAMPLE 29

(S)-(–)-N-[[3-[4-[1-(Formyl)-4-piperidinyl]-3-fluorophenyl]-2-oxo-5-oxazolidinyl]methyl] acetamide A mixture of (S)-(–)-3-[[2-oxo-3-[4-(4-piperidinyl)-3-fluorophenyl]-5-oxazolidinyl]methyl]acetamide (EXAMPLE 20, 150 mg), 1-(3-dimethylaminopropyl)-3-ethylcarbodiimide hydrochloride (171 mg) and formic acid (34 μL) in dry tetrahydrofuran (6 mL) is stirred at ambient temperature for one hour, diluted with methylene chloride (10 mL), washed with water (10 mL) and saline (10 mL), dried over anhydrous sodium sulfate and concentrated under reduced pressure, and the residue is recrystallized from methylene chloride/diethyl ether to give the title compound, mp 186–187° C.

EXAMPLE 30

(S)-(–)-4-[4-[5-[[(2,2-Dichloroacetyl)amino] methyl]-2-oxo-3-oxazolidinyl]-2-fluorophenyl]-1-piperidinecarboxylic acid 1,1-dimethylethyl ester A solution of (S)-(–)-4-[4-[5-(aminomethyl)-2-oxo-3-oxazolidinyl]-2-fluorophenyl]-1-piperidinecarboxylic acid 1,1-dimethylethyl ester (EXAMPLE 20, Step 8, 400 mg) in dry methylene chloride (4.1 mL) at 0° C. under $N_2$ is treated with triethylamine (0.21 mL) and dichloroacetyl chloride (0.11 mL), and the resulting mixture is stirred at 0° C. for three hours, diluted with methylene chloride (10 mL), washed with water (10 mL), saturated aqueous sodium bicarbonate (10 mL) and saline (10 mL), dried over anhydrous sodium sulfate and concentrated under reduced pressure to give the crude product which is then chromatographed on silica gel (70–230 mesh, 50 g), eluting with methanol/chloroform (5/95). Pooling and concentration of those fractions with an $R_f$=0.53 by TLC (methanol/chloroform, 10/90), trituration with methylene chloride/diethyl ether and filtration gives the title compound, mp 168–170° C.

EXAMPLE 31

(S)-(–)-2,2-Dichloro-N-[[2-oxo-3-[3-fluoro-4-(4-piperidinyl)phenyl]-5-oxazolidinyl]methyl] acetamide Following the general procedure of EXAMPLE 20, Step 10), and making non-critical variations but substituting (S)-(–)-4-[4-[5-[[(2,2-dichloroacetyl)amino]methyl]-2-oxo-3-oxazolidinyl]-2-fluorophenyl]-1-piperidinecarboxylic acid 1,1-dimethylethyl ester (EXAMPLE 30) for (S)-(–)-4-[4-[5-[(acetylamino)methyl]-2-oxo-3-oxazolidinyl]-2-fluorophenyl]-1-piperidinecarboxylic acid phenylmethyl ester, the title compound is obtained, NMR ($CDCl_3$, 400 MHz) 7.37, 7.22, 7.10, 5.99, 5.29, 4.83, 4.07, 3.78, 3.71, 3.30, 2.98, 2.83, 2.09, 1.81 δ.

EXAMPLE 32

(S)-(–)-2,2-Dichloro-N-[[2-oxo-3-[3-fluoro-4-[1-[(acetoxy)acetyl]-4-piperidinyl]phenyl]-5-oxazolidinyl]methyl]acetamide Following the general procedure of EXAMPLE 18, and making non-critical variations but substituting (S)-(–)-2,2-dichloro-N-[[2-oxo-3-[3-fluoro-4-(4-piperidinyl)phenyl]-5-oxazolidinyl]methyl]acetamide (EXAMPLE 31) for (S)-(–)-3-N-[4-(4-piperidinyl)phenyl]-5-acetamidomethyl-2-oxazolidinone and acetoxyacetyl chloride for benzyloxyacetyl chloride, the title compound is obtained, NMR ($CDCl_3$, 400 MHz) 7.42, 7.15, 6.24, 4.77, 4.04, 3.77, 3.68, 3.20, 3.07, 2.71, 2.20, 2.02, 1.88, 1.68 δ.

EXAMPLE 33

(S)-(–)-2,2-Dichloro-N-[[2-oxo-3-[3-fluoro-4-[1-(hydroxyacetyl)-4-piperidinyl]phenyl]-5-oxazolidinyl]methyl]acetamide A mixture of (S)-(–)-2,2-dichloro-N-[[2-oxo-3-[3-fluoro-4-[1-[(acetoxy)acetyl]-4-piperidinyl]phenyl]-5-oxazolidinyl]methyl]acetamide (EXAMPLE 32, 110 mg) and anhydrous potassium carbonate (60 mg) in methanol (8.8 mL) is stirred under $N_2$ at ambient temperature for one hour and then concentrated under reduced pressure and chromatographed on silica gel (70–230 mesh, 10 g), eluting with methanol/chloroform (10/90). Pooling and concentration of those fractions with an $R_f$=0.41 by TLC (methanol/chloroform, 10/90), repurification by radial chromatography (2000μ silica gel plate) eluting with methanol/methylene chloride, and trituration with chloroform/diethyl ether gives the title compound, NMR ($CDCl_3$, 400 MHz) 7.46, 7.39, 7.15, 5.99, 4.84, 4.74, 4.22, 4.09, 3.77, 3.61, 3.10, 2.79, 1.89, 1.65 δ.

EXAMPLE 34

(S)-(–)-N-[[2-Oxo-3-[3-fluoro-4-[1-[(acetoxy) acetyl]-4-piperidinyl]phenyl]-5-oxazolidinyl]methyl] acetamide Following the general procedure of EXAMPLE 18, and making non-critical variations but substituting (S)-(–)-N-[[2-oxo-3-[4-(4-piperidinyl)-3-fluorophenyl]-5-oxazolidinyl]methyl]acetamide (EXAMPLE 20,) for (S)-(–)-N-[[2-oxo-3-[4-(4-piperidinyl)phenyl]-5-oxazolidinyl] methyl]acetamide and acetoxyacetyl chloride for benzyloxyacetyl chloride, the title compound is obtained, NMR ($CDCl_3$, 400 MHz) 7.42, 7.15, 6.24, 4.77, 4.04, 3.77, 3.68, 3.20, 3.07, 2.71, 2.20, 2.02, 1.88, 1.68 δ.

EXAMPLE 35

(S)-(−)-N-[[2-Oxo-3-[4-(4-piperidinyl)-3,5-difluorophenyl]-5-oxazolidinyl]methyl]acetamide Step 1: 1-(3,5-Difluorophenyl)-2,2,5,5-tetramethyl-1-aza-2,5-disilacyclopentane Following the general procedure of Step 1 of EXAMPLE 20, and making non-critical variations but substituting 3,5-difluoroaniline for 3-fluoroaniline, the title compound is obtained, NMR (CDCl₃, 400 MHz) 6.38, 6.31, 0.87, 0.17 δ.

Step 2: 3,6-Dihydro-4-[4-amino-2,6-difluorophenyl]-1(2H)-pyridinecarboxylic acid 1,1-dimethylethyl ester Following the general procedure of Step 3 of EXAMPLE 20, and making non-critical variations but substituting 1-(3,5-difluorophenyl)-2,2,5,5-tetramethyl-1-aza-2,5-disilacyclopentane (EXAMPLE 35, Step 1) for 1-(3-fluorophenyl)-2,2,5,5-tetramethyl-1-aza-2,5-disilacyclopentane, the title compound is obtained, mp 134–135° C.

Step 3: 4-[4-[[(Phenylmethoxy)carbonyl]amino-2,6-difluorophenyl]-1-piperidinecarboxylic acid 1,1-dimethylethyl ester Following the general procedure of Step 4 of EXAMPLE 20, and making non-critical variations but substituting 3,6-dihydro-4-[4-amino-2,6-difluorophenyl]-1(2H)-pyridinecarboxylic acid 1,1-dimethylethyl ester (EXAMPLE 35, Step 2) for 3,6-dihydro-4-[4-amino-2-fluorophenyl]-1(2H)-pyridinecarboxylic acid 1,1-dimethylethyl ester and purifying the crude product by trituration with ethyl acetate/hexane and filtration, the title compound is obtained, mp 153–155° C.

Step 4: (R)-(−)-4-[4-[5-(Hydroxymethyl)-2-oxo-3-oxazolidinyl]-2,6-difluorophenyl]-1-piperidinecarboxylic acid 1,1-dimethylethyl ester Following the general procedure of Step 3 of EXAMPLE 17, and making non-critical variations but substituting 4-[4-[[(phenylmethoxy)carbonyl]amino-2,6-difluorophenyl]-1-piperidinecarboxylic acid 1,1-dimethylethyl ester (EXAMPLE 35, Step 3) for 3,6-dihydro-4-[4-[[(phenylmethoxy)carbonyl]amino]phenyl]-1(2H)-pyridinecarboxylic acid phenylmethyl ester, the title compound is obtained, NMR (CDCl₃, 400 MHz) 7.11, 4.75, 4.22, 3.96, 3.75, 3.06, 2.76, 2.50, 1.98, 1.65, 1.48 δ.

Step 5: (R)-(−)-4-[4-[5-[[(Methylsulfonyl)oxy]methyl]-2-oxo-3-oxazolidinyl]-2,6-difluorophenyl]-1-piperidinecarboxylic acid 1,1-dimethylethyl ester Following the general procedure of Step 4 of EXAMPLE 17, and making non-critical variations but substituting (R)-(−)-4-[4-[5-(hydroxymethyl)-2-oxo-3-oxazolidinyl]-2,6-difluorophenyl]-1-piperidinecarboxylic acid 1,1-dimethylethyl ester (EXAMPLE 35, Step 4) for (R)-(−)-3,6-dihydro-4-[4-[5-(hydroxymethyl)-2-oxo-3-oxazolidinyl]phenyl]-1(2H)-pyridinecarboxylic acid phenylmethyl ester, the title compound is obtained, mp 125–126° C.

Step 6: (R)-(−)-4-[4-[5-(Azidomethyl)-2-oxo-3-oxazolidinyl]-2,6-difluorophenyl]-1-piperidinecarboxylic acid 1,1-dimethylethyl ester Following the general procedure of step 7 of EXAMPLE 20, and making non-critical variations but substituting (R)-(−)-[4-[5-[[(methylsulfonyl)oxy]methyl]-2-oxo-3-oxazolidinyl]-2,6-difluorophenyl)-1-piperidinecarboxylic acid 1,1-dimethylethyl ester (EXAMPLE 35, Step 5) for (R)-(−)-4-[4-[5-[[(methylsulfonyl)oxy]methyl]-2-oxo-3-oxazolidinyl]-2-fluorophenyl]-1-piperidinecarboxylic acid 1,1-dimethylethyl ester, the title compound is obtained, mp 125–127° C.

Step 7: (S)-(−)-4-[4-[5-[(Acetylamino)methyl]-2-oxo-3-oxazolidinyl]-2,6-difluorophenyl]-1-piperidinecarboxylic acid 1,1-dimethylethyl ester A mixture of (R)-(−)-4-[4-(5-(azidomethyl)-2-oxo-3-oxazolidinyl]-2,6-difluorophenyl]-1-piperidinecarboxylic acid 1,1-dimethylethyl ester ((EXAMPLE 35, Step 6, 1.51 g) and 10% palladium on carbon (367 mg) in methanol (35 mL) is stirred under a hydrogen atmosphere (balloon) for 18 hours, the catalyst is removed by filtration through Celite and the filtrate is concentrated under reduced pressure to give the 5-aminomethyl-2-oxazolidinone intermediate (R_f= 0.10 by TLC, methanol/chloroform, 5/95). A solution of this intermediate (1.28 g) and pyridine (2.51 mL) in dry methylene chloride (31 mL) at 0° C. under N₂ is treated with acetic anhydride (1.47 mL), and the resulting solution is allowed to warm to ambient temperature with stirring over 1.5 hours. The mixture is then diluted with methylene chloride (15 mL), washed with water (10 mL), saturated aqueous sodium bicarbonate (2×10 mL) and saline (10 mL), dried over anhydrous sodium sulfate and concentrated under reduced pressure to give the crude product which is chromatographed on silica gel (70–230 mesh, 150 g), eluting with a gradient of methanol/methylene chloride (1/99–4/96). Pooling and concentration of those fractions with an R_f=0.31 by TLC (methanol/chloroform, 5/95), trituration with diethyl ether and filtration gives the title compound, NMR (CDCl₃, 400 MHz) 7.06, 6.56, 4.78, 4.22, 4.00, 3.74, 3.65, 3.05, 2.75, 2.02, 1.96, 1.64, 1.47 δ.

Step 8: (S)-(−)-N-[[2-Oxo-3-[4-(4-piperidinyl)-3,5-difluorophenyl]-5-oxazolidinyl]methyl]acetamide A mixture of (S)-(−)-4-[4-[5-[(acetylamino)methyl]-2-oxo-3-oxazolidinyl]-2,6-difluorophenyl]-1-piperidinecarboxylic 1,1-dimethylethyl ester ((EXAMPLE 35, Step 7, 847 mg) and trifluoroacetic acid (12 mL) maintained at 0° C. under N₂ is stirred for two hours and then concentrated under reduced pressure to remove excess trifluoroacetic acid. The residue is diluted with saturated aqueous potassium carbonate (70 mL) and methylene chloride (50 mL), and the layers are separated. The aqueous phase is extracted with methylene chloride (2×50 mL), and the combined organic phase is dried over anhydrous sodium sulfate, concentrated under reduced pressure, triturated with diethyl ether and recrystallized from ethyl acetate to give the title compound, NMR (CDCl₃, 400 MHz) 7.08, 6.10, 4.78, 4.00, 3.74, 3.64, 3.19, 3.07, 2.72, 2.03, 1.99, 1.68 δ.

EXAMPLE 36

(S)-(−)-N-[[-3-[4-[1-[(Benzyloxy)acetyl]-4-piperidinyl]-3,5-difluorophenyl]-2-oxo-5-oxazolidinyl]methyl]acetamide Following the general procedure of EXAMPLE 18, and making non-critical variations but substituting (S)-(−)-N-[[2-oxo-3-[4-(4-piperidinyl)-3,5-difluorophenyl]-5-oxazolidinyl]methyl]acetamide (EXAMPLE 35) for (S)-(−)-N-[[2-oxo-3-[4-(4-piperidinyl)phenyl]-5-oxazolidinyl]methyl]acetamide, the title compound is obtained, mp 169° C.–171° C.

EXAMPLE 37

(S)-(−)-N-[[3-[4-[1-(Hydroxyacetyl)-4-piperidinyl]-3,5-difluorophenyl]-2-oxo-5-oxazolidinyl]methyl]acetamide A mixture of (S)-(−)-N-[[3-[4-[1-[(benzyloxy)acetyl]-4-piperidinyl]-3,5-difluorophenyl]-2-oxo-5-oxazolidinyl]methyl]acetamide (EXAMPLE 36, 207 mg) and 10% palladium-on-carbon (100 mg) in methanol (9 mL) is shaken on a Parr apparatus under a hydrogen atmosphere at 40 psi for 20 hours, the catalyst is removed by filtration through Celite and the filtrate is concentrated under reduced pressure to give the crude product which is chromatographed on silica gel (230–400 mesh, 20 g), eluting with a gradient of methanol/methylene chloride (5/95–10/90). Pooling and concentration of those fractions with an $R_f$=0.26 by TLC (methanol/chloroform, 10/90) and recrystallization from methylene chloride/diethyl ether gives the title compound, NMR (CDCl$_3$, 400 MHz) 7.07, 6.80, 4.78, 4.69, 4.18, 3.99, 3.74, 3.63, 3.60, 3.16, 3.06, 2.90, 2.72, 2.00, 1.97, 1.75 δ.

EXAMPLE 38

(S)-(–)-N-[[2-Oxo-3-[4-(3,6-dihydro-2H-pyridin-4-yl)-3-fluorophenyl]-5-oxazolidinyl]methyl]acetamide Step 1: (S)-(–)-4-[4-[5-[(Acetylamino)methyl]-2-oxo-3-oxazolidinyl]-2-fluorophenyl]-3,6-dihydro-1(2H)-pyridinecarboxylic acid 1,1-dimethylethyl ester A mixture of (S)-(–)-N-[[3-[4-trimethylstannyl-3-fluorophenyl]-2-oxo-5-oxazolidinyl]methyl]acetamide (690 mg), 3,6-dihydro-4-[[(trifluoromethyl)sulfonyl]oxy]-1(2H)-pyridinecarboxylic acid 1,1-dimethylethyl ester (step 2 of EXAMPLE 20, 500 mg), tris(dibenzylideneacetone)dipalladium(0) (14 mg) and triphenylarsine (37 mg) in N-methyl-2-pyrrolidinone (7.5 mL) is degassed, stirred under N$_2$ at ambient temperature for 4.5 days, diluted with ethyl acetate, washed with water (3×40 mL) and saline (20 mL), dried over anhydrous magnesium sulfate and concentrated under reduced pressure. The residue is chromatographed on silica gel (230–400 mesh, 120 g), eluting with a gradient of methanol/methylene chloride (1/99–2/98), and those fraction having an $R_f$=0.27 by TLC (methanol/chloroform, 2×5/95) are pooled and concentrated to give the title compound, $^1$H NMR (CDCl$_3$, 400 MHz) 7.39, 7.22, 7.13, 7.01, 5.92, 4.82, 4.06, 3.80, 3.67, 3.61, 2.47, 2.03, 1.49 δ.

Step 2: (S)-(–)-N-[2-Oxo-3-[4-(3,6-dihydro-2H-pyridin-4-yl)-3-fluorophenyl]-5-oxazolidinyl]methyl]acetamide A solution of (S)-(–)-4-[4-[5-[(acetylamino)methyl]-2-oxo-3-oxazoldinyl]-2-fluorophenyl]-3,6-dihydro-1(2H)-pyridinecarboxylic acid 1,1-dimethylethyl ester (EXAMPLE 38, Step 1, 1.00 g) in dry methylene chloride (9.2 mL) at 0° C. under N$_2$ is treated with trifluoroacetic acid (2.3 mL) over one minute, and the resulting mixture is stirred at 0° C. for three hours and added slowly to saturated aqueous potassium carbonate (30 mL) to neutralize excess trifluoroacetic acid. The resultant slurry is filtered and the precipitate is chromatographed on silica gel (70–230 mesh, 60 g), eluting with ammonium hydroxide/methanol/methylene chloride (0.25/19.75/80). Those fractions with an $R_f$=0.08 by TLC (methanol/chloroform, 20/80) are pooled and concentrated under reduced pressure to give the title compound, $^1$H NMR (MeOH-d$_4$, 400 MHz) 7.47, 7.33, 7.25, 6.02, 4.80, 4.15, 3.83, 3.58, 3.47, 3.04, 2.46, 1.98 δ.

EXAMPLE 39

(S-(–)-N-[[2-Oxo-3-[3-fluoro-4-[1-[(acetoxy)acetyl]-3,6-dihydro-2H-pyridin-4-yl]phenyl]-5-oxazolidinyl]methyl]acetamide Following the general procedure of EXAMPLE 18, and making non-critical variations but substituting (S)-(–)-N-[[2-oxo-3-[4-(3,6-dihydro-2H-pyridin-4-yl)-3-fluorophenyl]-5-oxazolidinyl]methyl]acetamide (EXAMPLE 38) for (S)-(–)-N-[[2-oxo-3-[4-(4-piperidinyl)phenyl]-5-oxazolidinyl]methyl]acetamide and acetoxyacetyl chloride for benzyloxyacetyl chloride, the title compound is obtained, mp 188–191° C.

EXAMPLE 40

(S)-(–)-N-[[3-[4-[1-(Hydroxyacetyl)-3,6-dihydro-2H-pyridin-4-yl]-3-fluorophenyl]-2-oxo-5-oxazolidinyl]methyl]acetamide A mixture of (S)-(–)-N-[[2-oxo-3-[3-fluoro-4-[1-[(acetoxy)acetyl]-3,6-dihydro-2H-pyridin-4-yl]phenyl]-5-oxazolidinyl]methyl]acetamide (EXAMPLE 39, 475 mg) and anhydrous potassium carbonate (303 mg) in methanol (44 mL) is stirred under N$_2$ at ambient temperature for 1.5 hours and then adjusted to pH 7 with aqueous hydrochloric acid (1 M) and concentrated under reduced pressure. The residue is chromatographed on silica gel (230–400 mesh, 40 g), eluting with a gradient of methanol/chloroform (5/95–10/90), and those fractions with an $R_f$=0.21 by TLC (methanol/chloroform, 10/90) are pooled and concentrated under reduced pressure. The resulting foam is then triturated with methylene chloride/diethyl ether and the precipitate filtered to give the title compound, Anal. calcd for C$_{19}$H$_{22}$N$_3$O$_5$F: C, 58.31; H, 5.67; N, 10.74. Found: C, 58.15; H, 5.64; N, 10.72.

EXAMPLE 41

(5S)-N-[[3-[3-Fluoro-4-[1-(phenylmethyl)-3-pyrrolidinyl]phenyl]-2-oxo-5-oxazolidinyl]methyl]acetamide Step 1: (S)-(–)-N-[[3-[4-Ethenyl-3-fluorophenyl]-2-oxo-5-oxazolidinyl]methyl]acetamide A mixture of (S)-(–)-N-[[3-[4-iodo-3-fluorophenyl]-2-oxo-5-oxazolidinyl]methyl]acetamide (5.45 g), vinyltributyltin (5.48 g) and bis(triphenylphosphine)palladium(II) chloride (303 mg) in 1,4-dioxane (72 mL) under N$_2$ is degassed, heated up to reflux, refluxed for seven hours, cooled to ambient temperature and stirred for 12 hours. The mixture is then diluted with ethyl acetate (40 mL) and water (50 mL) and the layers are separated. The aqueous phase is extracted with ethyl acetate (2×30 mL), and the combined organic phase is washed with saline (40 mL), dried over anhydrous magnesium sulfate, concentrated under reduced pressure and triturated with diethyl ether. The resultant precipitate is filtered to give the title compound, mp 165–166° C.

Step 2: (5S)-N-[[3-[3-Fluoro-4-[1-(phenylmethyl)-3-pyrrolidinyl]phenyl]-2-oxo-5-oxazolidinyl]methyl]acetamide A solution of (S)-(–)-N-[[3-[4-vinyl-3-fluorophenyl]-2-oxo-5-oxazolidinyl]methyl]acetamide (EXAMPLE 41, Step 1, 3.50 g) and trifluoroacetic acid (0.23 mL) in dry methylene chloride under N$_2$ is treated with a solution of N-benzyl-N-(methoxymethyl) trimethylsilylmethylamine (6.10 g) in dry methylene chloride (50 mL) dropwise over 4.5 hours, and the resulting solution was stirred at ambient temperature for 17 hours. The reaction mixture is then washed with saturated aqueous sodium bicarbonate (30 mL), water (30 mL) and saline (30 mL), dried over anhydrous sodium sulfate and concentrated under reduced pressure to give a residue which is chromatographed on silica gel (230–400 mesh, 350 g), eluting with a gradient of methanol/methylene chloride (1/99–10/90). Pooling and concentration of those fractions with an $R_f$=0.19 by TLC (methanol/chloroform, 10/90) and trituration with methanol/diethyl ether gives the title compound, NMR (CDCl$_3$, 400 MHz) 7.35, 7.25, 7.13, 6.08, 4.78, 4.03, 3.76, 3.69, 3.62, 2.97, 2.78, 2.56, 2.33, 2.02, 1.85 δ.

EXAMPLE 42

(5S)-N-[[3-[3-Fluoro-4-(3-pyrrolidinyl)phenyl]-2-oxo-5-oxazolidinyl]methyl]acetamide A mixture of (5S)-N-[[3-[3-fluoro-4-[1-(phenylmethyl)-3-pyrrolidinyl]phenyl]-2-oxo-5-oxazolidinyl]methyl]

acetamide (EXAMPLE 41, 1.09 g) and 20% palladium hydroxide on carbon (545 mg) in methanol (30 mL) is shaken on the Parr apparatus under a hydrogen atmosphere at 40 psi for 1.5 hours and at 10 psi for 18 hours. The catalyst is then removed by filtration through Celite, and the filtrate is concentrated under reduced pressure to give the title compound, NMR (CDCl$_3$, 400 MHz) 7.39, 7.24, 7.11, 6.35, 4.78, 4.04, 3.77, 3.67, 3.44, 3.37, 3.18, 3.11, 2.88, 2.21 2.02, 1.86 δ.

EXAMPLE 43

(5S)-N-[[3-[3-Fluoro-4-[1-[benzyloxy)acetyl]-3-pyrrolidinyl]phenyl]-2-oxo-5-oxazolidinyl]methyl] acetamide Following the general procedure of EXAMPLE 18, and making non-critical variations but substituting (5S)-N-[[3-[3-fluoro-4-(3-pyrrolidinyl)phenyl]-2-oxo-5-oxazolidinyl] methyl]acetamide (EXAMPLE 42) for (S)-(–)-N-[[2-oxo-3-[4-(4-piperidinyl)phenyl]-5-oxazolidinyl]methyl] acetamide, the title compound is obtained, HRMS calculated for C$_{25}$H$_{28}$N$_3$O$_5$F: 470.2091. Found: 470.2106.

EXAMPLE 44

(5S)-N-[[3-[3-Fluoro-4-[1-(hydroxyacetyl)-3-pyrrolidinyl]phenyl]-2-oxo-5-oxazolidinyl]methyl] acetamide Following the general procedure of EXAMPLE 22, and making non-critical variations but substituting (5S)-N-[[3-[3-fluoro-4-[1-(benzyloxy)acetyl]-3-pyrrolidinyl]phenyl]-2-oxo-5-oxazolidinyl]methyl]acetamide (EXAMPLE 43) for (S)-(–)-N-[[3-[4-[1-[(benzyloxy)acetyl]-4-piperidinyl]-3-fluorophenyl]-2-oxo-5-oxazolidinyl]methyl]acetamide, the title compound is obtained, FAB-HRMS calculated for C$_{18}$H$_{22}$N$_3$O$_5$F+H: 380.1622. Found: 380.1625.

EXAMPLE 45

(5S)-N-[[3-[3-Fluoro-4-[1-(formyl)-3-pyrrolidinyl] phenyl]-2-oxo-5-oxazolidinyl]methyl]acetamide Following the general procedure of EXAMPLE 29, and making non-critical variations but substituting (5S)-N-[[3-[3-fluoro-4-(3-pyrrolidinyl)phenyl]-2-oxo-5-oxazolidinyl] methyl]acetamide (EXAMPLE 44) for (S)-(–)-N-[[2-oxo-3-[4-(4-piperidinyl)-3-fluorophenyl]-5-oxazolidinyl]methyl] acetamide, the title compound is obtained, HRMS calculated for C$_{17}$H$_{20}$FN$_3$O$_4$: 349.1438. Found: 349.1444.

EXAMPLE 46

(5S)-3-[4-[5-[(Acetylamino)methyl]-2-oxo-3-oxazolidinyl]-2-fluorophenyl]-1-pyrrolidinecarboxylic acid methyl ester Following the general procedure of EXAMPLE 26, and making non-critical variations but substituting (5S)-N-[[3-[3-fluoro-4-(3-pyrrolidinyl)phenyl]-2-oxo-5-oxazolidinyl] methyl]acetamide (EXAMPLE 44) for (S)-(–)-N-[[2-oxo-3-[(4-piperidinyl)-3-fluorophenyl]-5-oxazolidinyl]methyl] acetamide, the title compound is obtained, HRMS calculated for C$_{18}$H$_{22}$FN$_3$O$_5$: 379.1543. Found: 379.1546.

EXAMPLE 47

(S)-(–)-N-[[3-[4-(3,6-Dihydro-2H-pyran-4-yl)-3-fluorophenyl]-2-oxo-5-oxazolidinyl]methyl] acetamide Step 1: 3,6-Dihydro-2H-pyran-4-yl trifluoromethanesulfonic acid ester Following the general procedure of Step 2 of EXAMPLE 20, and making non-critical variations but substituting tetrahydropyran-4-one for 1-(1,1-dimethylethoxycarbonyl)-4-piperidone, the title compound is obtained, $^1$H NMR (CDCl$_3$, 400 MHz) 5.82, 4.27, 3.90, 2.47 δ.

Step 2: 3-Fluoro-4-(3,6-dihydro-2H-pyran-4-yl) benzenamine

Following the general procedure of Step 3 of EXAMPLE 20, and making non-critical variations but substituting 3,6-dihydro-2H-pyran-4-yl trifluoromethanesulfonic acid ester (EXAMPLE 47, Step 1) for 3,6-dihydro-4-[[(trifluoromethyl)sulfonyl]oxy]-1(2H)-pyridinecarboxylic acid 1,1-dimethylethyl ester, the title compound is obtained, mp 86° C.–88° C.

Step 3: 3-Fluoro-4-(3,6-dihydro-2H-pyran-4-yl) benzenaminecarboxylic acid phenylmethyl ester A mixture of 3-fluoro-4-(3,6-dihydro-2H-pyran-4-yl) benzenamine (EXAMPLE 47, Step 2, 2.28 g) and sodium bicarbonate (1.98 g) in tetrahydrofuran (59 mL) is treated with benzyl chloroformate (1.85 mL), and the resulting slurry is stirred at ambient temperature for six hours. The mixture is then washed with water (50 mL), the aqueous phase is extracted with methylene chloride (50 mL), and the combined organic phase is washed with saline (25 mL), dried over anhydrous sodium sulfate and concentrated under reduced pressure. The residue is then chromatographed on silica gel (70–230 mesh, 80 g), eluting with ethyl acetate/hexane (15/85), and those fractions with an R$_f$=0.45 by TLC (ethyl acetate/hexane, 25/75) are pooled and concentrated to give the title compound, mp 75–76° C.

Step 4: (R)-(–)-3-[3-Fluoro-4-(3,6-dihydro-2H-pyran-4-yl) phenyl]-5-hydroxymethyl-2-oxazolidinone Following the general procedure of Step 3 of EXAMPLE 17, and making non-critical variations but substituting 3-fluoro-4-(3,6-dihydro-2H-pyran-4-yl) benzenaminecarboxylic acid phenylmethyl ester (EXAMPLE 47, Step 3) for 3,6-dihydro-4-[4-[[(phenylmethoxy)carbonyl]amino]phenyl]-1(2H)-pyridinecarboxylic acid phenylmethyl ester, the title compound is obtained, mp 127–130° C.

Step 5: (R)-(–)-3-[3-Fluoro-4-(3,6-dihydro-2H-pyran-4-yl) phenyl]-5-[[(methylsulfonyl)oxy]methyl]-2-oxazolidinone Following the general procedure of Step 4 of EXAMPLE 17, and making non-critical variations but substituting (R)-(–)-3-[3-fluoro-4-(3,6-dihydro-2H-pyran-4-yl)phenyl]-5-hydroxymethyl-2-oxazolidinone (EXAMPLE 47, Step 4) for (R)-(–)-3,6-dihydro-4-[4-[5-(hydroxymethyl)-2-oxo-3-oxazolidinyl]phenyl]-1(2H)-pyridinecarboxylic acid phenylmethyl ester, the title compound is obtained, mp 166–169° C. (decomp.).

Step 6: (S)-(–)-N-[[3-[(3,6-Dihydro-2H-pyran-4-yl)-3-fluorophenyl]-2-oxo-5-oxazolidinyl]methyl]acetamide Following the general procedure of Step 5 of EXAMPLE 17, and making non-critical variations but substituting (R)-(–)-3-[3-fluoro-4-(3,6-dihydro-2H-pyran-4-yl)phenyl]-5-[[(methylsulfonyl)oxy]methyl]-2-oxazolidinone (EXAMPLE 47, Step 5) for (R)-(–)-3,6-dihydro-4-[4-[5-[[(methylsulfonyl)oxy]methyl]-2-oxo-3-oxazolidinyl] phenyl]-1(2H)-pyridinecarboxylic acid phenylmethyl ester, the title compound is obtained, mp 148–151° C.

EXAMPLE 48

(S)-(–)-N-[[3-[4-[Tetrahydro-2H-pyran-4-yl]-3-fluorophenyl]-2-oxo-5-oxazolidinyl]methyl] acetamide A mixture of (S)-(–)-N-[[3-[4-(3,6-dihydro-2H-pyran-4-yl)-3-fluorophenyl]-2-oxo-5-oxazolidinyl]methyl]

acetamide (EXAMPLE 47, 1.00g) and 10% palladium-on-carbon (637 mg) in methanol (60 mL) is shaken on a Parr apparatus under a hydrogen atmosphere at 40 psi for three hours, the catalyst is removed by filtration through Celite and the filtrate is concentrated under reduced pressure to give the title compound, mp 191–192° C.

EXAMPLE 49

(S)-(–)-N-[[3-[4-(3,6-Dihydro-2H-thiopyran-4-yl)-3-fluorophenyl]-2-oxo-5-oxazolidinyl]methyl] acetamide Step 1: 3,6-Dihydro-2H-thiopyran-4-yl trifluoromethanesulfonic acid ester Following the general procedure of Step 2 of EXAMPLE 20, and making non-critical variations but substituting tetrahydrothiopyran-4-one for 1-(1,1-dimethylethoxycarbonyl)-4-piperidone, the title compound is obtained, NMR (CDCl$_3$, 400 MHz) 6.01, 3.30, 2.86, 2.62 δ.

Step 2: 3-Fluoro-4-(3,6-dihydro-2H-thiopyran-4-yl)benzenamine

Following the general procedure of Step 3 of EXAMPLE 20, and making non-critical variations but substituting 3,6-dihydro-2H-thiopyran-4-yl trifluoromethanesulfonic acid ester (EXAMPLE 49, Step 1) for 3,6-dihydro-4-[[(trifluoromethyl)sulfonyl]oxy]-1(2H)-pyridinecarboxylic acid 1,1-dimethylethyl ester, the title compound is obtained, NMR (CDCl$_3$, 400 MHz) 6.98, 6.40, 6.35, 5.94, 3.73, 3.31, 2.84, 2.62 δ.

Step 3: 3-Fluoro-4-(3,6-dihydro-2H-thiopyran-4-yl)benzenaminecarboxylic acid phenylmethyl ester Following the general procedure of Step 3 of EXAMPLE 47, and making non-critical variations but substituting 3-fluoro-4-(3,6-dihydro-2H-thiopyran-4-yl)benzenamine (EXAMPLE 49, Step 2) for 3-fluoro-4-(3,6-dihydro-2H-pyran-4-yl)benzenamine, the title compound is obtained, mp 99–101° C.

Step 4: (R)-(–)-3-[3-Fluoro-4-(3,6-dihydro-2H-thiopyran-4-yl)phenyl]-5-hydroxymethyl-2-oxazolidinone Following the general procedure of Step 3 of EXAMPLE 17, and making non-critical variations but substituting 3-fluoro-4-(3,6-dihydro-2H-thiopyran-4-yl)benzenaminecarboxylic acid phenylmethyl ester (EXAMPLE 49, Step 3) for 3,6-dihydro-4-[4-[[(phenylmethoxy)carbonyl]amino]phenyl]-1(2H)-pyridinecarboxylic acid phenylmethyl ester, the title compound is obtained, mp 119–122° C.

Step 5: (R)-(–)-3-[3-Fluoro-4-(3,6-dihydro-2H-thiopyran-4-yl)phenyl]-5-[[(methylsulfonyl)oxy]methyl]-2-oxazolidinone Following the general procedure of Step 4 of EXAMPLE 17, and making non-critical variations but substituting (R)-(–)-3-[3-fluoro-4-(3,6-dihydro-2H-thiopyran-4-yl)phenyl]-5-hydroxymethyl-2-oxazolidinone (EXAMPLE 49, Step 4) for (R)-(–)-3,6-dihydro-4-[4-[5-(hydroxymethyl)-2-oxo-3-oxazolidinyl]phenyl]-1(2H)-pyridinecarboxylic acid phenylmethyl ester, the title compound is obtained, mp 138–141° C.

Step 6: (S)-(–)-N-[[3-[4-(3,6-Dihydro-2H-thiopyran-4-yl)-3-fluorophenyl]-2-oxo-5-oxazolidinyl]methyl]acetamide Following the general procedure of Step 5 of EXAMPLE 17, and making non-critical variations but substituting (R)-(–)-3-[3-fluoro-4-(3,6-dihydro-2H-thiopyran-4 yl)phenyl]-5-[[(methylsulfonyl)oxy]methyl]-2-oxazolidinone (EXAMPLE 49, Step 5) for (R)-(–)-3,6-dihydro-4-[4-[5-[[(methylsulfonyl)oxy]methyl]-2-oxo-3-oxazolidinyl]phenyl]-1(2H)-pyridinecarboxylic acid phenylmethyl ester, the title compound is obtained, mp 187–189° C.

EXAMPLE 50

(S)-(–)-N-[[3-[4-(3,6-Dihydro-2H-thiopyran-4-yl)-3-fluorophenyl]-2-oxo-5-oxazolidinyl]methyl] acetamide S,S-dioxide A solution of (S)-(–)-N-[[3-[4-(3,6-dihydro-2H-thiopyran-4-yl)-3-fluorophenyl]-2-oxo-5-oxazolidinyl]methyl]acetamide (EXAMPLE 49, 300 mg) in water/acetone (25%, 17 mL) is treated with N-methylmorpholine N-oxide (301 mg) followed by osmium tetroxide (2.5 wt % in t-butanol, 0.54 mL), and the resulting mixture is stirred at ambient temperature overnight. The mixture is then quenched with saturated aqueous sodium bisulfite (10 mL) and extracted with methylene chloride (2×20 mL). The combined organic phase is washed with saline (10 mL), dried over sodium sulfate and concentrated under reduced pressure to give the crude product which is then chromatographed on silica gel (70–230 mesh, 30 g), eluting with a gradient of methanol/methylene chloride (3/97–5/95). Pooling of fractions with an R$_f$=0.49 by TLC (methanol/chloroform, 10/90) and trituration with methylene chloride/diethyl ether gives the title compound, mp 181–182° C.

EXAMPLE 51

(S)-(–)-N-[[3-[3-Fluoro-4-(tetrahydro-2H-thiopyran-4-yl)phenyl]-2-oxo-5-oxazolidinyl]methyl]acetamide S,S-dioxide Following the general procedure of EXAMPLE 48, and making non-critical variations but substituting (S)-(–)-N-[[3-[4-(3,6-dihydro-2H-thiopyran-4-yl)-3-fluorophenyl]-2-oxo-5-oxazolidinyl]methyl]acetamide S,S-dioxide (EXAMPLE 50) for (S)-(–)-N-[[3-[4-(3,6-dihydro-2H-pyran-4-yl)-3-fluorophenyl]-2-oxo-5-oxazolidinyl]methyl] acetamide and recrystallizing the product from methylene chloride/diethyl ether, the title compound is obtained, mp 199–200° C.

EXAMPLE 52

(S)-(–)-N-[[3-[4-(3,6-Dihydro-2H-pyran-4-yl) phenyl]-2-oxo-5-oxazolidinyl]methyl]acetamide Step 1: 4-[4-(Hydroxy)tetrahydro-2H-pyran-4-yl]benzenaminecarboxylic acid phenylmethyl ester Following the general procedure of Step 1 of EXAMPLE 17, and making non-critical variations but substituting tetrahydropyran-4-one for N-(carbobenzyloxy)-4-piperidone, the title compound is obtained, mp 143–145° C.

Step 2: 4-(3,6-Dihydro-2H-pyran-4-yl) benzenaminecarboxylic acid phenylmethyl ester Following the general procedure of Step 2 of EXAMPLE 17, and making non-critical variations but substituting 4-[4-(hydroxy)tetrahydro-2H-pyran-4-yl] benzenaminecarboxylic acid phenylmethyl ester (EXAMPLE 52, Step 1) for 4-hydroxy-4-[4-[[(phenylmethoxy)carbonyl]amino]phenyl]-1-piperidinecarboxylic acid phenylmethyl ester and recrystallizing the crude product from ethyl acetate/hexane, the title compound is obtained, mp 145–148° C.

Step 3: (R)-(–)-3-[4-(3,6-Dihydro-2H-pyran-4-yl)phenyl]-5-hydroxymethyl-2-oxazolidinone Following the general procedure of Step 3 of EXAMPLE 17, and making non-critical variations but substituting 4-(3,6-dihydro-2H-pyran-4-yl)benzenaminecarboxylic acid phenylmethyl ester (EXAMPLE 52, Step 2) for 3,6-dihydro-4-[4-[[(phenylmethoxy)carbonyl]amino]phenyl]-1(2H)-pyridinecarboxylic acid phenylmethyl ester and triturating the crude product with ethyl acetate/hexane (50/50), the title compound is obtained, Anal. Calcd for $C_{15}H_{17}NO_4$: C: 65.44; H, 6.22; N, 5.09. Found: C: 65.05; H, 6.04; N, 4.91.

Step 4: (R)-(–)-3-[4-(3,6-Dihydro-2H-pyran-4-yl)phenyl]-5-[[(methylsulfonyl)oxymethyl]-2-oxazolidinone Following the general procedure of Step 4 of EXAMPLE 17, and making non-critical variations but substituting (R)-(–)-3-[4-(3,6-dihydro-2H-pyran-4-yl)phenyl]-5-hydroxymethyl-2-oxazolidinone (EXAMPLE 52, Step 3) for (R)-(–)-3,6-dihydro-4-[4-[5-(hydroxymethyl)-2-oxo-3-oxazolidinyl]phenyl]-1(2H)-pyridinecarboxylic acid phenylmethyl ester, the title compound is obtained, mp 182–184° C.

Step 5: (S)-(–)-N-[[3-[4-(3,6-Dihydro-2H-pyran-4-yl)phenyl]-2-oxo-5-oxazolidinyl]methyl]acetamide Following the general procedure of Step 5 of EXAMPLE 17, and making non-critical variations but substituting (R)-(–)-3-[4-(3,6-dihydro-2H-pyran-4-yl)phenyl]-5-[[(methylsulfonyl)oxy]methyl]-2-oxazolidinone (EXAMPLE 52, Step 4) for (R)-(–)-3,6-dihydro-4-[4-[5-[[(methylsulfonyl)oxy]methyl]-2-oxo-3-oxazolidinyl]phenyl]-1(2H)-pyridinecarboxylic acid phenylmethyl ester, the title compound is obtained, NMR (CDCl$_3$, 400 MHz) 7.45, 7.36, 6.63, 6.09, 4.77, 4.31, 4.05, 3.92, 3.80, 3.65, 2.48, 2.01 δ.

EXAMPLE 53

(S)-(–)-N-[[3-[4-Tetrahydro-2H-pyran-4-yl]phenyl]-2-oxo-5-oxazolidinyl]methyl]acetamide Following the general procedure of EXAMPLE 48, and making non-critical variations but substituting (S)-(–)-N-[[3-[4-(3,6-dihydro-2H-pyran-4-yl)phenyl]-2-oxo-5-oxazolidinyl]methyl]acetamide (EXAMPLE 52) for (S)-(–)-N-[[3-[4-(3,6-dihydro-2H-pyran-4-yl)-3-fluorophenyl]-2-oxo-5-oxazolidinyl]methyl]acetamide, the title compound is obtained, mp 185° C.–187° C.

EXAMPLE 54

(S)-(–)-N-[[3-[4-(3,6-Dihydro-2H-thiopyran-4-yl) phenyl]-2-oxo-5-oxazolidinyl]methyl]acetamide Step 1: 4-[4-(Hydroxy)tetrahydro-2H-thiopyran-4-yl] benzenaminecarboxylic acid phenylmethyl ester Following the general procedure of Step 1 of EXAMPLE 17, and making non-critical variations but substituting tetrahydrothiopyran-4-one for N-(carbobenzyloxy)-4-piperidone and recrystallizing the product from ethyl acetate/hexane, the title compound is obtained, mp 152–154° C.

Step 2: 4-(3,6-Dihydro-2H-thiopyran-4-yl) benzenaminecarboxylic acid phenylmethyl ester Following the general procedure of Step 2 of EXAMPLE 17, and making non-critical variations but substituting 4-[4-(hydroxy)tetrahydrothiopyran-4-yl]benzenaminecarboxylic acid phenylmethyl ester (EXAMPLE 54, Step 1) for 4 hydroxy-4-[4-[[(phenylmethoxy)carbonyl]amino]phenyl]-1-piperidinecarboxylic acid phenylmethyl ester and triturating the crude product with diethyl ether or recrystallizing from ethyl acetate/hexane, the title compound is obtained, mp 150–152° C.

Step 3: (R)-(–)-3-[4-(3,6-Dihydro-2H-thiopyran-4-yl) phenyl]-5-hydroxymethyl-2-oxazolidinone Following the general procedure of Step 3 of EXAMPLE 17, and making non-critical variations but substituting 4-(3, 6-dihydro-2H-thiopyran-4-yl)benzenaminecarboxylic acid phenylmethyl ester (EXAMPLE 54, Step 2) for 3,6-dihydro-4-[4-[[(phenylmethoxy)carbonyl]amino]phenyl]-1(2H)-pyridinecarboxylic acid phenylmethyl ester and triturating the crude product with methanol/methylene chloride, the title compound is obtained, mp 182–184° C. (decomp.).

Step 4: (R)-(–)-3-[4-(3,6-Dihydro-2H-thiopyran-4-yl) phenyl]-5-[[(methylsulfonyl)oxy]methyl]-2-oxazolidinone Following the general procedure of Step 4 of EXAMPLE 17, and making non-critical variations but substituting (R)-(–)-3-[4-(3,6-dihydro-2H-thiopyran-4-yl)phenyl]-5-hydroxymethyl-2-oxazolidinone (EXAMPLE 54, Step 3) for (R)-(–)-3,6-dihydro-4-[4-[5-(hydroxymethyl)-2-oxo-3-oxazolidinyl]phenyl]-1(2H)-pyridinecarboxylic acid phenylmethyl ester and triturating the crude product with methylene chloride/diethyl ether (25/75), the title compound is obtained, mp 171–174° C. (decomp.).

Step 5: (S)-(–)-N-[[3-[4-(3,6-Dihydro-2H-thiopyran-4-yl) phenyl]-2-oxo-5-oxazolidinyl]methyl]acetamide Following the general procedure of Step 5 of EXAMPLE 17, and making non-critical variations but substituting (R)-(–)-3-[4-(3,6-dihydro-2H-thiopyran-4-yl)phenyl]-5-[[(methylsulfonyl)oxy]methyl]-2-oxazolidinone (EXAMPLE 54, Step 4) for (R)-(–)-3,6-dihydro-[4-[5-[[(methylsulfonyl)oxy]methyl]-2-oxo-3-oxazolidinyl] phenyl]-1(2H)-pyridinecarboxylic acid phenylmethyl ester and acetonitrile for isopropanol, the title compound is obtained, mp 169° C.–173° C. (decomp.).

EXAMPLE 55

(S)-(–)-N-[[3-[4-(3,6-Dihydro-2H-thiopyran-4-yl) phenyl]-2-oxo-5-oxazolidinyl]methyl]acetamide S, S-dioxide Following the general procedure of EXAMPLE 50, and making non-critical variations but substituting (S)-(–)-N-[[3-[4-(3,6-dihydro-2H-thiopyran-4-yl)phenyl]-2-oxo-5-oxazolidinyl]methyl]acetamide (EXAMPLE 54) for (S)-(–)-N-[[3-[4-(3,6-dihydro-2H-thiopyran-4-yl)-3-fluorophenyl]-2-oxo-5-oxazolidinyl]methyl]acetamide and triturating the product with ethyl acetate/methylene chloride, the title compound is obtained, mp 185–187° C.

EXAMPLE 56

(S)-(–)-N-[[3-[4-[1-(Formyl)-3,6-dihydro-2H-pyridin-4-yl]-3-fluorophenyl]-2-oxo-5-oxazolidinyl] methyl]acetamide Following the general procedure of EXAMPLE 29, and making non-critical variations but substituting (S)-(–)-N-[[2-oxo-3-[4-(3,6-dihydro-2H-pyridin-4-yl)-3-fluorophenyl]-5-oxazolidinyl]methyl]acetamide (EXAMPLE 38) for (S)-(–)-N-[[2-oxo-3-[4-(4-piperidinyl)-3-fluorophenyl]-5-oxazolidinyl]methyl]acetamide, the title compound is obtained, mp 148–151° C.

EXAMPLE 57

(S)-(–)-4-[4-[5-[(Acetylamino)methyl]-2-oxo-3-oxazolidinyl]-2-fluorophenyl]-3,6-dihydro-1(2H)-pyridinecarboxylic acid methyl ester Following the general procedure of EXAMPLE 26, and making non-critical variations but substituting (S)-(–)-N-[[2-oxo-3-[4-(3,6-dihydro-2H-pyridin-4-yl)-3-fluorophenyl]-5-oxazolidinyl]methyl]acetamide (EXAMPLE 38) for (S)-(–)-N-[[2-oxo-3-[4-(4-piperidinyl)-3-fluorophenyl]-5-oxazolidinyl]methyl]acetamide, the title compound is obtained, NMR (CDCl$_3$, 400 MHz) 7.35, 7.18, 7.10, 6.85, 5.89, 4.78, 4.08, 4.02, 3.78, 3.71, 3.64, 2.45, 2.00 δ.

EXAMPLE 58

(S)-(−)-N-[[2-Oxo-3-[4-(3,6-dihydro-2H-pyridin-4-yl)phenyl]-5-oxazolidinyl]methyl]acetamide Step 1: (S)-(−)-4-[4-[5-[(Acetylamino)methyl]-2-oxo-3-oxazolidinyl]phenyl]-3,6-dihydro-1(2H)-pyridinecarboxylic acid 1,1-dimethylethyl ester Following the general procedure of step 1 of EXAMPLE 38, and making non-critical variations but substituting (S)-(−)-N-[[3-[4-(trimethylstannyl)phenyl]-2-oxo-5-oxazolidinyl]methyl]acetamide for (S)-(−)-N-[[3-[4-(trimethylstannyl)-3-fluorophenyl]-2-oxo-5-oxazolidinyl]methyl]acetamide, the title compound is obtained, NMR (CDCl$_3$, 400 MHz) 7.45, 7.35, 6.55, 6.00, 4.77, 4.05, 3.80, 3.63, 2.49, 2.01, 1.48 δ.

Step 2: (S)-(−)-N-[[2-Oxo-3-[4-(3,6-dihydro-2H-pyridin-4-yl)phenyl]-5-oxazolidinyl]methyl]acetamide A solution of (S)-(−)-4-[4-[5-[(acetylamino)methyl]-2-oxo-3-oxazolidinyl]phenyl]-3,6-dihydro-1(2H)-pyridinecarboxylic acid 1,1-dimethylethyl ester (EXAMPLE 58, step 1, 0.92 g) in dry methylene chloride (8.8 mL) at 0° C. under N$_2$ is treated with trifluoroacetic acid (2.2 mL) over one minute, and the resulting mixture is stirred at 0° C. for four hours and added slowly to saturated aqueous potassium carbonate (30 mL) at 0° C. to neutralize excess trifluoroacetic acid. The mixture is then diluted with water (50 mL) and saline (50 mL), extracted with methanol/methylene chloride (3×150 mL, 25/75), and the combined organic phase is dried over anhydrous sodium sulfate and concentrated under reduced pressure to give the title compound, mp 164–166° C. (decomp.).

EXAMPLE 59

(S)-(−)-N-[[2-Oxo-3-[4-[1-[(acetoxy)acetyl]-3,6-dihydro-2H-pyridin-4-yl]phenyl]-5-oxazolidinyl]methyl]acetamide Following the general procedure of EXAMPLE 18, and making non-critical variations but substituting (S)-(−)-N-[[2-oxo-3-[4-(3,6-dihydro-2H-pyridin-4-yl)phenyl]-5-oxazolidinyl]methyl]acetamide (EXAMPLE 58) for (S)-(−)-N-[[2-oxo-3-[(4-piperidinyl)phenyl]-5-oxazolidinyl]methyl]acetamide and acetoxyacetyl chloride for benzyloxyacetyl chloride, the title compound is obtained, HRMS calcd for C$_{21}$H$_{25}$N$_3$O$_6$: 415.1743. Found: 415.1752.

EXAMPLE 60

(S)-(−)-N-[[3-[4-[1-(Hydroxyacetyl)-3,6-dihydro-2H-pyridin-4-yl]-phenyl]-2-oxo-5-oxazolidinyl]methyl]acetamide Following the general procedure of EXAMPLE 40, and making non-critical variations but substituting (S)-(−)-N-[[2-oxo-3-[4-[1-[1(acetoxy)acetyl]-3,6-dihydro-2H-pyridin-4-yl]phenyl]-5-oxazolidinyl]methyl]acetamide (EXAMPLE 59) for (S)-(−)-N-[[2-oxo-3-[3-fluoro-4-[1-[(acetoxy)acetyl]-3,6-dihydro-2H-pyridin-4-yl]phenyl]-5-oxazolidinyl]methyl]acetamide, the title compound is obtained, HRMS (FAB) calcd for C$_{19}$H$_{23}$N$_3$O$_5$+H: 374.1716. Found: 374.1713.

EXAMPLE 61

(S)-(−)-N-[[3-[4-[1-(Formyl)-3,6-dihydro-2H-pyridin-4-yl]phenyl]-2-oxo-5-oxazolidinyl]methyl]acetamide Following the general procedure of EXAMPLE 29, and making non-critical variations but substituting (S)-(−)-N-[[2-oxo-3-[4-(3,6-dihydro-2H-pyridin-4-yl)phenyl]-5-oxazolidinyl]methyl]acetamide (EXAMPLE 58) for (S)-(−)-N-[[2-oxo-3-[4-(4-piperidinyl)-3-fluorophenyl]-5-oxazolidinyl]methyl]acetamide, the title compound is obtained, mp 149–152° C.

EXAMPLE 62

(S)-(−)-4-[4-[5-[(Acetylamino)methyl]-2-oxo-3-oxazolidinyl]phenyl]-3,6-dihydro-1(2H)-pyridinecarboxylic acid methyl ester Following the general procedure of EXAMPLE 26, and making non-critical variations but substituting (S)-(−)-N-[[2-oxo-3-[4-(3,6-dihydro-2H-pyridin-4-yl)phenyl]-5-oxazolidinyl]methyl]acetamide (EXAMPLE 58) for (S)-(−)-N-[[2-oxo-3-[4-(4-piperidinyl)-3-fluorophenyl]-5-oxazolidinyl]methyl]acetamide, the title compound is obtained, mp 142–145° C.

EXAMPLE 63

(S)-(−)-N-[[3-[4-(3,6-Dihydro-2H-thiopyran-4-yl)-3-fluorophenyl]-2-oxo-5-oxazolidinyl]methyl] acetamide S-oxide A solution of sodium periodate (192 mg) in water at 0° C. is treated with a slurry of (S)-(−)-N-[[3-[4-(3,6-dihydro-2H-thiopyran-4-yl)-3-fluorophenyl]-2-oxo-5-oxazolidinyl]methyl]acetamide (EXAMPLE 49, 300 mg) in methanol (10 mL), and the resulting mixture is allowed to slowly warm to ambient temperature over approximately one hour and is stirred overnight. The mixture is then concentrated to remove methanol, diluted with water (20 mL) and extracted with methanol/chloroform (3×30 mL, 5/95). The combined organic phase is washed with saline (20 mL), dried over anhydrous sodium sulfate and concentrated under reduced pressure to give the crude product which is then chromatographed on silica gel (30 g, 70–230 mesh), eluting with methanol/methylene chloride (5/95). Those fractions an R$_f$=0.39 by TLC (methanol/chloroform, 10/90) were pooled and concentrated and the residue was recrystallized from methylene chloride/diethyl ether to give the title compound, mp 150–151° C.

EXAMPLE 64

(S)-(−)-N-[[3-[4-(3,6-Dihydro-2H-thiopyran-4-yl)phenyl]-2-oxo-5-oxazolidinyl]methyl]acetamide S-oxide Following the general procedure of EXAMPLE 63, and making non-critical variations but substituting (S)-(−)-N-[[3-[4-(3,6-dihydro-2H-thiopyran-4-yl)phenyl]-2-oxo-5-oxazolidinyl]methyl]acetamide (EXAMPLE 54) for (S)-(−)-N-[[3-[4-(3,6-dihydro-2H-thiopyran-4-yl)-3-fluorophenyl]-2-oxo-5-oxazolidinyl]methyl]acetamide, the title compound is obtained, mp 158–162° C. (decomp.).

EXAMPLE 65

(S)-(−)-N-[[3-[4-(Tetrahydro-2H-thiopyran-4-yl)phenyl]-2-oxo-5-oxazolidinyl]methyl]acetamide S,S-dioxide A mixture of (S)-(−)-N-[[3-[4-(3,6-dihydro-2H-thiopyran-4-yl)phenyl]-2-oxo-5-oxazolidinyl]methyl] acetamide S,S-dioxide (EXAMPLE 55, 75 mg) and 10% palladium-on-carbon (44 mg) in tetrahydrofuran (20 mL) is stirred under a hydrogen atmosphere (balloon) for one hour, the catalyst is removed by filtration through Celite, the filtrate is concentrated under reduced pressure and the residue is recrystallized from methylene chloride/diethyl ether to give the title compound, mp 190–192° C. (decomp.).

EXAMPLE 66

3-(4-amino-2-fluorophenyl)pyrrolidine

Step 1: 2-(2-fluoro-4-nitrophenyl)-dimethylmalonate

A flame-dried 500 mL round bottom flask equipped with spinbar and addition funnel was charged with sodium hydride (4.0 g, 0.10 mol). This oil dispersion was washed three times with pentane (30 mL), dried under house vacuum, diluted with 50 mL of freshly distilled tetrahydrofuran, and cooled to 0° C. The grey suspension was drop-wise treated with a 100 mL THF solution of dimethylmalonate (5.7 mL, 50 mmol) with copious gas evolution. The resulting thick suspension was treated with a 100 mL THF solution of 3,4-difluoronitrobenzene, quickly turning golden in color and was warmed to 50° C. for 16 hours. At this time, the deep red wine homogenous solution was cooled to RT, quenched with 300 mL 1 M hydrochloric acid, and volatiles removed in vacuo. The resulting aqueous acidic residue was extracted three time with ethyl acetate (200 mL) with the combined organics washed once with brine (200 mL), dried over Mg SO$_4$, filtered and concentrated to give 13.58 g of a brown solid. This material was triturated with a mixture of ethyl acetate/hexane/dichloromethane to afford 7.60 g of the title compound as a light yellow solid. The filtrate was concentrated and purified by Prep 500 HPLC on a single silica gel cartridge eluting with 25% ethyl acetate/hexane to afford and additional 3.95 g of the title compound. Total yield 10.60 g (78%), mp 108–109. mp 108–109° C.; R$_f$ 0.38 (25% ethyl acetate/hexane); IR (mull) 1744, 1736, 1532, 1438, 1357, 1345, 1273, 1243, 1232, 812 cm$^{-1}$; $^1$H NMR (300 MHz, CDCl$_3$) δ8.09 (dt, 1H, J=2.2 & J=7.8 Hz, aromatic), 7.99 (ddd, 1H, J=2.3 & 9.4 Hz, aromatic), 7.74 (dd, 1H, J=7.1 & J=8.6 Hz, aromatic), 5.08 (s, 1H, methine), 3.81 (s, 6H, methyls); Anal. Calcd for C$_{11}$H$_{10}$N$_1$O$_6$F$_1$: C, 48.74; H, 3.72; N, 5.17. Found: C, 48.74; H, 3.84; N, 5.14.

Step 2: 2-(2-fluoro-4-nitrophenyl)-2-(cyanomethyl)-dimethylmalonate

An oven-dried 100 mL round bottom flask equipped with spinbar and reflux condenser was charged with 2-(2-fluoro-4-nitrophenyl)-dimethylmalonate (EXAMPLE 66, Step 1, 3.25 g, 12.0 mmol) and 60 mL acetone. This yellow homogenous solution was treated with a single portion of powdered potassium carbonate (4.98 g, 36 mmol) instantly turning red in color. This suspension was added to by bromoacetonitrile (1.3 mL, 18 mmol) and heated to reflux for 16 hours. At this time, the now brown suspension was cooled to RT, diluted with 100 mL 1 M hydrochloric acid, and extracted twice with ethyl acetate (150 mL). The combined organics were washed once with brine (100 mL), dried over MgSO$_4$, filtered, and concentrated to give 4.10 g of a crude brown foam. This material was purified by Prep 500 HPLC on a single silica gel cartridge eluting with 30% ethyl acetate/hexane to afford 3.60 g of an off-white solid. This material was recrystallized from ethyl acetate/hexanes to give 3.14 g (84%) of the title compound as white needles. mp 137–138° C.; R$_f$ 0.26 (30% ethyl acetate/hexanes); IR (mull) 1749, 1730, 1527, 1355, 1290, 1276, 1262, 1234, 812, 739 cm$^{-1}$; $^1$H NMR (300 MHz, CDCl$_3$) 8.12 (ddd, 1H, J$_{HF}$=0.8, J=2.2, J=8.6 Hz, aromatic), 8.01 (dd, 1H, J=2.3 & 10.8 Hz, aromatic), 7.48 (dd, 1H, J=7.5 & J=8.7 Hz, aromatic), 3.92 (s, 6H, methyls), 3.34 (s, 2H, methine); $^{13}$C NMR (75 MHz,CDCl$_3$) 166.5, 159.5 J$_{CF}$=253 Hz), 148.7, 130.2 (J$_{CF}$=3 Hz), 129.9 (J$_{CF}$=13 Hz), 119.4 (J$_{CF}$=3 Hz), 11.9 J$_{CF}$=28 Hz), 58.0, 54.1, 24.2; Anal. Calcd for C$_{13}$H$_{11}$N$_2$O$_6$F$_1$: C, 50.33; H, 3.57; N, 9.03. Found: C, 50.23; H, 3.73; N, 9.06.

Step 3: 2-(4-amino-2-fluorophenyl)-2-carbomethoxypyrrolidinone.

A 500 mL Parr flask was charged with a solution of 2-(2-fluoro-4-nitrophenyl)-2-(cyanomethyl)-dimethylmalonate (EXAMPLE 66, Step 2, 1.236 g, 4.0 mmol) in 100 mL methanol and 1.17 g 10% palladium on carbon. The black suspension was placed under 40 psi hydrogen with shaking for 64 hours. The Parr was removed from the hydrogentaor, the reaction mixture was filtered through a pad of CELITE and concentrated to afford 1.02 g of a white foam. This material was purified by LC on 70 g (230–400) silica gel eluting with ethyl acetate to afford 824 mg (82%) of the compound as a white amorphous solid. R$_f$ 0.20 (75% ethyl acetate/hexanes); IR (mull) 3359, 3233, 1738, 1695, 1694, 1634, 1515, 1254, 1276, 1128, cm$^{-1}$; $^1$H NMR (300 MHz, CDCl$_3$) δ7.15 (t, 1H, J=9.0 Hz, aromatic), 6.58 (bs, 1H, O=C—NH), 6.41 (m, 2H, aromatic), 3.80 (bs, 2H, NH$_2$), 3.77 (s, 3H, CH$_3$), 3.49 (m, 1H, N—CH$_{2a}$), 3.25 (m, 2H, C—CH$_2$s), 2.28 (m, 1H, N—CH$_{2b}$); $^{13}$C NMR (75 MHz, CDCl$_3$) 173.6, 170.9, 161.4 (J$_{CF}$=245 Hz), 147.7 (J$_{CF}$11 Hz), 128.9 (J$_{CF}$=5 Hz), 115.7 (J$_{CF}$=14 Hz), 110.2, 102.5, (J$_{CF}$=25 Hz), 56.9, 53.2, 39.4, 34.3; K.F. Water= 0.87%; Anal. Calcd for C$_{12}$H$_{13}$N$_2$O$_3$F$_1$ with 0.87% water: C, 56.64; H, 5.25; N, 11.01. Found: C, 56.78; H, 5.34; N, 11.01. HRMS Calcd for C$_{12}$H$_{13}$N$_2$O$_3$F$_1$: 252.0910. Found: 252.0902.

Step 4: 2-(4-amino-2-fluorophenyl)-2-carbomethoxypyrrolidinone

A 100 mL recovery flask containing 2-(4 amino-2-fluorophenyl)-2-carbomethoxypyrrolidinone (EXAMPLE 66, Step 3, 930 mg, 3.7 mmol) was charged with 26 mL DMSO and sodium cyanide (542 mg, 11.1 mmol). This rose colored suspension was heated to 150° C. for 30 minutes becoming reddish/brown in color with some gas evolution. At this time, the reaction was cooled to RT, DMSO removed under reduced pressure (approx. 60° C., 0.1 mm Hg), with the resulting residue diluted with 30 mL brine and extracted three times with dichloromethane (30 mL). The combined organics were washed once with brine (15 mL), dried over MgSO$_4$, filtered, and concentrated to give 521 m g of a red/brown oil. TLC indicated remaining product in the brine layers and they were combined and extracted three times with ethyl acetate (30 mL). These combined organics were washed once with brine (15 mL), dried over MgSO$_4$, filtered, and concentrated to give an additional 230 m g of a red/brown oil. These crude extracts were purified by LC on 49 g (230–400) silica gel eluting with 5% methanol/ethyl acetate to afford 628 mg (88%) of the title compound as a light yellow solid. mp 157–160° C.; R$_f$ 0.24 (ethyl acetate); IR (mull) 3465, 3363, 1680, 1630, 1614, 1515, 1447, 1285, 830, 828 cm$^{-1}$; $^1$H NMR (300 MHz, CDCl$_3$) δ7.73 (bs, 1H, O=C—NH), 6.85 (t, 1H, J=8.4 Hz, aromatic), 6.31 (m, 2H, aromatic), 5.28 tbs, 2H, NH$_2$), 3.48 (t, 1H, J=9.4 Hz, Ph-CH), 3.24 (m, 2H, C—CH$_2$s), 2.35 (m, 1H, N—CH$_{2a}$), 1.95 (m, 1H, N—CH$_{2b}$); $^{13}$C NMR (75 MHz, CDCl$_3$) 178.8, 161.9 (J$_{CF}$=244 HZ), 147.5 (J$_{CF}$=11 Hz), 130.4 (J$_{CF}$=6 Hz), 115.7 (J$_{CF}$=15 Hz), 111.1 (J$_{CF}$=2 Hz), 102.3 (J$_{CF}$=25 Hz), 41.5, 40.5, 30.1; HRMS Calcd for C$_{10}$H$_{11}$N$_2$O$_1$F$_1$+H: 195.0134. Found: 195.0937.

Step 5: 3-(4-amino-2-fluorophenyl)pyrrolidine 100 mL round bottom flask equipped with spinbar and reflux condenser was charged with 2-(4-amino-2-fluorophenyl)-2-carbomethoxypyrrolidinone (EXAMPLE 66, Step 4, 430 mg, 2.2 mmol) and 22 mL freshly distilled THF followed by cooling to 0° C. This light yellow homogeneous solution was treated with a 1 M solution of lithium aluminumhydride (11 mL, 11 mmol) instantly becoming an opaque light rose color with copious gas evolution. The reaction was warmed to RT then heated to reflux with the formation of a gelatinous precipitate. After 20 hours, the now green/yellow thick suspension was successively quenched by the addition of 0.42 mL water, 0.38 mL 5 N sodium hydroxide, and 1.5 mL water. The resulting thick gelatinous suspension was diluted with ethyl acetate, filtered through a pad of Celite, and concentrated to give 392 mg of a yellow oil. This material was purified by LC on 25 g (230–400) silica gel eluting with 2:17:81 sat. $NH_4OH$:methanol:dichloromethane to afford 295 mg (74%) of the title compound as a light yellow oil. This material was dissolved in a mixture of methanol/ethylacetate and treated with gaseous HCl with no observable change. This solution was concentrated to afford a peach colored foam that failed to recrystallize from many different solvent combinations. $R_f$ 0.20 (2:17:81 sat $NH_4OH$:methanol:dichloromethane); IR (mull) 3139, 3042, 3016, 2766, 2562, 1514, 1485, 1444, 1266, 1108 cm$^{-1}$; $^1$H NMR (300 MHz, CDCl$_3$) δ6.99 (t, 1H, J=8.2 Hz, aromatic), 6.39 (m, 2H, aromatic), 3.70 (bs, 2H, Ph-NHs), 3.27 (m, 2H, methine, N—CH$_{2a}$—CH), 3.11 (m, 2H, N—CH$_2$s—CH$_2$), 2.80 (dd, 1H, J=6.2 & 8.9 Hz, N—CH$_{2b}$—CH), 2.30 (bs, 1H, NH), 2.14 (m, 1H, N—CH$_2$—C$_{2a}$), 1.81 (m, 1H, N—CH$_2$—CH$_{2b}$); $^{13}$C NMR (75 MHz, CDCl$_3$) 161.4 ($J_{CF}$=243 Hz), 146.0 ($J_{CF}$=11 Hz), 128.4 ($J_{CF}$=7 HZ), 119.9 ($J_{CF}$=152 HZ), 110.5 ($J_{CF}$=2 HZ), 102.1 ($J_{CF}$=26 HZ), 53.6, 47.0, 38.1, 32.9; Anal. Calcd for $C_{10}H_{13}N_2F_1$: C, 47.45; H, 5.93; N, 11.07. Found: C, 47.10; H, 6.10; N, 10.74. HRMS Calcd for $C_{10}H_{13}N_2F_1$: 180.1063. Found: 180.1060.

EXAMPLE 67

(S)-(–)-N-[[3-[3-Fluoro-4-(dihydrothien-3-yl)-phenyl]-2-oxo-5-oxazolidinyl]methyl]acetamide Step 1: 3-Fluoro-4-[3-(hydroxy)tetrahydrothiophen-3-yl]benzenaminecarboxylic acid phenylmethyl ester A solution of 1-(3-fluorophenyl)-2,2,5,5-tetramethyl-1-aza-2,5-disilacyclopentane (EXAMPLE 20, Step 1, 1.00 g) in dry tetrahydrofuran (16 mL) at –78° C. under N$_2$ is treated with sec-butyllithium (1.3 M in cyclohexane, 3.30 mL) dropwise over 2 mins, and the resulting mixture is stirred at –78° C. for 2 hrs. The mixture is then treated with a solution of tetrahydrothiophen-3-one (423 mg) in dry tetrahydrofuran (4.1 mL) dropwise over 2 mins and is stirred at –78° C., allowing the cooling bath to expire over 4 hrs. The mixture is then quenched with saturated aqueous ammonium chloride (25 mL), diluted with water (25 mL), the layers are separated, and the combined organic phase is washed with saline (20 mL), dried over anhydrous sodium sulfate and concentrated under reduced pressure. The residue is dissolved in methanol (16 mL) and treated with anhydrous potassium carbonate (1.09 g), and the mixture is stirred at ambient temperature for 30 mins, concentrated under reduced pressure, diluted with water (20 mL) and extracted with diethyl ether (2×20 mL). The combined organic phase is washed with saline (10 mL), dried over anhydrous magnesium sulfate and concentrated under reduced pressure to give the crude 3-fluoro-4-[3-(hydroxy)tetrahydrothiophen-3-yl]benzenamine intermediate ($R_f$=0.37 by TLC, ethyl acetate/hexane (50/50)). A solution of this intermediate in tetrahydrofuran (16 mL) and water (8 mL) is then treated with sodium bicarbonate (662 mg) and benzyl chloroformate (0.56 mL), and the resulting mixture is stirred at ambient temperature for 4 hrs, diluted with water (8 mL), the layers are separated, and the organic phase is washed with saline (10 mL), dried over anhydrous magnesium sulfate and concentrated under reduced pressure. The residue is chromatographed on silica gel (230–400 mesh, 150 g), eluting with ethyl acetate/hexane (25/75), and those fractions with an $R_f$=0.19 by TLC (ethyl acetate/hexane, 25/75) are pooled and concentrated to give the title compound, mp 134–135° C.

Step 2: 3-Fluoro-4-(dihydrothien-3-yl) benzenaminecarboxylic acid phenylmethyl ester Following the general procedure of EXAMPLE 17, Step 2, and making non-critical variations but substituting 3-fluoro-4[-3-(hydroxy)tetrahydrothiophen-3-yl] benzenaminecarboxylic acid phenylmethyl ester (EXAMPLE 67, Step 1) for 4-hydroxy-4-[4-[[(phenylmethoxy)carbonyl]amino]phenyl]-1-piperidinecarboxylic acid phenylmethyl ester, the title compound is obtained as a mixture of the 2,5- and 4,5-dihydro regioisomers. NMR (CDCl$_3$, 400 MHz) δ7.40, 7.21, 7.14, 7.02, 6.73, 6.69, 6.31, 5.21, 4.10, 3.94, 3.33 and 3.15.

Step 3: (R)-3-[3-Fluoro-4-(dihydrothien-3-yl)phenyl]-5-hydroxymethyl-2-oxazolidinone Following the general procedure of EXAMPLE 17, Step 3, and making non-critical variations but substituting 3-fluoro-4-(dihydrothien-3-yl)benzenaminecarboxylic acid phenylmethyl ester (EXAMPLE 67, Step 2, mixture of the 2,5- and 4,5-dihydro regioisomers) for 3,6-dihydro-4-[4-[[(phenylmethoxy)carbonyl]amino]phenyl]-1(2H)-pyridinecarboxylic acid phenylmethyl ester, the title compound is obtained as a mixture of the 2,5- and 4,5-dihydro regioisomers. HRMS calculated for $C_{14}H_{14}N_1F_1O_3S_1$: 295.0678. Found: 295.0676.

Step 4: (R)-3-[3-Fluoro-4-(dihydrothien-3-yl)phenyl]-5-[[(methylsulfonyl)oxy]methyl]-2-oxazolidinone Following the general procedure of EXAMPLE 17, Step 4, and making non-critical variations but substituting (R)-3-[3-fluoro-4-(dihydrothien-3-yl)phenyl]-5-hydroxymethyl-2-oxazolidinone (EXAMPLE 67, Step 3, mixture of the 2,5- and 4,5-dihydro regioisomers) for (R)-(–)-3,6-dihydro-4-[4-[5-(hydroxymethyl)-2-oxo-3-oxazolidinyl]phenyl]-1(2H)-pyridinecarboxylic acid phenylmethyl ester, the title compound is obtained as a mixture of the 2,5- and 4,5-dihydro regioisomers. HRMS calculated for $C_{15}H_{16}N_1F_1O_5S_2$: 373.0454. Found: 373.0440.

Step 5: (S)-N-[[3-[3-Fluoro-4-(dihydrothien-3-yl)phenyl]-2-oxo-5-oxazolidinyl]methyl]acetamide Following the general procedure of EXAMPLE 17, Step 5, and making non-critical variations but substituting (R)-3-[3-fluoro-4-(dihydrothien-3-yl)phenyl]-5-[[(methylsulfonyl)oxy]methyl]-2-oxazolidinone (EXAMPLE 67, Step 4, mixture of the 2,5- and 4,5-dihydro regioisomers) for (R)-(–)-3,6-dihydro-4-[4-[5-[[(methylsulfonyl)oxy]methyl]-2-oxo-3-oxazolidinyl]phenyl]-1(2H)-pyridinecarboxylic acid phenylmethyl ester, the title compound is obtained as a mixture of the 2,5- and 4,5-dihydro regioisomers. Anal. calculated for $C_{16}H_{17}F_1N_2O_3S_1$: C, 57.13; H, 5.09; N, 8.33. Found: C, 56.89; H, 5.18; N, 8.24.

EXAMPLE 68

(5S)-N-[[3-[3-Fluoro-4-(2,5-dihydro-1-oxido-3-thienyl)-phenyl]-2-oxo-5-oxazolidinyl]methyl] acetamide (68a) and (5S)-N-[[3-[3-Fluoro-4-(4,5-dihydro-1-oxido-3-thienyl)phenyl]-2-oxo-5-oxazolidinyl]methyl]acetamide (68b)

Following the general procedure of EXAMPLE 63, and making non-critical variations but substituting (S)-N-[[3-[3- fluoro-4-(dihydrothien-3-yl)phenyl]-2-oxo-5-oxazolidinyl]
methyl]acetamide (EXAMPLE 67, Step 5, mixture of the
2,5- and 4,5-dihydro regioisomers) for (S)-(–)-N-[[3-[4-(3,
6-dihydro-2H-thiopyran-4-yl)-3-fluorophenyl]-2-oxo-5-
oxazolidinyl]methyl]acetamide and separating the regioisomers by chromatography on silica gel (230–400 mesh, methanol/methylene chloride (4/96) eluent), the title compounds are obtained. mp (68a) 208–210° C. (decomp.); NMR (68b) (CDCl$_3$, 400 MHz) 7.55, 7.46, 7.27, 7.13, 6.11, 4.82, 4.07, 3.82–3.62, 3.43, 3.23, 3.10 and 2.03 δ.

EXAMPLE 69

(S)-N-[[3-[3-Fluoro-4-(2,5-dihydro-1,1-dioxido-3-thienyl)-phenyl]-2-oxo-5-oxazolidinyl]methyl]
acetamide (69a) and (S)-N-[[3-[3-Fluoro-4-(4,5-dihydro-1,1-dioxido-3-thienyl)-phenyl]-2-oxo-5-oxazolidinyl]methyl]acetamide (69b)

Following the general procedure of EXAMPLE 50, and making non-critical variations but substituting (S)-N-[[3-[3-fluoro-4-(dihydrothien-3-yl)phenyl]-2-oxo-5-oxazolidinyl] methyl]acetamide (EXAMPLE 67, Step 5, mixture of the 2,5- and 4,5-dihydro regioisomers) for (S)-(–)-N-[[3-[4-(3, 6-dihydro-2H-thiopyran-4-yl)-3-fluorophenyl]-2-oxo-5-oxazolidinyl]methyl]acetamide and separating the regioisomers by HPLC (Chiralpak AD, 10% isopropanol/methanol (0.05% diethylamine), 0.5 mn/min), the title compounds are obtained. mp (69a) 183–185° C. (decomp.); (69b) 238–239° C. (decomp.).

EXAMPLE 70

(S)-N-[[2-Oxo-3-[3-fluoro-4-[1-[(acetoxy)acetyl]-5,
6-dihydro-2H-pyridin-3-yl]-phenyl]-5-oxazolidinyl]
methyl]acetamide Step 1: 5,6-Dihydro-3-[[(trifluoromethyl)sulfonyl]oxy]-1
(2H)-pyridinecarboxylic acid 1,1-dimethylethyl ester Following the general procedure of EXAMPLE 20, Step 2, and making non-critical variations but substituting 1-(1, 1-dimethylethoxycarbonyl)-3-piperidone for 1-(1,1-dimethylethoxycarbonyl)-4-piperidone and isolating the desired regioisomer by chromatography on silica gel (70–230 mesh, ethyl acetate/hexane (10/90) eluent), the title compound is obtained, NMR (CDCl$_3$, 400 MHz) 5.92, 4.04, 3.49, 2.30 and 1.47 δ.

Step 2: (S)-3-[4-[5-[(Acetylamino)methyl]-2-oxo-3-oxazolidinyl]-2-fluorophenyl]-5,6-dihydro-1(2H)-pyridine-1-carboxylic acid 1,1-dimethylethyl ester Following the general procedure of EXAMPLE 38, Step 1, and making non-critical variations but substituting 5,6-dihydro-3-[[(trifluoromethyl)sulfonyl]oxy]-1(2H)-pyridinecarboxylic acid 1,1-dimethylethyl ester (EXAMPLE 70, Step 1) for 3,6-dihydro-4-[[(trifluoromethyl)sulfonyl]oxy]-1(2H)-pyridinecarboxylic acid 1,1-dimethylethyl ester, the title compound is obtained, NMR (CDCl$_3$, 400 MHz) 7.41, 7.25, 7.17, 6.06, 4.79, 4.19, 4.06, 3.78, 3.75–3.59, 3.57, 2.32, 2.03 and 1.49 δ.

Step 3: (S)-N-[[2-Oxo-3-[3-fluoro-4-[1-[(acetoxy)acetyl]-5, 6-dihydro-2H-pyridin-3-yl]phenyl]-5-oxazolidinyl]methyl] acetamide A solution of (S)-3-[4-[5-[(acetylamino)methyl]-2-oxo-3-oxazolidinyl]-2-fluorophenyl]-5,6-dihydro-1(2H)-pyridinecarboxylic acid 1,1-dimethylethyl ester (EXAMPLE 70, Step 2, 158 mg) in dry acetonitrile under N$_2$ is treated with iodotrimethylsilane (62 μL) dropwise, and the resulting solution is stirred at ambient temperature for 50 mins, during which additional iodotrimethylsilane (25 μL) is added. The reaction is then treated with methanol (59 μL), stirred for 5 mins and concentrated under reduced pressure to give the deprotected intermediate. A mixture of this intermediate and triethylamine (0.122 mL) in dry methylene chloride (3.6 mL) at 0° C. under N$_2$ is treated with acetoxyacetyl chloride (47 μL), and the resulting mixture is stirred at 0° C. for 2 hrs and at ambient temperature for 2 hrs and then diluted with methylene chloride (20 mL), washed with water (10 mL), saturated aqueous sodium bicarbonate (10 mL) and saline (10 mL), dried over anhydrous sodium sulfate and concentrated under reduced pressure. The residue is chromatographed on silica gel (70–230 mesh, 15 g), eluting with methanol/methylene chloride (5/95), and those fractions with an R$_f$=0.5 by TLC (methanol/chloroform, 10/90) are pooled and concentrated to give the title compound, HRMS calculated for C$_{21}$H$_{24}$N$_3$F$_1$O$_6$+H$_1$: 434.1727. Found: 434.1741.

EXAMPLE 71

(S)-N-[[3-[4-[1-(Hydroxyacetyl)-5,6-dihydro-2H-pyridin-3-yl]-3-fluorophenyl]-2-oxo-5-oxazolidinyl]
methyl]acetamide A mixture of (S)-N-[[2-oxo-3-[3-fluoro-4-[1-[(acetoxy) acetyl]-5,6-dihydro-2H-pyridin-3-yl]phenyl]-5-oxazolidinyl]methyl]acetamide (EXAMPLE 70, Step 3, 105 mg) and anhydrous potassium carbonate (67 mg) in methanol (4.8 mL) is stirred under N$_2$ at ambient temperature for 2 hrs and is then neutralized with hydrochloric acid (1 M), diluted with water (10 mL) and methylene chloride (40 mL), and the layers are separated. The organic phase is washed with saline (10 mL), dried over anhydrous sodium sulfate and concentrated under reduced pressure to give the crude product, which is then chromatographed on silica gel (70–230 mesh, 15 g), eluting with methanol/methylene chloride (5/95). Pooling and concentration of those fractions with an R$_f$=0.30 by TLC (methanol/chloroform, 10/90) gives the title compound, mp 188–190° C.

EXAMPLE 72

(S)-N-[[2-Oxo-3-[3-fluoro-4-[1-[(acetoxy)acetyl]-3,
4-dihydro-2H-pyridin-5-yl]phenyl]-5-oxazolidinyl]
methyl]acetamide Step 1: 3-Hydroxy-3-[4-[[(phenylmethoxy)carbonyl] amino]-2-fluorophenyl]-1-piperidinecarboxylic acid phenylmethyl ester Following the general procedure of EXAMPLE 67, Step 1, and making non-critical variations but substituting N-(carbobenzyloxy)-3-piperidone for tetrahydrothiophen-3-one, the title compound is obtained, mp 137–139° C.

Step 2: 3,4-Dihydro-5-[[4-[[(phenylmethoxy)carbonyl] amino]-2-fluorophenyl]-1(2H)-pyridinecarboxylic acid phenylmethyl ester Following the general procedure of EXAMPLE 17, Step 2, and making non-critical variations but substituting 3-hydroxy-3-[4-[[(phenylmethoxy)carbonyl]amino]-2-fluorophenyl]-1-piperidinecarboxylic acid phenylmethyl ester (EXAMPLE 72, Step 1) for 4-hydroxy-4-[4-[[(phenylmethoxy)carbonyl]amino]phenyl]-1-piperidinecarboxylic acid phenylmethyl ester, the title compound is obtained, mp 138–139° C.

Step 3: (R)-3,4-Dihydro-5-[4-[5-(hydroxymethyl)-2-oxo-3-oxazolidinyl]-2-fluorophenyl]-1(2H)-pyridinecarboxylic acid phenylmethyl ester Following the general procedure of EXAMPLE 17, Step 3, and making non-critical variations but substituting 3,4-

Dihydro-5-[4-[[(phenylmethoxy)carbonyl]amino]-2-fluorophenyl]-1(2H)-pyridinecarboxylic acid phenylmethyl ester (EXAMPLE 72, Step 2) for 3,6-dihydro-4-[4-[[(phenylmethoxy)carbonyl]amino]phenyl]-1(2H)-pyridinecarboxylic acid phenylmethyl ester, the title compound is obtained, HRMS calculated for $C_{23}H_{23}N_2F_1O_5$: 426.1591. Found: 426.1594.

Step 4: (R)-3,4-Dihydro-5-[4-[5-[5-[[(methylsulfonyl)oxy]methyl]-2-oxo-3-oxazolidinyl]-2-fluorophenyl]-1(2H)-pyridinecarboxylic acid phenylmethyl ester Following the general procedure of EXAMPLE 17, Step 4, and making non-critical variations but substituting (R)-3,4-Dihydro-5-[4-[5-(hydroxymethyl)-2-oxo-3-oxazolidinyl]-2-fluorophenyl]-1(2H)-pyridinecarboxylic acid phenylmethyl ester (EXAMPLE 72, Step 3) for (R)-(−)-3,6-dihydro-4-[4-[5-(hydroxymethyl)-2-oxo-3-oxazolidinyl]phenyl]-1(2H)-pyridinecarboxylic acid phenylmethyl ester, the title compound is obtained, NMR (CDCl$_3$, 400 MHz) 7.39, 7.27, 7.18, 5.23, 4.93, 4.47, 4.15, 3.95, 3.71, 3.11, 2.44 and 1.97 δ.

Step 5: (S)-(−)-5-[4-[5-[(Acetylamino)methyl]-2-oxo-3-oxazolidinyl]-2-fluorophenyl]-3,4-dihydro-1(2H)-pyridinecarboxylic acid phenylmethyl ester Following the general procedure of EXAMPLE 17, Step 5, and making non-critical variations but substituting (R)-3,4-Dihydro-5-[4-[5-[[(methylsulfonyl)oxy]methyl]-2-oxo-3-oxazolidinyl]-2-fluorophenyl]-1(2H)-pyridinecarboxylic acid phenylmethyl ester (EXAMPLE 72, Step 4) for (R)-(−)-3,6-dihydro-4-[4-[5-[[(methylsulfonyl)oxy]methyl]-2-oxo-3-oxazolidinyl]phenyl]-1(2H)-pyridinecarboxylic acid phenylmethyl ester, the title compound is obtained, HRMS calculated for $C_{25}H_{26}F_1N_3O_5$: 467.1856. Found: 467.1862.

Step 6: (S)-N-[[2-Oxo-3-[3-fluoro-4-[1-[(acetoxy)acetyl]-3,4dihydro-2H-pyridin-5-yl]phenyl]-5-oxazolidinyl]methyl]acetamide Following the general procedure of EXAMPLE 70, Step 3, and making non-critical variations but substituting (S)-(−)-5-[4-[5-[(Acetylamino)methyl]-2-oxo-3-oxazolidinyl]-2-fluorophenyl]-3,4-dihydro-1(2H)-pyridinecarboxylic acid phenylmethyl ester (EXAMPLE 72, Step 5) for (S)-(−)-5-[4-[5-[(Acetylamino)methyl]-2-oxo-3-oxazolidinyl]-2-fluorophenyl]-3,6-dihydro-1(2H)-pyridinecarboxylic acid 1,1-dimethylethyl ester, the title compound is obtained, mp 146–148° C.

EXAMPLE 73

(S)-(−)-N-[[3-[4-[1-(Hydroxyacetyl)-3,4dihydro-2H-pyridin-5-yl]-3-fluorophenyl]-2-oxo-5-oxazolidinyl]methyl]acetamide A mixture of (S)-N-[[2-Oxo-3-[3-fluoro-4-[1-[(acetoxy)acetyl]-3,4-dihydro-2H-pyridin-5-yl]phenyl]-5-oxazolidinyl]methyl]acetamide (EXAMPLE 72, Step 6, 238 mg) and anhydrous potassium carbonate (151 mg) in methanol (27 mL) is stirred under N$_2$ at ambient temperature for 2 hrs and is then neutralized with hydrochloric acid (1 M) and concentrated under reduced pressure. The residue is then diluted with methylene chloride (100 mL) and saline (50 mL) and the resultant insoluble product is removed by filtration and dried under reduced pressure. The layers in the filtrate are separated and the organic phase is dried over anhydrous sodium sulfate and concentrated under reduced pressure to give additional quantities of the title compound, mp 171–173° C.

EXAMPLE 74

(S)-(−)-N-[[3-[4-[1-Formyl-4-fluoro-4-piperidinyl]-3-fluorophenyl]-2-oxo-5-oxazolidinyl]methyl]acetamide Step 1: 4-Hydroxy-4-[2-fluoro-4-[[(phenylmethoxy)carbonyl]amino]phenyl]-1-piperidinecarboxylic acid phenylmethyl ester A solution of 1-(3-fluorophenyl)-2,2,5,5-tetramethyl-1-aza-2,5-disilacyclopentane (EXAMPLE 20, Step 1, 1.00 g) in dry tetrahydrofuran (9.8 mL) at −78° C. under N$_2$ is treated with sec-butyllithium (1.3 M in cyclohexane, 3.64 mL) dropwise over 3 mins, and the resulting mixture is stirred at −78° C. for 2 hrs. The mixture is then treated with a solution of N-(carbobenzyloxy)-4-piperidone (919 mg) in dry tetrahydrofuran (3.9 mL) dropwise over 2 mins and is stirred at −78° C. for 2 hrs. The mixture is then warmed to −20° C. over 1 hr and quenched with saturated aqueous ammonium chloride (5 mL), diluted with water (20 mL), the layers are separated, the aqueous phase is extracted with diethyl ether (20 mL), and the combined organic phase is washed with saline (10 mL), dried over anhydrous sodium sulfate and concentrated under reduced pressure. The residue is dissolved in methanol (15 mL) and treated with anhydrous potassium carbonate (544 mg, 3.94 mmol), and the mixture is stirred at ambient temperature for 30 mins, concentrated under reduced pressure, diluted with diethyl ether (30 mL), washed with water (20 mL) and saline (10 mL), dried over anhydrous magnesium sulfate and concentrated under reduced pressure to give the crude 4-(hydroxy) piperidinyl benzenamine intermediate ($R_f$=0.25 by TLC, ethyl acetate/hexane (50/50)). A mixture of this intermediate and N,N-dimethylaniline (1.00 mL) in tetrahydrofuran (20 mL) is cooled to −20° C. and treated with benzyl chloroformate (0.59 mL), and the resulting mixture is stirred at −20° C. for 1 hr. The mixture is then diluted with saturated aqueous potassium carbonate (5 mL), water (25 mL) and diethyl ether (25 mL), the layers are separated, and the organic phase is washed with water (20 mL) and saline (20 mL), dried over anhydrous sodium sulfate and concentrated under reduced pressure. The residue is chromatographed on silica gel (230–400 mesh, 150 g), eluting with a gradient of ethyl acetate/hexane (25/75–50/50), and those fractions with an $R_f$=0.47 by TLC (ethyl acetate/hexane, 50/50) are pooled and concentrated to give the title compound, NMR (400 MHz, CDCl$_3$) 7.35, 7.00, 6.92, 5.20, 5.16, 4.10, 3.32, 2.15 and 1.79 δ and Anal. calculated for $C_{27}H_{27}FN_2O_5$: C, 67.77; H, 5.69; N, 5.85. Found: C, 67.44; H, 5.83; N, 5.65.

Step 2: 4-Fluoro-4-[4-[[(phenylmethoxy)carbonyl]amino]-2-fluorophenyl]-1-piperidinecarboxylic acid phenylmethyl ester To a solution of diethylaminosulfur trifluoride (DAST, 0.65 mL) in dry methylene chloride (49 mL) at −78° C. under N$_2$ is added a solution of 4-hydroxy-4-[4-[[(phenylmethoxy)carbonyl]amino]-2-fluorophenyl]-1-piperidinecarboxylic acid phenylmethyl ester (EXAMPLE 74, Step 1, 2.25 g) in dry methylene chloride (47 mL) over 2 mins. The resulting mixture is stirred at −78° C. for 1 hr and at ambient temperature for 30 mins and is then adjusted to pH 8 with saturated aqueous sodium bicarbonate (50 mL), diluted with water (50 mL), and the layers are separated. The organic phase is washed with water (25 mL) and saline (25 mL), dried over anhydrous sodium sulfate and concentrated under reduced pressure, and the residue is chromatographed on silica gel (230–400 mesh, 150 g), eluting with methanol/methylene chloride (0.5/99.5). Those fractions with an $R_f$=0.27 by TLC (ethyl acetate/hexane, 25/75) are pooled and concentrated to give the title compound (contaminated with approx. 15% of the elimination side product). An analytical sample is prepared by radial chromatography (1000μ silica gel rotor, ethyl acetate/hexane (20/80) eluent), mp 116–118° C.

Step 3: (R)-4-Fluoro-4-[4-[5-(hydroxymethyl)-2-oxo-3-oxazolidinyl]-2-fluorophenyl]-1-piperidinecarboxylic acid phenylmethyl ester A solution of 4-fluoro-4-4-[[(phenylmethoxy)carbonyl]amino]-2-fluorophenyl]-1-piperidinecarboxylic acid phenylmethyl ester (EXAMPLE 74, Step 2, 2.03 g, contaminated with the elimination side product) in dry tetrahydrofuran (21 mL) at −78° C. under $N_2$ is treated with n-butyllithium (2.80 mL, 1.6 M in hexanes) dropwise over 5 mins. The resulting mixture is stirred at −78° C. for 1.25 hrs and is then treated with (R)-(−)-glycidyl butyrate (0.63 mL) dropwise. The resulting solution is stirred at −78° C. for 1 hr, warmed to ambient temperature and stirred for an additional 20 hrs, after which the reaction is quenched with saturated aqueous ammonium chloride (10 mL), diluted with water (10 mL), and the layers are separated. The organic phase is washed with saline (10 mL), dried over anhydrous magnesium sulfate and concentrated under reduced pressure to give the crude product which is chromatographed on silica gel (230–400 mesh, 250 g), eluting with methanol/methylene chloride (3/97). Pooling and concentration of those fractions with an $R_f$=0.51 by TLC (methanol/chloroform, 10/90) and repurification by silica gel chromatography (230–400 mesh, 100 g, methanol/methylene chloride (4/96) eluent) gives the title compound (contaminated with the elimination side product from the starting material). An analytical sample is prepared by radial chromatography (2000μ silica gel rotor, ethyl acetate/hexane (60/40) eluent), NMR (400 MHz, $CDCl_3$) 7.45, 7.34, 7.18, 5.16, 4.74, 4.17, 3.97, 3.72, 3.22, 2.25 and 1.90 δ and HRMS calculated for $C_{23}H_{24}F_2N_2O_5$: 446.1653. Found: 446.1660.

Step 4: (R)-4-Fluoro-4-[4-[5-[[(methylsulfonyl)oxy]methyl]-2-oxo-3-oxazolidinyl]-2-fluoro]phenyl]-1-piperidinecarboxylic acid -phenylmethyl ester A solution of (R)-4-Fluoro-4-[4-[5-(hydroxymethyl)-2-oxo-3-oxazolidinyl]-2-fluorophenyl]-1-piperidinecarboxylic acid phenylmethyl ester (EXAMPLE 74, Step 3, 0.17 g) and triethylamine (0.080 mL) in dry methylene chloride (2 mL) at 0° C. under $N_2$ is treated with methanesulfonyl chloride (0.031 mL) dropwise. The resulting mixture is stirred at 0° C. for 12 hrs and at ambient temperature for 1.5 hrs, diluted with methylene chloride (10 mL), washed with water (5 mL), saturated aqueous sodium bicarbonate (5 mL) and saline (5 mL), dried over anhydrous sodium sulfate and concentrated under reduced pressure to give the title compound, HRMS calculated for $C_{24}H_{26}F_2N_2O_7S+H_1$: 525.1507. Found: 525.1522.

Step 5: (S)-N-[[2-Oxo-3-[4-(4-fluoro-4-piperidinyl)-3-fluorophenyl]-5-oxazolidinyl]methyl]acetamide A mixture of (R)-4-fluoro-4-[4-[5-[[(methylsulfonyl)oxy]methyl]-2-oxo-3-oxazolidinyl]-2-fluorophenyl]-1-piperidinecarboxylic acid phenylmethyl ester (EXAMPLE 74, Step 4, 0.190 g) and concentrated aqueous ammonium hydroxide (2 mL) in isopropanol (1 mL) and acetonitrile (2 mL) is placed in a sealed tube and immersed in an oil bath maintained at 95° C. for 18 hrs. The mixture is then diluted with methylene chloride (20 mL), washed with water (10 mL) and saline (10 mL), dried over anhydrous sodium sulfate and concentrated under reduced pressure to give the crude 5-aminomethyl-2-oxazolidinone intermediate ($R_f$=0.13 by TLC, methanol/chloroform, 5/95). A solution of this intermediate and pyridine (0.088 mL) in dry methylene chloride (3.6 mL) under $N_2$ is treated with acetic anhydride (0.051 mL), and the resulting solution is stirred at ambient temperature for 18 hrs. The mixture is then diluted with methylene chloride (10 mL), washed with water (5 mL), saturated aqueous sodium bicarbonate (5 mL) and saline (5 mL), dried over anhydrous sodium sulfate and concentrated under reduced pressure to give the crude acetamide intermediate which, after being combined with approx. 1.5 g of crude product from previous reaction workups, is chromatographed on silica gel (230–400 mesh, 150 g), eluting with a gradient of methanol/methylene chloride (1/99–2/98). Pooling and concentration of those fractions with an $R_f$=0.18 by TLC (methanol/chloroform, 5/95) gives 0.80 g (approx. 70% from the mesylate) of the product (contaminated with the elimination side product) as an amorphous, white solid which is used without further purification. A mixture of this intermediate (0.75 g) and 20% palladium hydroxide on carbon (200 mg) in methanol (30 mL) is shaken on a Parr apparatus under a hydrogen atmosphere at 40 psi for 1 hr, the catalyst is removed by filtration through Celite and the filtrate is concentrated under reduced pressure. The residue is chromatographed on silica gel (230–400 mesh, 45 g), eluting with a gradient of triethylamine/methanol/methylene chloride (1/9/90–1/4/95), and those fractions having an $R_f$=0.19 by TLC (triethylamine/methanol/chloroform, 1/9/90) are pooled and concentrated to give the title compound, mp 163–165° C.

Step 6: (S)-(−)-N-[[3-[4-[1-Formyl-4-fluoro-4-piperidinyl]-3-fluorophenyl]-2-oxo-5-oxazolidinyl]methyl]acetamide A mixture of (S)-3-N-[[2-oxo-3-[4-(4-fluoro-4-piperidinyl)-3-fluorophenyl]-5-oxazolidinyl]methyl]acetamide (EXAMPLE 74, Step 5, 205 mg), 1-(3-dimethylaminopropyl)-3-ethylcarbodiimide hydrochloride (145 mg) and formic acid (28 μL) in dry tetrahydrofuran (11.6 mL) is diluted with water to solubilize all reactants and stirred at ambient temperature for 6 hrs. The reaction is then diluted with methylene chloride (30 mL), washed with water (20 mL) and saline (20 mL), dried over anhydrous sodium sulfate and concentrated under reduced pressure, and the residue is chromatographed on silica gel (230–400 mesh, 40 g), eluting with a gradient of methanol/methylene chloride (3/97–5/95). Those fractions with an $R_f$=0.40 by TLC (methanol/chloroform, 10/90) are pooled and concentrated and the residue is recrystallized from chloroform/diethyl ether to give the title compound, mp 180–181° C. (decomp.).

EXAMPLE 75

(S)-N-[[2-Oxo-3-[3-fluoro-4-[1-[(acetoxy)acetyl]-2,3,4,7-tetrahydro-1H-azepin-5-yl]phenyl]-5-oxazolidinyl]methyl]acetamide Step 1: 2,3,4,7-Tetrahydro-5-[[(trifluoromethyl)sulfonyl]oxy]-1H-azepine-1-carboxylic acid 1,1-dimethylethyl ester (a) and 2,3,6,7-Tetrahydro-4-[[(trifluoromethyl)sulfonyl]oxy]-1H-azepine-1-carboxylic acid 1,1-dimethylethyl ester (b)

Following the general procedure of EXAMPLE 20, Step 2, and making non-critical variations but substituting 1-(1,1-dimethylethoxycarbonyl)-1,2,3,5,6,7-hexahydroazepin-4-one for 1-(1,1-dimethylethoxycarbonyl)-4-piperidone and isolating the regioisomers by chromatography on silica gel (230–400 mesh, ethyl acetate/hexane (5/95) eluent), the title compounds are obtained, (a) NMR ($CDCl_3$, 400 MHz) 5.87, 3.95, 3.55, 2.57, 1.95 and 1.46 δ and (b) NMR ($CDCl_3$, 400 MHz) 5.90, 3.54, 2.69, 2.35 and 1.47 δ.

Step 2: (S)-5-[4-[5-[(Acetylamino)methyl]-2-oxo-3-oxazolidinyl]-2-fluorophenyl]-2,3,4,7-tetrahydro-1H-azepinecarboxylic acid 1,1-dimethylethyl ester Following the general procedure of EXAMPLE 38, Step 1, and making non-critical variations but substituting 2,3,4, 7-tetrahydro-5-[[(trifluoromethyl)sulfonyl]oxy]-1(1H)-azepinecarboxylic acid 1,1-dimethylethyl ester (EXAMPLE 75, Step 1(A)) for 3,6-dihydro-4-[[(trifluoromethyl)sulfonyl]oxy]-1(2H)-pyridinecarboxylic acid 1,1-dimethylethyl ester, the title compound is obtained, NMR (CDCl$_3$, 400 MHz) 7.31, 7.12–6.95, 5.84, 4.76, 4.00, 3.98, 3.76, 3.61, 3.58, 2.51, 1.97, 1.85 and 1.42 δ.

Step 3: (S)-N-[[2-Oxo-3-[3-fluoro-4-[1-[(acetoxy)acetyl]-2,3,4,7-tetrahydro-1H-azepin-5-yl]phenyl]-5-oxazolidinyl]methyl]acetamide Following the general procedure of EXAMPLE 70, Step 3, and making non-critical variations but substituting (S)-5-[4-[5-[(acetylamino)methyl]-2-oxo-3-oxazolidinyl]-2-fluorophenyl]-2,3,4,7-tetrahydro-1H-azepine-1-carboxylic acid 1,1-dimethylethyl ester (EXAMPLE 75, Step 2) for (S)-(−)-3-[4-[5-[(acetylamino)methyl]-2-oxo-3-oxazolidinyl]-2-fluorophenyl]-5,6-dihydro-1(2H)-pyridinecarboxylic acid 1,1-dimethylethyl ester, the title compound is obtained, HRMS calculated for C$_{22}$H$_{26}$F$_1$N$_3$O$_6$: 448.1884. Found: 448.1888.

EXAMPLE 76

(S)-(−)-N-[[3-[4-[1-(Hydroxyacetyl)-2,3,4,7-tetrahydro-1H-azepin-5-yl]-3-fluorophenyl]-2-oxo-5-oxazolidinyl]methyl]acetamide Following the general procedure of EXAMPLE 71, and making non-critical variations but substituting (S)-N-[[2-oxo-3-[3-fluoro-4-[1-[(acetoxy)acetyl]-2,3,4,7-tetrahydro-1H-azepin-5-yl]phenyl]-5-oxazolidinyl]methyl]acetamide (EXAMPLE 75, Step 3) for (S)-(−)-N-[[2-oxo-3-[3-fluoro-4-[1-[(acetoxy)acetyl]-5,6-dihydro-2H-pyridin-3-yl]phenyl]-5-oxazolidinyl]methyl]acetamide, the title compound is obtained, NMR (CDCl$_3$, 400 MHz, mixture of rotamers) 7.41, 7.09–7.18, 6.07, 6.00, 5.87, 4.78, 4.25, 4.21, 4.05, 3.92, 3.87, 3.78, 3.67, 3.51, 2.63, 2.03 and 1.97 δ and HRMS calculated for C$_{20}$H$_4$F$_1$N$_3$O$_5$: 405.1700. Found: 405.1694.

EXAMPLE 77

(S)-(−)-N-[[2-Oxo-3-[3-fluoro-4-[1-[(acetoxy)acetyl]-2,3,6,7-tetrahydro-1-H-azepin-4-yl]phenyl]-5-oxazolidinyl]methyl]acetamide Step 1: (S)-4-[4-[5-[(Acetylamino)methyl]-2-oxo-3-oxazolidinyl]-2-fluorophenyl]-2,3,6,7-tetrahydro-1H-azepine-1-carboxylic acid 1,1-dimethylethyl ester Following the general procedure of EXAMPLE 38, Step 1, and making non-critical variations but substituting 2,3,6,7-tetrahydro-4-[[(trifluoromethyl)sulfonyl]oxy]-1(1H)-azepinecarboxylic acid 1,1-dimethylethyl ester (EXAMPLE 75, Step 1(B)) for 3,6-dihydro-4-[[(trifluoromethyl)sulfonyl]oxy]-1(2H)-pyridinecarboxylic acid 1,1-dimethylethyl ester, the title compound is obtained, mp 164–165° C.

Step 2: (S)-(−)-N-[[2-Oxo-3-[3-fluoro-4-[1-[(acetoxy)acetyl]-2,3,6,7-tetrahydro-1H-azepin-4-yl]phenyl]-5-oxazolidinyl]methyl]acetamide Following the general procedure of EXAMPLE 70, Step 3, and making non-critical variations but substituting (S)-4-[4-[5-[(acetylamino)methyl]-2-oxo-3-oxazolidinyl]-2-fluorophenyl]-2,3,6,7-tetrahydro-1H-azepine-1-carboxylic acid 1,1-dimethylethyl ester (EXAMPLE 77, Step 1) for (S)-(−)-3-[4-[5-[(acetylamino)methyl]-2-oxo-3-oxazolidinyl]-2-fluorophenyl]-5,6-dihydro-1(2H)-pyridinecarboxylic acid 1,1-dimethylethyl ester, the title compound is obtained, NMR (CDCl$_3$, 400 MHz, mixture of rotamers) 7.39, 7.15, 6.22, 5.90, 4.79, 4.04, 3.80–3.50, 2.70, 2.50, 2.19 and 2.02 δ and Anal. calculated for C$_{22}$H$_{26}$F$_1$N$_3$O$_6$: C, 59.05; H, 5.86; N, 9.39. Found: C, 58.70; H, 5.80; N, 9.43.

EXAMPLE 78

(S)-(−)-N-[[3-[4-[1-(Hydroxyacetyl)-2,3,6,7-tetrahydro-1H-azepin-4-yl]-3-fluorophenyl]-2-oxo-5-oxazolidinyl]methyl]acetamide Following the general procedure of EXAMPLE 71, and making non-critical variations but substituting (S)-(−)-N-[[2-oxo-3-[3-fluoro-4-[1-[(acetoxy)acetyl]-2,3,6,7-tetrahydro-1H-azepin-4-yl]phenyl]-5-oxazolidinyl]methyl]acetamide (EXAMPLE 77, Step 2) for (S)-(−)-N-[[2-oxo-3-[3-fluoro-4-[1-[(acetoxy)acetyl]-5,6-dihydro-2H-pyridin-3-yl]phenyl]-5-oxazolidinyl]methyl]acetamide, the title compound is obtained, NMR (CDCl$_3$, 400 MHz, mixture of rotamers) 7.41, 7.13, 6.08, 5.90, 4.78, 4.22, 4.04, 3.85–3.59, 3.51–3.41, 2.70, 2.52 and 2.02 δ and Anal. calculated for C$_{20}$H$_{24}$F$_1$N$_3$O$_5$: C, 59.25; H, 5.97; N, 10.36. Found: C, 58.91; H, 6.04; N, 10.19.

EXAMPLE 79

(5S)-(−)-N-[[3-[4-[1-(Hydroxyacetyl)hexahydro-1H-azepin-4-yl]-3-fluorophenyl]-2-oxo-5-oxazolidinyl]methyl]acetamide (as a mixture of diastereomers)

Following the general procedure of EXAMPLE 48, and making non-critical variations but substituting (S)-(−)-N-[[3-[4-[1-(hydroxyacetyl)-2,3,4,7-tetrahydro-1H-azepin-5-yl]-3-fluorophenyl]-2-oxo-5-oxazolidinyl]methyl]acetamide (EXAMPLE 76, Step 3) for (S)-(−)-N-[[3-[4-(3,6-dihydro-2H-pyran-4-yl)-3-fluorophenyl]-2-oxo-5-oxazolidinyl]methyl]acetamide and purifying the product by chromatography on silica gel (70–230 mesh, methanol/methylene chloride (7.5/92.5) eluent), the title compound is obtained, HRMS calculated for C$_{20}$H$_{26}$F$_1$N$_3$O$_5$+H$_1$: 408.1935. Found: 408.1928.

EXAMPLE 80

(S)-N-[[3-[3-Fluoro-4-(3,4-dihydro-2H-pyran-6-yl)phenyl]-2-oxo-5-oxazolidinyl]methyl]acetamide Step 1: 6-(tributylstannyl)-3,4-dihydro-2H-dihydropyran A solution of 3,4-dihydro-2H-dihydropyran (2.000 g, 23.8 mmol) and N,N,N',N'-tetramethylethylenediamine (0.50 mL, 3.09 mmol) under a nitrogen atmosphere was cooled to 0° C. and treated with n-butyllithium (19.30 mL of a 1.6 M solution in hexane, 30.94 mmol). The mixture was then warmed to ambient temperature overnight. The resultant mixture was cooled to −78° C., dry tetrahydrofuran (20 mL) was added, and then tributyltin chloride (6.40 mL, 23.8 mmol). The mixture was stirred at −78 ° C. for 1 h and then warmed to ambient temperature for 2 h. The reaction mixture was diluted with diethyl ether (50 mL), transferred to a separatory funnel and washed with 5% aqueous ammonium hydroxide and brine. The organic layer was then dried, filtered and concentrated to give a crude product. Distillation of the residue under reduced pressure afforded 1.80 g (47%) of the title compound with a purity of 55%.

Step 2: (S)-N-[[3-[3-Fluoro-4-(3,4-dihydro-2H-pyran-6-yl)phenyl]-2-oxo-5-oxazolidinyl]methyl]acetamide A solution of (S)-N-[[3-[3-fluoro-4-iodophenyl]-2-oxo-5-oxazolidinyl]methyl]acetamide (0.200 g, 0.53 mmol) in 1-methyl-2-pyrrolidinone (5 mL) under a nitrogen atmosphere was treated with Pd$_2$dba$_3$ (0.018 g, 0.02 mmol) and tri(2-furyl)phosphine (0.009 g, 0.04 mmol). After stirring 10 min at ambient temperature, the mixture was treated with 6-(tributylstannyl)-3,4-dihydro-2H-dihydropyran (0.538 g, 55% purity, 0.80 mmol). The atmosphere was evacuated and filled with nitrogen three times and then the mixture heated to 90° C. for 24 h. At this time the reaction mixture was cooled to ambient temperature and poured into ethyl acetate. A precipitate was noticed and removed by filtering the mixture through Celite. The filtrate was transferred to a separatory funnel and washed with water and brine, dried over sodium sulfate, filtered and concentrated in vacuo. The residue was chromatographed over silica gel, eluting with hexane, 20% acetone/hexane, and finally 5% methanol/ dichloromethane. Appropriate fractions were combined and concentrated in vacuo to give 0.196 g of a material containing a small amount of 1-methyl-2-pyrrolidinone. Recrystallization provided 0.128 g (68%) of the title compound. mp 161–163° C.; MS(EI): m/z 334.

EXAMPLE 81

(S)-N-[[3-[3-Fluoro-4-[1-(carbobenzyloxy)-3-azetidinyl]-phenyl]-2-oxo-5-oxazolidinyl]methyl]-acetamide Step 1: 3-(4-Amino-2-fluorophenyl)-3-hydroxy-1-(1,1-diphenylmethyl)azetidine Sec. butyllithium (22.5 mL of a 1.3 M solution in cyclohexane, 29.5 mmol) was added dropwise to a stirred solution of 1-(3-fluorophenyl)-2,2,5,5-tetramethyl-1-aza-2,5-disilacyclopentane (Example 20, Step 1) (6.0 g, 23.7 mmol) at −78° C. under nitrogen in dry THF (75 mL). After 2 hr a solution of 1-(1,1-diphenylmethyl)azetidin-3-one (5.6 g, 23.6 mmol) in dry THF (60 mL) was added dropwise and stirring continued at −78° for 2 hr, when the cooling bath was removed. After reaching room temperature, a solution of saturated ammonium chloride (75 mL) was added followed by water (200 mL). The mixture was extracted with ether (500 mL), washed with brine (100 mL), dried over magnesium sulfate, filtered and evaporated. The residue was dissolved in methanol (150 mL) and anhydrous potassium carbonate (6.0 g, 43.5 mmol) added and then stirred overnight. The suspension was filtered and the filtrate evaporated. The residue was partitioned between ether (500 mL) and water (200 mL). The water was extracted with additional ether (200 mL) and the combined ether extracts washed with brine (100 mL), dried over magnesium sulfate, filtered and evaporated to afford an orange foam. Chromatography over silica gel (150 g, 40–60 μm) eluting with 25–50% ethyl acetate-hexane gave the title compound as a pale yellow foam. $^1$H NMR δ (CDCl$_3$): 2.62, 3.53, 3.78, 4.41, 6.36, 6.41, 7.03, 7.14–7.30, 7.39–7.47.

Step 2: 3-(N-Carbobenzyloxy-3-fluoroanilin-4-yl)-3-hydroxy-1-(1,1-diphenylmethyl)azetidine To a solution of 3-(4-amino-2-fluorophenyl)-3-hydroxy-1-(1,1-diphenylmethyl)azetidine (Example 81, Step 1, 5.10 g, 14.7 mmol) in acetone (75 mL) was added a solution of sodium bicarbonate (2.52 g, 30.0 mmol) in water (40 mL) to give a creamy suspension. Benzyl chloroformate (2.57 g, 15.1 mmol) was added and stirring continued overnight. The suspension was filtered and the acetone evaporated. The residue was partitioned between the ethyl acetate (200 mL) and water (50 mL). The organic layer was washed with brine (50 mL), dried over magnesium sulfate, filtered and evaporated to leave an amber foam. Chromatography over silica gel (150 g, 40–60 μM) eluting with 1–2% methanol-methylene chloride gave the title compound as a cream foam. HRMS: meas. 483.2087, theory 483.2084.

Step 3: N-Carbobenzyloxy-3-(N-carbobenzyloxy-3-fluoroanilin-4-yl)-3-hydroxyazetidine Benzyl chloroformate (3.8 mL, 26.6 mmol) was added to a solution of 3-(N-carbobenzyloxy-3-fluoroanilin-4-yl)-3-hydroxy-1-(1,1-diphenylmethyl)azetidine (Example 81, Step 2, 1.60 g, 3.32 mmol) in benzene (30 mL) and then heated under reflux under nitrogen for 2 hr. The benzene was evaporated and the residue chromatographed over silica gel (150 g, 40–60 μm) eluting with 20–60% ethyl acetate-hexane. The title compound was obtained as a white foam. $^1$H NMR δ (CDCl$_3$): 3.32, 4.19, 4.42, 5.08, 5.17, 6.98, 7.11, 7.19, 7.24–7.43.

Step 4: N-Carbobenzyloxy-3-(N-carbobenzyloxy-3-fluoroanilin-4-yl)azetidine.

Triethylsilane (30 mL) and trifluoroacetic acid (12 mL) were added to a solution of N-carbobenzyloxy-3-(N-carbobenzyloxy-3-fluoroanilin-4-yl)-3-hydroxyazetidine (Example 81, Step 3, 4.3 g, 9.55 mmol) in methylene chloride (40 mL) and stirred for 2 days. Removal of the solvents at 45°/0.75 mm gave an amber oil. Chromatography over silica gel (150 g, 40–60 μm) eluting with 1–3% methanol-chloroform yielded the title compound as a solid, m.p. 95°.

Step 5: (R)-(−)-N-Carbobenzyloxy-3-[2-fluoro-4-[5-hydroxymethyl-2-oxo-3-oxazolidinyl]phenyl]azetidine n-Butyllithium (5.25 mL of a 1.6 M solution in hexane, 8.40 mmol) was added dropwise to a stirred solution of N-carbobenzyloxy-3-(N-carbobenzyloxy-3-fluoroanilin-4-yl)azetidine (Example 81, Step 4, 3.63 g, 8.36 mmol) at −78° under nitrogen in dry THF (30 mL), then stirred for 2 hr. A solution of R-glycidyl butyrate (1.21 g, 8.40 mmol) in dry THF (3.0 mL) was added and the cooling bath removed after 15 min. After 18 hr, the solvent was removed and the residue partitioned between ethyl acetate (150 mL) and saturated ammonium chloride solution (50 mL). The organic layer was washed with water (50 mL) and brine (50 mL), dried over magnesium sulfate, filtered and evaporated leaving an amber oil. Chromatography over silica gel (150 g, 40–60 μm) eluting with 2–5% methanol-chloroform gave the title compound as a sticky foam. FAB-HRMS: theory 401.1513 (M+1); meas 401.1521.

Step 6: (R)-(−)-N-Carbobenzyloxy-3-[2-fluoro-(5-[[(3-nitrophenylsulfonyl)oxy]methyl-2-oxo-3-oxazolidinyl]phenyl]azetidine 3-Nitrobenzenesulfonyl chloride (1.70 g, 7.67 mmol) was added to an ice cooled solution of (R)-(−)-N-carbobenzyloxy-3-2-fluoro-4-[5-hydroxymethyl-2-oxo-3-oxazolidinyl]-phenylazetidine (Example 81, Step 5, 2.79 g, 6.97 mmol) and triethylamine (1.41 g, 14.0 mmol) in methylene chloride (40 mL). After 16 hr, water (50 mL) and methylene chloride (100 mL) were added. The organic layer was washed with brine (50 mL), dried over magnesium sulfate, filtered and evaporated. The residue was chromatographed over silica gel (150 g, 40–60 μm) eluting with 25–100% ethyl acetate-hexane to give the title compound as a sticky foam. FAB-HRMS: theory 586.1290 (M+1); meas 586.1295.

Step 7: (S)-(−)-N-Carbobenzyloxy-3-[2-fluoro-4-[5-azidomethyl-2-oxo-3-oxazolidinyl]phenyl]azetidine A mixture of sodium azide (1.44 g, 22.1 mmol) and (R)-(−)-N-carbobenzyloxy-3-[2-fluoro-4-[5-[[(3-nitrophenylsulfonyl)oxy]-methyl]-2-oxo-3-oxazolidinyl] phenyl]azetidine (Example 81, Step 6, 2.60 g, 4.44 mmol) in DMF (30 mL) was stirred for 16 hr, then filtered. The solvent was removed at 38°/0.75 mm and the residue extracted with ethyl acetate (100 mL) and washed with water (3×50 mL) and brine (50 mL). After drying over magnesium sulfate, filtration and evaporation gave a yellow oil. Chromatography over silica gel (150 g, 40–60 μm) eluting with 1–3% methanol-methylene chloride gave the title compound as a pale yellow foam. FAB-HRMS: theory 426.1577 (M+1); meas. 426.1580.

Step 8: (S)-(–)-N-Carbobenzyloxy-3-[2-fluoro-4-[5-aminomethyl-2-oxo-3-oxazolidinyl]phenyl]azetidine To a stirred solution of (S)-(–)-N-carbobenzyloxy-3-[2-fluoro-4-[5-azidomethyl-2-oxo-3-oxazolidinyl]phenyl] azetidine (Example 81, Step 7, 1.63 g, 3.84 mmol) in dry THF (20 mL) was added triphenylphosphine (1.11 g, 4.23 mmol). After 3 hr, water (0.69 mL, 38.4 mmol) was added and the reaction stirred for 2 days at which time the solvents were evaporated. The residue was chromatographed over silica gel (150 g, 40–60 μm) eluting with 5–10% methanol-chloroform. The title compound was isolated as a viscous colorless oil. FAB-HRMS: theory 400.1672 (M+1); meas. 400.1676.

Step 9: (S)-N-[[3-[3-Fluoro-4-[1-(carbobenzyloxy)-3-azetidinyl]phenyl]-2-oxo-5-oxazolidinyl]methyl]acetamide Pyridine (1.0 mL), acetic anhydride (1.0 mL) and a few crystals of 4 dimethylaminopyridine were added to a stirred solution of (S)-(–)-N-carbobenzyloxy-3-[2-fluoro-4-[5-aminomethyl-2-oxo-3-oxazolidinyl]phenyl]azetidine (Example 81, Step 8, 1.42 g, 3.56 mmol) in methylene chloride (30 mL), then stirred for 1 hr. The solvents were removed at 38°/0.75 mm and the residue chromatographed over silica gel (50 g, 40–60 μm) eluting with 1–2% methanol-chloroform. The title compound was isolated as a white foam. FAB-HRMS: theory 442.1778 (M+1); meas. 442.1777.

EXAMPLE 82

(S)-N-[[3-[3-Fluoro-4-[3-azetidinyl]phenyl]-2-oxo-5-oxazolidinyl]methyl]acetamide A solution of (S)-N-[[3-[3-fluoro-4-[1-(carbobenzyloxy)-3-azetidinyl]phenyl]-2-oxo-5-oxazolidinyl]methyl]acetamide (Example 81, Step 9, 1.44 g, 3.26 mmol) in ethyl acetate (25 mL) and absolute ethanol (50 mL) was added to 10% Pd/C (1.0 g) and hydrogenated at 30 psi for 7 hr. Filtration and evaporation gave the title compound as a white glassy solid. FAB-HRMS: theory 308.1410 (M+1); meas. 308.1408.

EXAMPLE 83

(S)-N-[[3-[3-Fluoro-4-[1-(methoxycarbonyl)-3-azetidinyl]phenyl]-2-oxo-5-oxazolidinyl]methyl]acetamide Triethylamine (150 μL, 1.08 mmol) and methyl chloroformate (65 μL, 0.84 mmol) were added to a chloroform (5 mL) suspension of (S)-N-[[3-[3-fluoro-4-[3-azetidinyl]phenyl]-2-oxo-5-oxazolidinyl]methyl]acetamide (Example 82, 153 mg, 0.50 mmol) and stirred overnight. Additional chloroform (25 mL) was added and the solution washed with water (15 mL) and brine (15 mL). Drying over magnesium sulfate, filtration, and evaporation gave a foam. Chromatography over silica gel (50 g, 40–60 μm) eluting with 1–3% methanol-chloroform gave the title compound as a white solid. FAB-HRMS: theory 366.1465 (M+1); meas. 366.1468.

EXAMPLE 84

(S)-N-[[3-[3-Fluoro-4-[1-(formyl)-3-azetidinyl] phenyl]-2-oxo-5-oxazolidinyl]methyl]acetamide N-Formylbenzotriazole (115 mg, 0.78 mmol) was added to a stirred suspension of (S)-N-[[3-[3-fluoro-4-[3-azetidinyl]phenyl]-2-oxo-5-oxazolidinyl]methyl]acetamide (Example 82, 153 mg, 0.50 mmol) in THF (5 mL) and stirred overnight. The solvent was removed and the residue chromatographed over silica gel (50 g, 40–60 μm) eluting with 2–5% methanol-chloroform to give the title compound as a white foam. FAB-HRMS: theory 336.1356 (M+1); meas. 336.1357.

EXAMPLE 85

(S)-(–)-N-[[3-[4-[1-(4-Oxo-2-thiazolinyl)-4-piperidinyl]-3-fluorophenyl]-2-oxo-5-oxazolidinyl]methyl]acetamide A mixture of (S)-(–)-N-[[2-oxo-3-[4-(4-piperidinyl)-3-fluorophenyl]-5-oxazolidinyl]methyl]acetamide (EXAMPLE 20, 310 mg), methyl thiocyanatoacetate (121 mg, *Bull. Chem. Soc. Jpn.* 1972, 45(5), 1507) and glacial acetic acid (55 mg) in absolute ethanol (5 mL) is stirred at reflux under $N_2$ for 4 hrs and then cooled to ambient temperature, diluted with methylene chloride (45 mL), washed with water (2×15 mL) and saline (20 mL), dried over anhydrous sodium sulfate and concentrated under reduced pressure. The residue is chromatographed on silica gel (230–400 mesh, 45 g), eluting with methanol/methylene chloride (4/96), and those fractions with an $R_f$=0.47 by TLC (methanol/chloroform, 10/90) are pooled and concentrated to give the title compound, mp 222–224° C. (decomp.).

EXAMPLE 86

(S)-(–)-N-[[3-[4-[1-(4-Oxo-2-thiazolinyl)-3,6-dihydro-2H-pyridin-5-yl]-3-fluorophenyl]-2-oxo-5-oxazolidinyl]methyl]acetamide Following the general procedure of EXAMPLE 85, and making non-critical variations but substituting (S)-(–)-N-[[2-oxo-3-[4-(3,6-dihydro-2H-pyridin-4-yl)-3-fluorophenyl]-5-oxazolidinyl]methyl]acetamide (EXAMPLE 38) for (S)-(–)-N-[[2-oxo-3-[4-(4-piperidinyl)-3-fluorophenyl]-5-oxazolidinyl]methyl]acetamide, the title compound is obtained, mp 209–211° C. (decomp.).

EXAMPLE 87

(S)-(–)-N-[[3-[4-[1-[5-Methyl-1,3,4-thiadiazol-2-yl]-4-piperidinyl]-3-fluorophenyl]-2-oxo-5-oxazolidinyl]methyl]acetamide Step 1: 2-Bromo-5-methyl-1,3,4-thiadiazole To a solution of aqueous hydrobromic acid (48%, 40 mL) containing a trace amount of copper powder at –10° C. is added a mixture of 2-amino-5-methyl-1,3,4-thiadiazole (2.88 g) and sodium nitrite (7.76 g) portionwise over 45 mins with vigorous stirring. The resulting mixture is stirred at –10° C. for 1.5 hrs and at ambient temperature for an additional 1.5 hrs and is then cooled in an ice bath, neutralized with aqueous sodium hydroxide (50%), diluted with saturated aqueous sodium hydrogensulfite till the mixture no longer turns potassium iodide-starch test paper blue and filtered to remove insoluble material (rinsing with hot water). The filtrate is extracted with methylene chloride (4×100 mL), and the combined organic phase is dried over anhydrous sodium sulfate and concentrated under reduced pressure to give the crude product which is then chromatographed on silica gel (70–230 mesh, 75 g), eluting with ethyl acetate/hexane (50/50). Pooling and concentration of those fractions with an $R_f$=0.78 by TLC (methanol/chloroform, 10/90) gives the title compound, mp 107–108° C.

Step 2: (S)-(–)-N-[[3-[[4-[1-(5-Methyl-1,3,4-thiadiazol-2-yl]-3,6-dihydro-2H-pyridin-4-yl]-3-fluorophenyl]-2-oxo-5-oxazolidinyl]methyl]acetamide A mixture of (S)-(–)-N-[[2-oxo-3-[4-(4-piperidinyl)-3-fluorophenyl]-5-oxazolidinyl]methyl]acetamide (EXAMPLE 20, 550 mg), 2-bromo-5-methyl-1,3,4-thiadiazole (EXAMPLE 87, Step 1, 323 mg) and potassium hydrogenphosphate (571 mg) in dimethyl sulfoxide (16 mL) is stirred under $N_2$ at 100° C. for 2 hrs, cooled to ambient temperature, diluted with water (20 mL) and extracted with methylene chloride (3×20 mL). The combined organic phase is washed with water (20 mL) and saline (10 mL), dried over anhydrous sodium sulfate and concentrated to give the crude product which is then chromatographed on silica gel (230–400 mesh, 45 g), eluting with a gradient of methanol/methylene chloride (2/98–3/97). Pooling and concentration of those fractions with an $R_f$=0.44 by TLC (methanol/chloroform, 10/90) gives the title compound, mp 193–195° C.

EXAMPLE 88

(S)-(–)-N-[[3-[4-[1-(5-Methyl-1,3,4-thiadiazol-2-yl)-3,6-dihydro-2H-pyridin-5-yl]-3-fluorophenyl]-2-oxo-5-oxazolidinyl]methyl]acetamide Following the general procedure of EXAMPLE 87, Step 2, and making non-critical variations but substituting (S)-(–)-N-[[2-oxo-3-[4-(3,6-dihydro-2H-pyridin-4-yl)-3-fluorophenyl]-5-oxazolidinyl]methyl]acetamide (EXAMPLE 38) for (S)-(–)-N-[[2-oxo-3-[4-(4-piperidinyl)-3-fluorophenyl]-5-oxazolidinyl]methyl]acetamide, the title compound is obtained, mp 229–231° C. (decomp.).

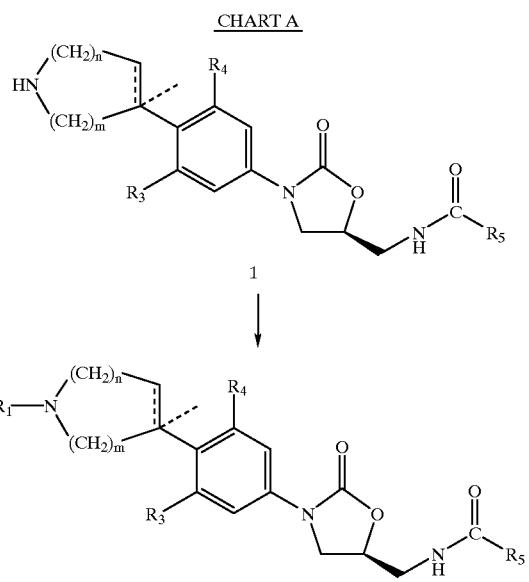

CHART A

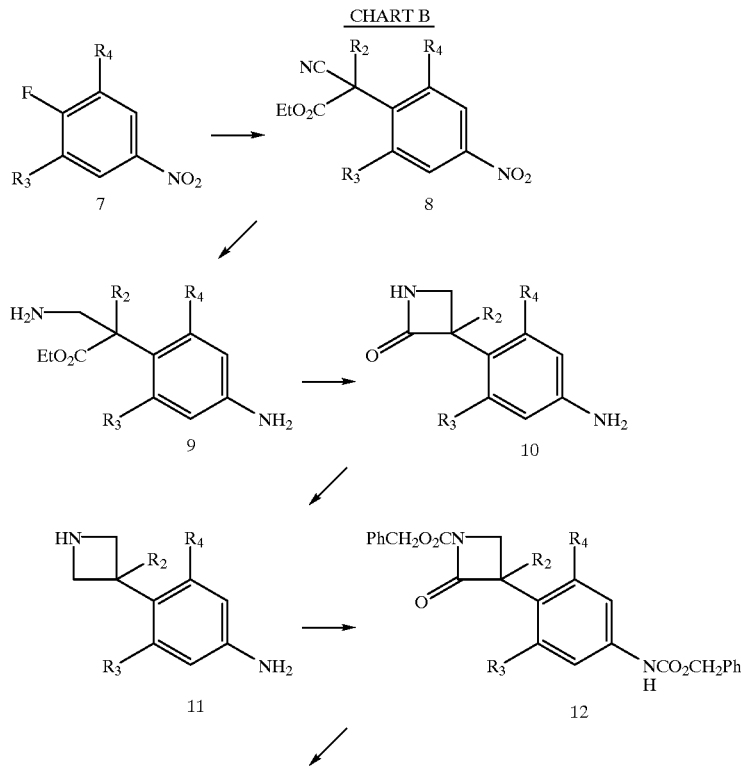

CHART B

-continued
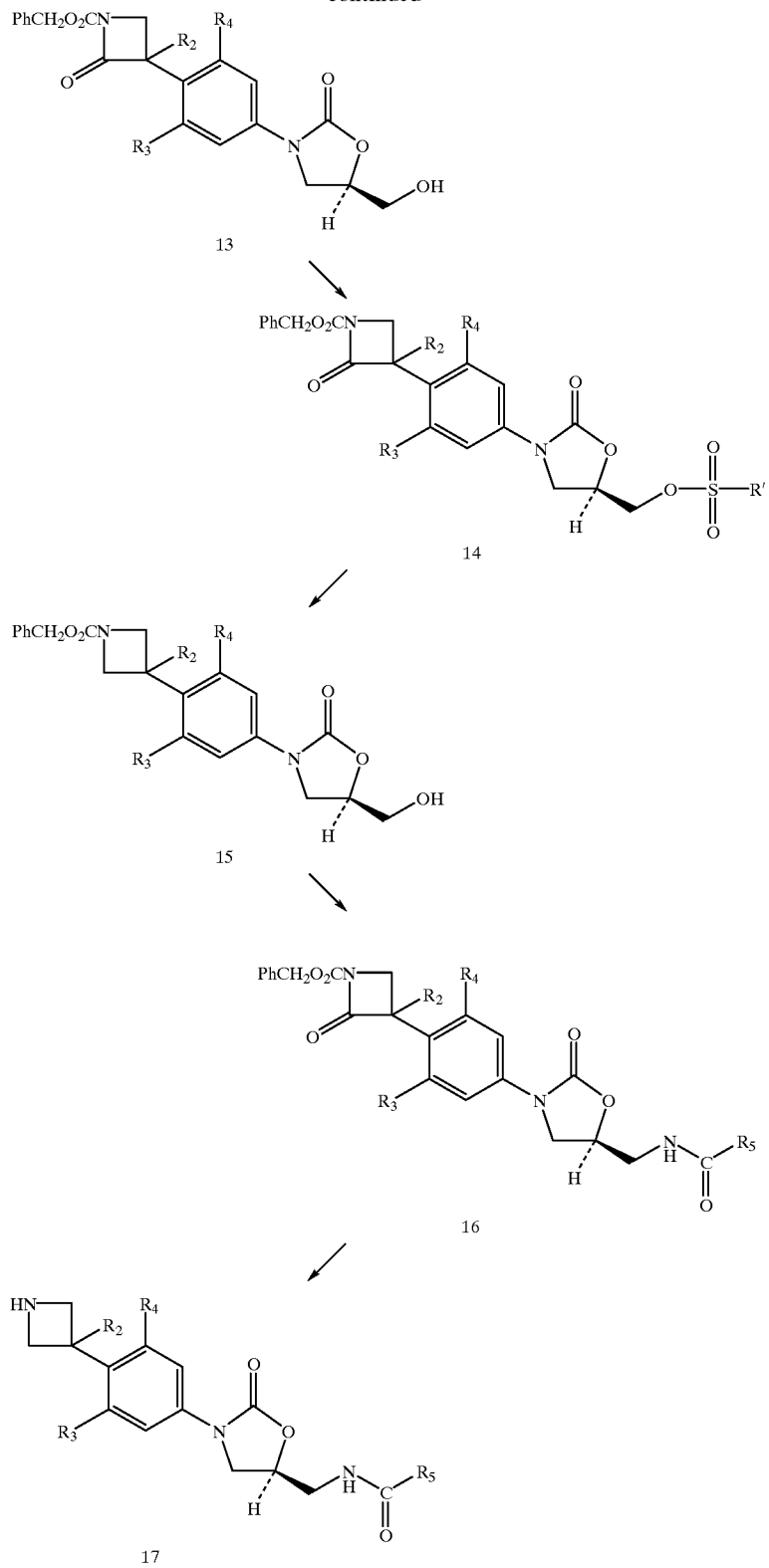

CHART C
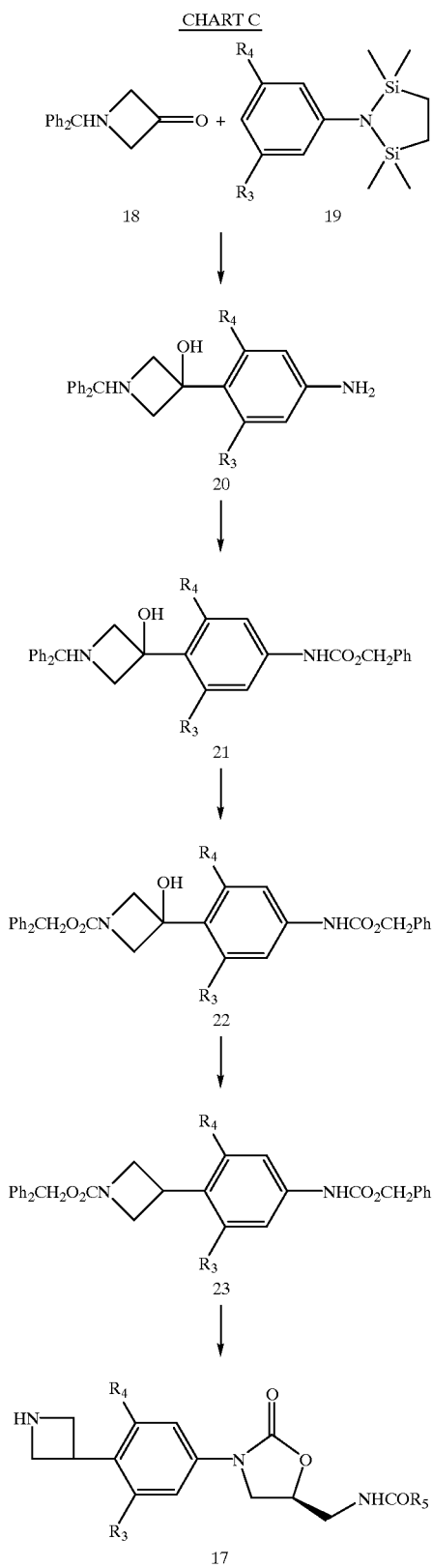
CHART D
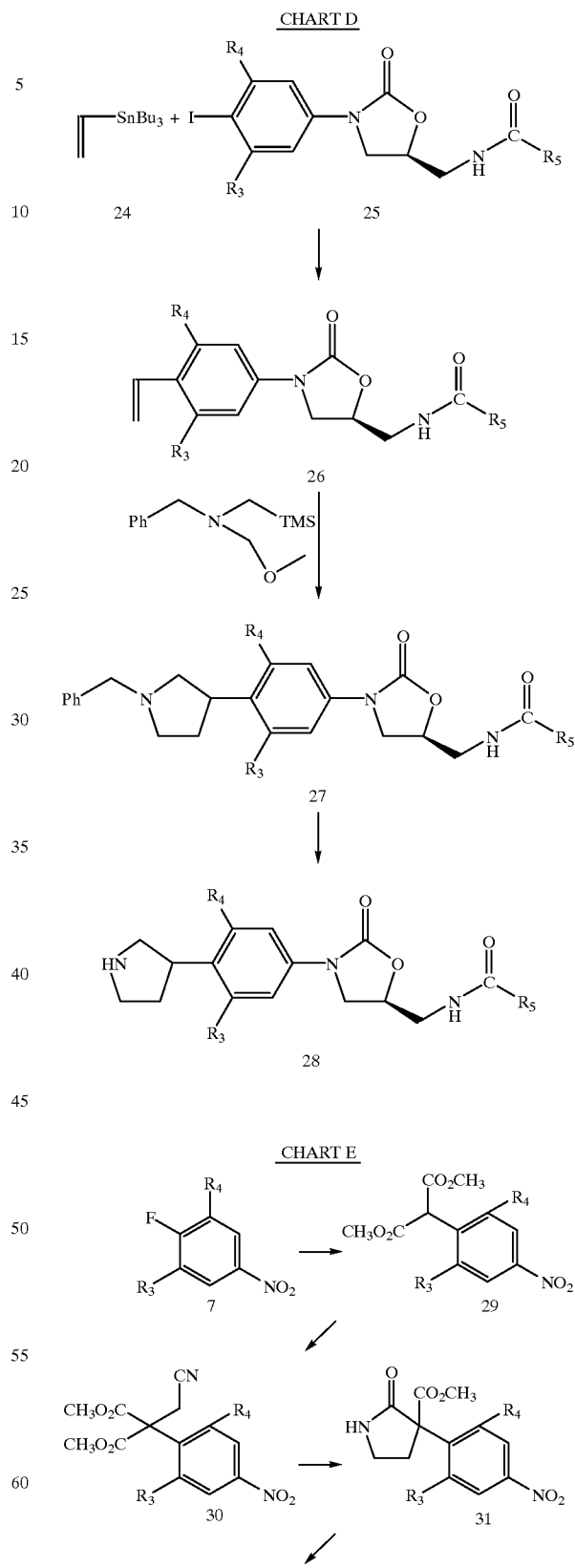

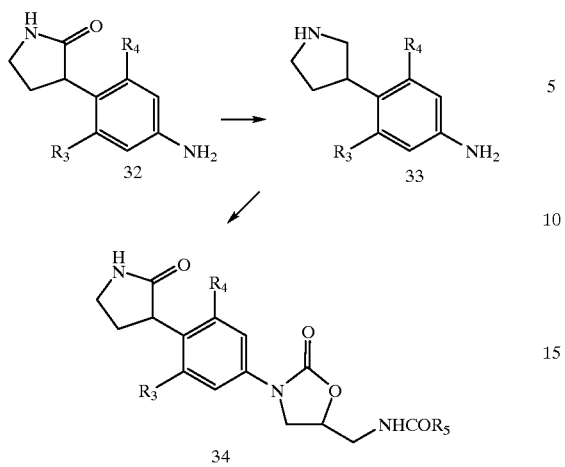
CHART F
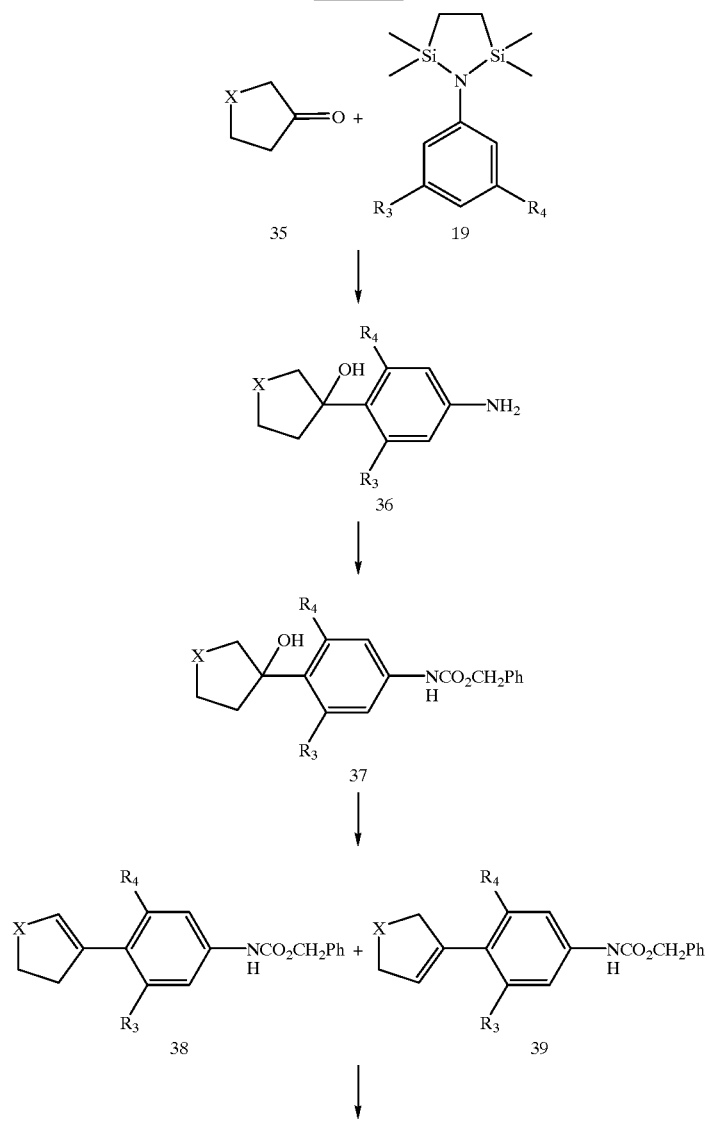

73
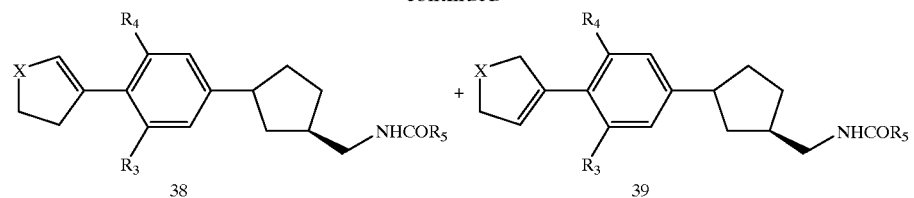
74
-continued
CHART G
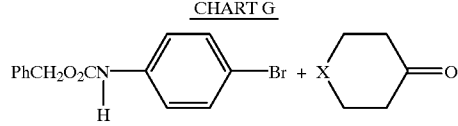
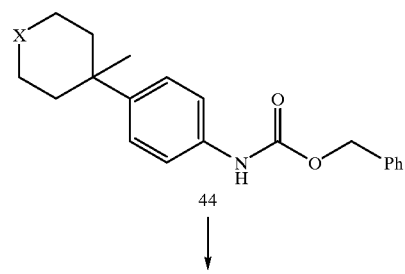
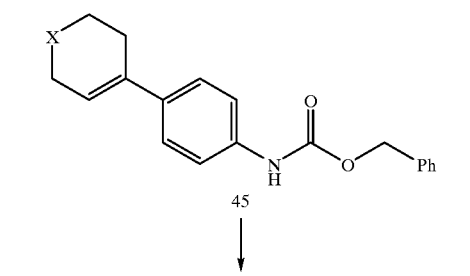
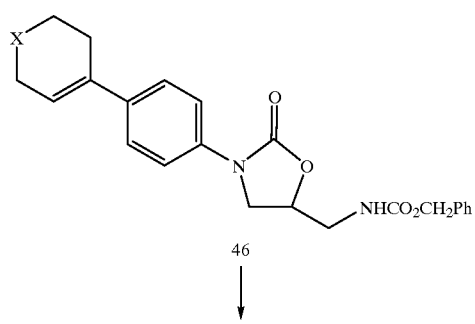
CHART H
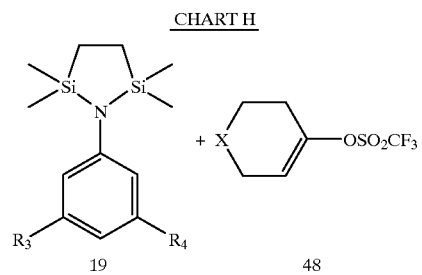
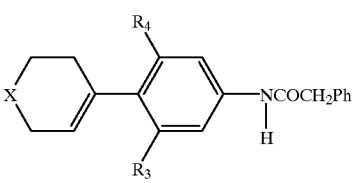
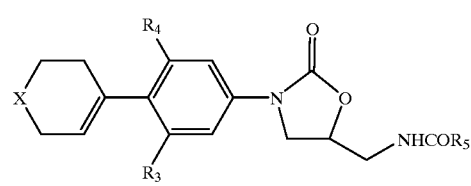
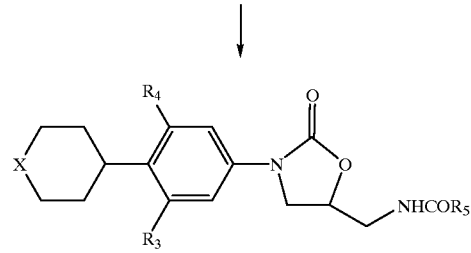

CHART I
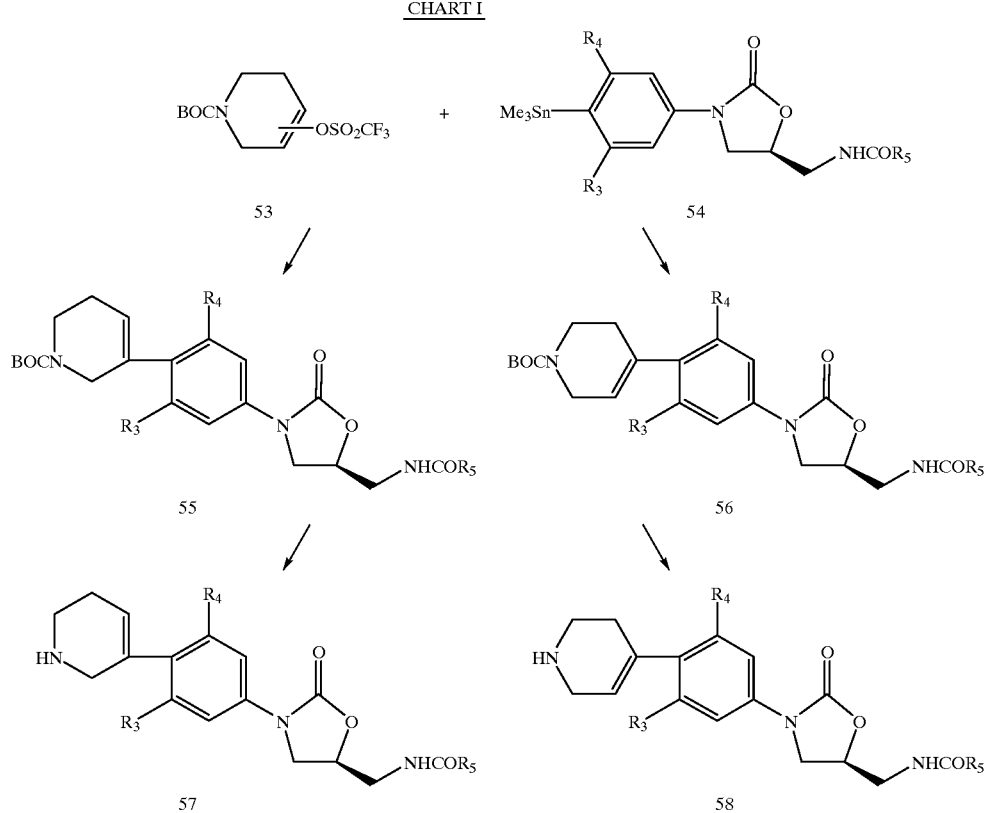
CHART J
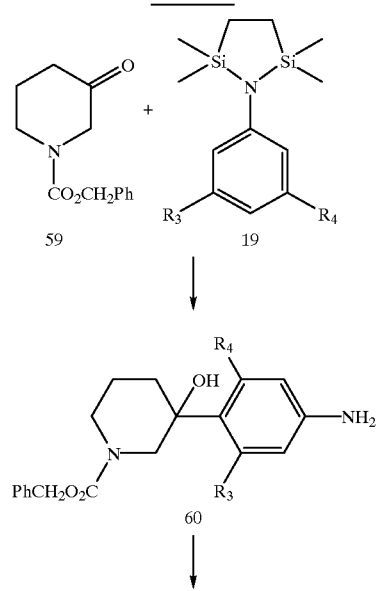

-continued

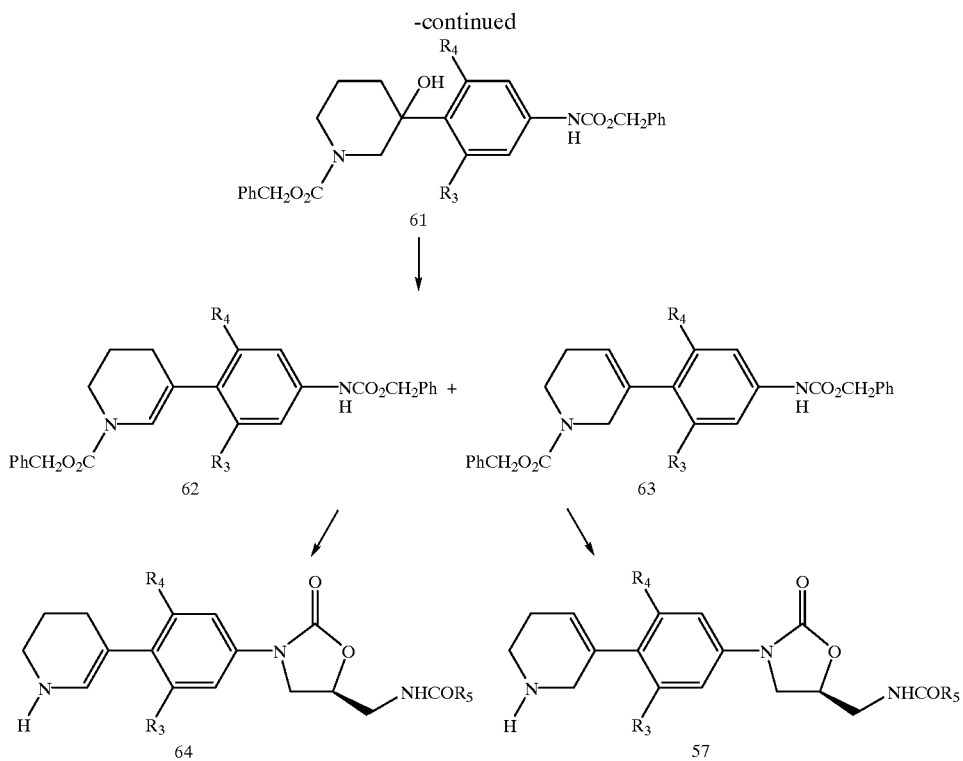

We claim:

1. A compound of Formula I:

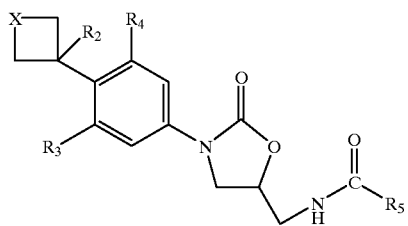

(I)

or pharmaceutical acceptable salts thereof wherein:

X is
  a) $S(O)_g$, or
  b) O;

$R_2$ is
  a) H,
  b) methyl, or
  c) OH;

$R_3$ and $R_4$ are independently
  a) H, or
  b) halo;

$R_5$ is
  a) H,
  b) $C_{1-12}$ alkyl, optionally substituted with one or more halo,
  c) $C_{3-12}$ cycloalkyl,
  d) $C_{1-6}$ alkoxy;

and g is 0, 1, or 2.

2. A compound of claim 1 wherein $R_3$ and $R_4$ are independently H or F.

3. A compound of claim 1 wherein at least one of $R_3$ or $R_4$ is H.

4. A compound of claim 1 wherein $R_2$ is H.

5. A compound of claim 1 wherein $R_5$ is methyl or ethyl, optionally substituted with one to three F or Cl.

6. A method for treating microbial infections in patients comprising: administering to a patient in need thereof an effective amount of a compound of Formula I as shown in claim 1.

7. The method of claim 6 wherein said compound of Formula I is administered orally, parenterally or topically in a pharmaceutical composition.

8. The method of claim 6 wherein said compound is administered in an amount of from about 0.1 to about 100 mg/kg of body weight/day.

* * * * *